(12) United States Patent
Gavathiotis et al.

(10) Patent No.: US 11,382,898 B2
(45) Date of Patent: Jul. 12, 2022

(54) BAX ACTIVATORS AND USES THEREOF IN CANCER THERAPY

(71) Applicant: Albert Einstein College of Medicine, Bronx, NY (US)

(72) Inventors: Evripidis Gavathiotis, Roslyn, NY (US); Denis E. Reyna, Bronx, NY (US); Felix Kopp, Brooklyn, NY (US); Ulrich G. Steidl, New Rochelle, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 160 days.

(21) Appl. No.: 16/616,249

(22) PCT Filed: May 24, 2018

(86) PCT No.: PCT/US2018/034279
§ 371 (c)(1),
(2) Date: Nov. 22, 2019

(87) PCT Pub. No.: WO2018/222473
PCT Pub. Date: Dec. 6, 2018

(65) Prior Publication Data
US 2020/0093802 A1    Mar. 26, 2020

Related U.S. Application Data

(60) Provisional application No. 62/513,488, filed on Jun. 1, 2017, provisional application No. 62/546,041, filed on Aug. 16, 2017.

(51) Int. Cl.
| | | |
|---|---|---|
| *A61K 31/427* | (2006.01) |
| *A61P 35/02* | (2006.01) |
| *A61K 31/429* | (2006.01) |
| *A61K 31/437* | (2006.01) |
| *A61K 31/4439* | (2006.01) |
| *A61K 31/5377* | (2006.01) |
| *A61K 45/06* | (2006.01) |

(52) U.S. Cl.
CPC .......... *A61K 31/427* (2013.01); *A61K 31/429* (2013.01); *A61K 31/437* (2013.01); *A61K 31/4439* (2013.01); *A61K 31/5377* (2013.01); *A61P 35/02* (2018.01); *A61K 45/06* (2013.01)

(58) Field of Classification Search
CPC ............................ C07D 417/04; A61K 31/415
See application file for complete search history.

(56) References Cited

U.S. PATENT DOCUMENTS

| | | |
|---|---|---|
| 9,303,024 B2 | 4/2016 | Walensky et al. |
| 2015/0133450 A1 | 5/2015 | Cardone et al. |
| 2017/0114100 A1 | 4/2017 | Gavathiotis |

FOREIGN PATENT DOCUMENTS

| | | |
|---|---|---|
| WO | 2013/055949 A2 | 4/2013 |
| WO | 2015/183989 A1 | 12/2015 |

OTHER PUBLICATIONS

Chen et al. "An Interconnected Hierarchical Model of Cell Death Regulation by the BCL-2 Family," Nat Cell Biol, Sep. 7, 2015, vol. 17, Iss. 10, pp. 1270-1281.

Gavathiotis et al. "Direct and selective small-molecule activation of proapoptotic BAX," Nat. Chem Biol, May 27, 2012, vol. 8, Iss. 7, pp. 639-645.

*Primary Examiner* — Kamal A Saeed
(74) *Attorney, Agent, or Firm* — Fox Rothschild LLP

(57) ABSTRACT

Activators of BAX and their uses in cancer therapy are disclosed.

13 Claims, 24 Drawing Sheets

Specification includes a Sequence Listing.

BAX ACTIVATORS AND USES THEREOF IN CANCER THERAPY

CROSS-REFERENCE TO RELATED APPLICATION

This application claims the benefit of U.S. Provisional Patent Application No. 62/546,041, filed on Aug. 16, 2017 and U.S. Provisional Patent Application No. 62/513,488, filed on Jun. 1, 2017, the contents of which is herein incorporated by reference in its entirety.

STATEMENT OF GOVERNMENT INTEREST

This invention was made with government support under grant numbers CA178394 and CA013330 awarded by the National Institutes of Health. The government has certain rights in the invention.

BACKGROUND OF THE INVENTION

Throughout this application various publications are referred to by number in parentheses. Full citations for these references may be found at the end of the specification. The disclosures of these publications, and all patents, patent application publications and books referred to herein, are hereby incorporated by reference in their entirety into the subject application to more fully describe the art to which the subject invention pertains.

Programmed cell death, or apoptosis, is a fundamental process that regulates the critical balance between cellular life and death (Danial and Korsmeyer 2004). Dysregulation of apoptosis results in an imbalance of normal homeostasis contributing to diseases such as cancer (Bredesen et al. 2006, Johnstone et al. 2002). The BCL-2 family of proteins comprises a complex interaction network that regulates the commitment of the cell to apoptosis at the mitochondrial pathway (Chipuk et al. 2010, Youle and Strasser 2008). The BCL-2 family includes both pro- and anti-apoptotic proteins. The pro-apoptotic BCL-2 proteins—BCL-2-associated X-protein (BAX) and BCL-2 homologous Antagonist Killer (BAK)—induce mitochondrial outer-membrane permeabilization and represent the key gatekeepers and effectors of mitochondrial apoptosis. Thus, activation of BAX or BAK promotes apoptosis and can overcome the resistance and blockades of tumor cells to undergo cell death.

Cancer cells depend on their ability to enforce cell survival pathways and block cell death mechanisms (Hanahan and Weinberg 2011). It is well established that cancer cells reprogram the BCL-2 family interaction network that regulates mitochondrial apoptosis to ensure their growth, maintenance and resistance to chemotherapy, radiation and targeted therapies (Hata et al., 2015; Llambi and Green, 2011). Most frequently, cancer cells overexpress anti-apoptotic BCL-2 family members such as BCL-2, BCL-$X_L$ and MCL-1 that bind and neutralize the BH3 death domains of the activated pro-apoptotic BCL-2 members BAX, BAK and the BH3-only proteins such as BIM and BID (Letai, 2008; Youle and Strasser, 2008). Elucidation of the BCL-2 family interactions has led to the development of clinical inhibitors targeting anti-apoptotic BCL-2, BCL-XL and BCL-W (navitoclax/ABT-263) or BCL-2 only (venetoclax/ABT-199) that prevent neutralization of BH3 death domains and promote BAX/BAK-mediated apoptosis (Juin et al., 2013; Oltersdorf et al., 2005; Souers et al., 2013). Evaluation of venetoclax and navitoclax in preclinical models and clinical trials demonstrated promising efficacy in tumors that are highly dependent on BCL-2 and/or BCL-XL (Leverson et al., 2015; Roberts et al., 2015; Rudin et al., 2012). However, studies highlighted the limited efficacy and resistance in cancers that rely on or overexpress additional anti-apoptotic proteins, such as MCL-1, which are not inhibited by the aforementioned inhibitors (Beroukhim et al., 2010; Konopleva et al., 2006; van Delft et al., 2006). Efforts in developing drug-like MCL-1 inhibitors has been proven challenging although a recent study suggested that selective MCl-1 inhibitors would be effective for a range of tumors (Belmar et al., 2015; Kotchy et al., 2016; Perciavalle et al., 2013).

Novel approaches to target the BCL-2 family proteins are therefore in pursuit (e.g., Garner et al. 2017). Pro-apoptotic BAX is the cardinal executioner BCL-2-family member that upon conformational activation and oligomerization at the mitochondrial outer membrane (MOM) causes permeabilization of the MOM and release of mitochondrial factors e.g. cytochrome c, and Smac/Diablo that activate the caspase cascade of apoptosis (Luna-Vargas and Chipuk, 2016; Walensky and Gavathiotis, 2011). Cells deficient for BAX become less sensitive to various apoptotic stimuli and become resistant when both BAX and BAK are deleted (Wei et al., 2001). Selective inhibitors of anti-apoptotic BCL-2 proteins including venetoclax and navitoclax are effective inducers of apoptosis because they release BH3-only proteins (e.g. BIM, BID) from the anti-apoptotic BCL-2 proteins to activate BAX and BAK (Juin et al., 2013; Oltersdorf et al., 2005; Souers et al., 2013). Moreover, induction of BAX-dependent apoptosis by BH3-only proteins can be induced by several classic chemotherapeutic agents (Zhang et al., 2000). However, in several tumors, BH3-only proteins can be suppressed or deleted at transcription, translation and post-translational levels, rendering these tumors more insensitive to current treatments (Hata et al., 2015; Juin et al., 2013). Interestingly, the vast majority of cancer cells contain functional BAX in an inactive conformation or suppressed by anti-apoptotic proteins; mutations or alterations in BAX that may cause its inactivation occur, albeit at a low frequency in different tumor types analyzed by the TCGA Research Network (<2%) (Gao et al., 2013).

Direct activators of BAX may be particularly applicable in the treatment of cancer and could selectively overcome anti-apoptotic resistance of cancer cells and spare normal cells. The present invention addressed the need for identifying activators of BAX for therapeutic treatments.

SUMMARY OF THE INVENTION

The invention provides activators of BCL-2-associated X-protein (BAX) both as single therapeutic agents and in combination with other agents for treatment of cancer.

The invention provides pharmaceutical compositions comprising a compound having the structure of Formula (I)

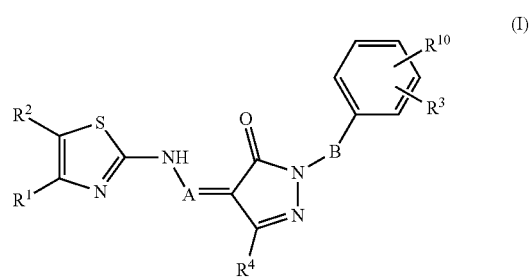

wherein the variables are defined herein below, and pharmaceutically acceptable salts, esters and prodrugs thereof.

The invention provides methods of treating a cancer in a subject comprising administering to the subject an activator of BCL-2-associated X-protein (BAX) in combination with an inhibitor of BCL-2 or with an inhibitor of BCL-xL and BCL-2, in an amount effective to treat a cancer in a subject.

DETAILED DESCRIPTION OF THE INVENTION

Figures 1A, 1B, 1C, 1D, 1E, 1F, 1G, 1H, 1I:
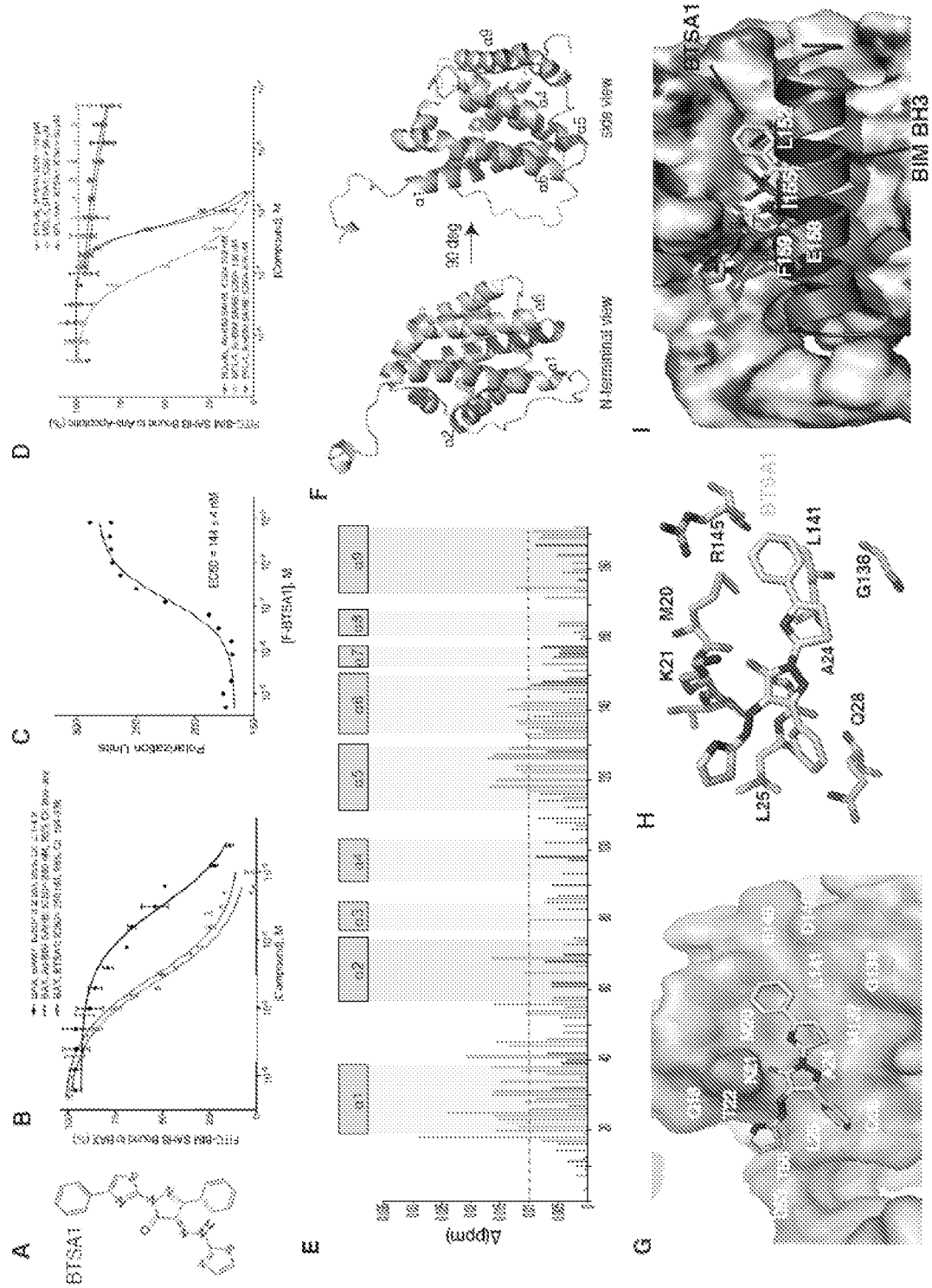
FIG. 1A-1I. BTSA1 is a high affinity and selective BAX trigger site activator. (A) Chemical structure of BTSA1. (B) Competitive fluorescence polarization assay using FITC-BIM SAHB$_{A2}$ bound to BAX from BTSA1, BAM7 and Ac-BIM SAHB$_{A2}$. (C) Direct fluorescence polarization assay using fluorescent-labeled BTSA1 (F-BTSA1) and BAX. (D) Competitive fluorescence polarization assay using FITC-BIM SAHB$_{A2}$ bound to BCL-XL, MCL-1 and BFL-1 from BTSA1 and Ac-BIM SAHB$_{A2}$. (E) Measured chemical shift changes from comparative analysis of HSQCs using $^{15}$N-labelled BAX upon BTSA1 titration up to a ratio of 1:1 are plotted as a function of BAX residue number. (F) Mapping of the residues with significant backbone amide chemical shift change showing the co-localization of residues in the BAX trigger site (α1, α6, loop α1-α9). (G) Surface representation of BAX with BTSA1 (sticks) docked in the trigger site showing overlap with residues undergoing chemical shift changes. (H) Ribbon representation of the docked structure of BTSA1 showing possible interactions formed predominantly with the sidechains of hydrophobic residues and a key hydrogen bond between the pyrazolone group and K21 residue. (I) Structural overlay of the BAX:BIM BH3 structural model and the BAX:BTSA1 docked structure suggest similar type of interactions between BIM BH3 helix and BTSA1 at the BAX trigger site. The phenylthiazol group of BTSA1 mimicks hydrophobic interactions of the I155 and L152 of the BIM BH3 helix. The thiazol ring and part of the hydrazono group of BTSA1 overlaps with the F155 of the BIM BH3 helix. The pyrazolone group of BTSA1 forms a hydrogen bond with the sidechain of the K21 of BAX and is aligned with the E158 residue of the BIM BH3 helix that also forms a hydrogen bond with the sidechain of the K21. Data represent mean±SD (n=3) from three independent experiments or are representative of three independent experiments.

The invention provides a pharmaceutical composition comprising a pharmaceutically acceptable carrier and a compound of Formula (I), and a compound of Formula (I), where the compound of Formula (I) has the structure:

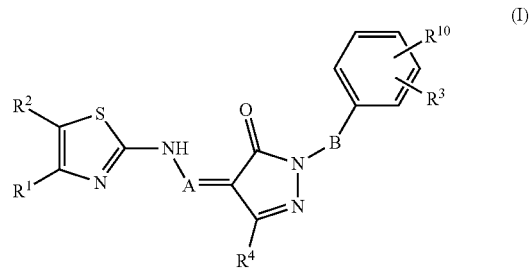

wherein

A is N or CH;

B is

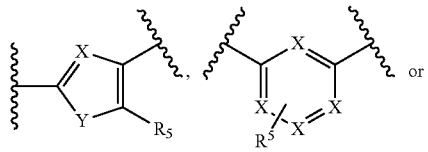

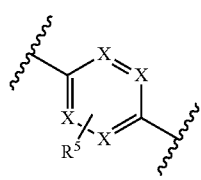

where ∽ represents the point of attachment to the scaffold;

X is CH or N;

Y is O, S, NH, CO, CS, or —CH=X—;

R1, R2, R4, and R5 are independently H, F, Cl, Br, I, OH, SH, NO₂, CF₃, COOH, COOR6, CHO, CN, NH₂, SO₄H, SO₂NH₂, NHNH₂, ONH₂, NHC=(O)NHNH₂, NHC=(O) NH₂, NHC=(O)H, NHC(O)—OH, NHOH, OCF₃, OCHF₂, NHR6, NHCONH₂, NHCONHR6, NHCOR6, NHSO₂R6, OCR6, COH, COR6, CH₂R6, CONH₂, CON(R6,R7), CH=N—OR6, CH=NR6, OR6, SR6, SOR6, SO₂R6, CH₂N(R6, R7), N(R6,R7), or optionally substituted lower (C1-C4) alkyl, alkenyl, alkynyl, cycloalkyl, heterocycloalkyl, aryl, heteroaryl, aralkyl, or heteroaralkyl, wherein the optional substituent is one or more of F, CF₃, Cl, Br, I, OH, SH, NO₂, R6, COOH, COOR6, CHO, CN, NH₂, NHR6, NHCONH₂, NHCONHR6, NHCOR6, NHSO₂R6, OCR6, COR6, CH₂R6, CON(R6,R7), CH=N—OR6, CH=NR6, OR6, SR6, SOR6, SO₂R6, COOR6, CH₂N(R6, R7), or N(R6,R7);

R1 and R2 can form a cyclic, heterocyclic, aryl or heteroaryl, wherein the aryl or heteroaryl is optionally substituted with OH, CO₂H or SO₂NH₂;

R3 and R10 are independently H, F, Cl, Br, I, OH, SH, CF₃, NO₂, R6, COOH, COOR6, CHO, CN, NH₂, SO₄H, SO₂NH₂, NHNH₂, ONH₂, NHC=(O)NHNH₂, NHC=(O) NH₂, NHC=(O)H, NHC(O)—OH, NHOH, OCF₃, OCHF₂, NHR6, NHCONH₂, NHCONHR6, NHCOR6, NHSO₂R6, OR6, OCR6, COR6, CH₂R6, CON(R6,R7), CH=N—OR6, CH=NR6, OR6, SR6, SOR6, SO₂R6, COOR6, CH₂N(R6, R7), N(R6,R7), lower (C1-C4) alkyl, alkenyl, or alkynyl;

R6 and R7 are independently H, C1-C6 alkyl, C1-C6 haloalkyl, C3-C6 cycloalkyl, C1-C6 alkoxy, C1-C6 haloalkoxy, C1-C6 thioalkoxy, or C1-C6 thiolhaloalkoxy;

or a pharmaceutically acceptable salt, ester or prodrug thereof.

The compound can have the structure of Formula (Ia)

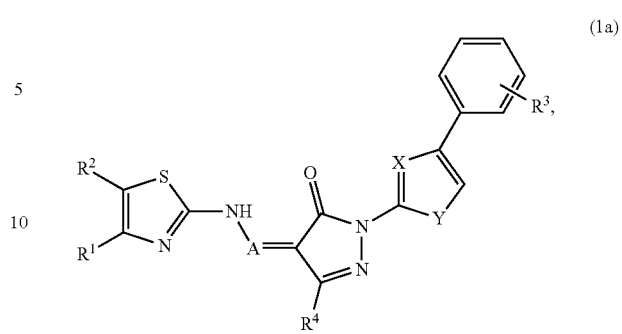

(Ia)

or a pharmaceutically acceptable salt, ester or prodrug thereof.

The compound can have the structure of Formula (Ib)

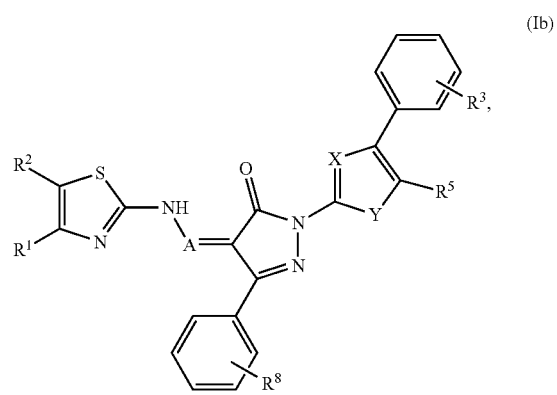

(Ib)

wherein R8 is F, CF₃, Cl, Br, I, OH, SH, CF₃, NO₂, SO₄H, SO₂NH₂, NHNH₂, ONH₂, NHC=(O)NHNH₂, NHC=(O) NH₂, NHC=(O)H, NHC(O)—OH, NHOH, OCF₃, OCHF₂, R6, COOH, COOR6, CHO, CN, NH₂, NHR6, NHCONH₂, NHCONHR6, NHCOR6, NHSO₂R6, OCR6, COR6, CH₂R6, CON(R6,R7), CH=N—OR6, CH=NR6, OR6, SR6, SOR6, SO₂R6, COOR6, CH₂N(R6, R7), N(R6,R7), lower (C1-C4) alkyl, alkenyl, or alkynyl;

or a pharmaceutically acceptable salt, ester or prodrug thereof.

The compound can have the structure of Formula (Ic)

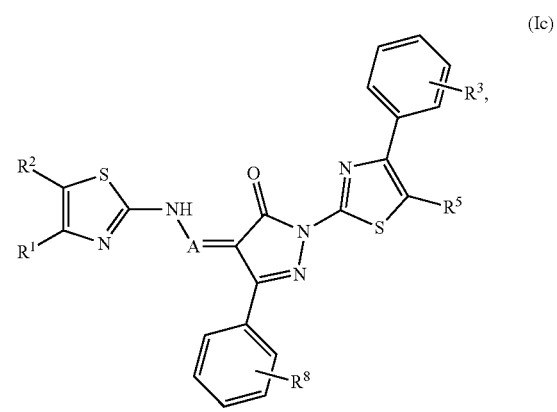

(Ic)

wherein R8 is F, CF₃, Cl, Br, I, OH, SH, CF₃, NO₂, SO₄H, SO₂NH₂, NHNH₂, ONH₂, NHC=(O)NHNH₂, NHC=(O) NH₂, NHC=(O)H, NHC(O)—OH, NHOH, OCF₃, OCHF₂, R6, COOH, COOR6, CHO, CN, NH₂, NHR6, NHCONH₂, NHCONHR6, NHCOR6, NHSO₂R6, OCR6, COR6, CH₂R6, CON(R6,R7), CH=N—OR6, CH=NR6, OR6, SR6, SOR6, SO₂R6, COOR6, CH₂N(R6, R7), N(R6,R7), lower (C1-C4) alkyl, alkenyl, or alkynyl;

or a pharmaceutically acceptable salt, ester or prodrug thereof.

The compound can have the structure of Formula (Id)

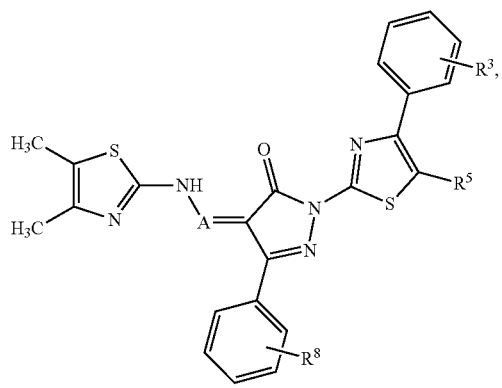

(Id)

wherein R8 is F, $CF_3$, Cl, Br, I, OH, SH, $CF_3$, $NO_2$, $SO_4H$, $SO_2NH_2$, $NHNH_2$, $ONH_2$, NHC=(O)$NHNH_2$, NHC=(O)$NH_2$, NHC=(O)H, NHC(O)—OH, NHOH, $OCF_3$, $OCHF_2$, R6, COOH, COOR6, CHO, CN, $NH_2$, NHR6, $NHCONH_2$, NHCONHR6, NHCOR6, $NHSO_2R6$, OCR6, COR6, $CH_2R6$, CON(R6,R7), CH=N—OR6, CH=NR6, OR6, SR6, SOR6, $SO_2R6$, COOR6, $CH_2N$(R6, R7), N(R6,R7), lower (C1-C4) alkyl, alkenyl, or alkynyl;

or a pharmaceutically acceptable salt, ester or prodrug thereof.

The compound can have the structure of Formula (Ie)

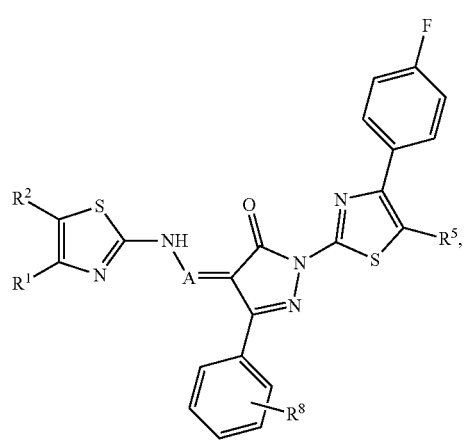

(Ie)

wherein R8 is F, $CF_3$, Cl, Br, I, OH, SH, $CF_3$, $NO_2$, $SO_4H$, $SO_2NH_2$, $NHNH_2$, $ONH_2$, NHC=(O)$NHNH_2$, NHC=(O)$NH_2$, NHC=(O)H, NHC(O)—OH, NHOH, $OCF_3$, $OCHF_2$, R6, COOH, COOR6, CHO, CN, $NH_2$, NHR6, $NHCONH_2$, NHCONHR6, NHCOR6, $NHSO_2R6$, OCR6, COR6, $CH_2R6$, CON(R6,R7), CH=N—OR6, CH=NR6, OR6, SR6, SOR6, $SO_2R6$, COOR6, $CH_2N$(R6, R7), N(R6,R7), lower (C1-C4) alkyl, alkenyl, or alkynyl;

or a pharmaceutically acceptable salt, ester or prodrug thereof.

The compound can have the structure of Formula (If)

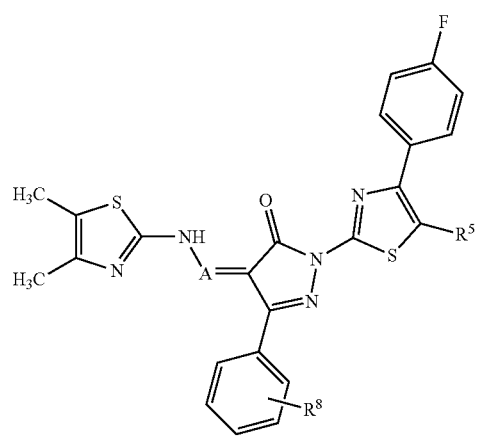

(If)

wherein R8 is F, $CF_3$, Cl, Br, I, OH, SH, $CF_3$, $NO_2$, $SO_4H$, $SO_2NH_2$, $NHNH_2$, $ONH_2$, NHC=(O)$NHNH_2$, NHC=(O)$NH_2$, NHC=(O)H, NHC(O)—OH, NHOH, $OCF_3$, $OCHF_2$, R6, COOH, COOR6, CHO, CN, $NH_2$, NHR6, $NHCONH_2$, NHCONHR6, NHCOR6, $NHSO_2R6$, OCR6, COR6, $CH_2R6$, CON(R6,R7), CH=N—OR6, CH=NR6, OR6, SR6, SOR6, $SO_2R6$, COOR6, $CH_2N$(R6, R7), N(R6,R7), lower (C1-C4) alkyl, alkenyl, or alkynyl;

or a pharmaceutically acceptable salt, ester or prodrug thereof.

The invention also provides a pharmaceutical composition comprising a pharmaceutically acceptable carrier and a compound; and a compound, where the compound has the structure selected from the group consisting of:

Gav1-021

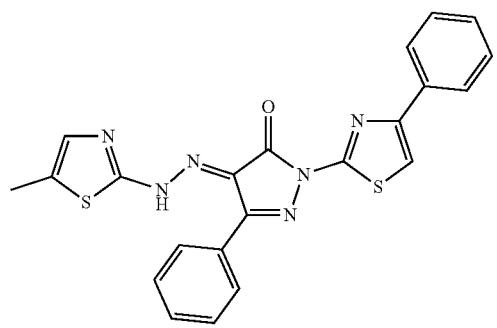

,

Gav1-023

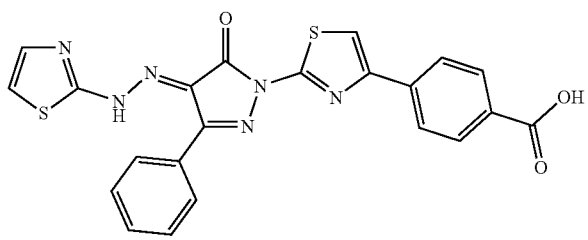

,

-continued
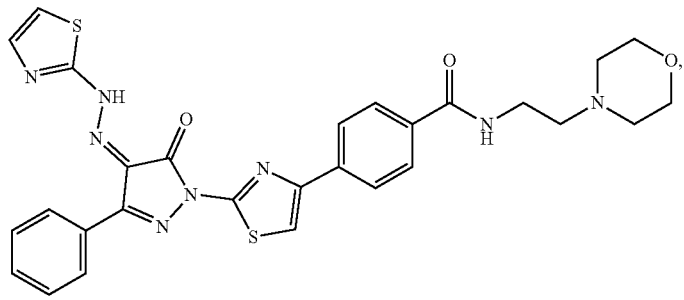
Gav1-036
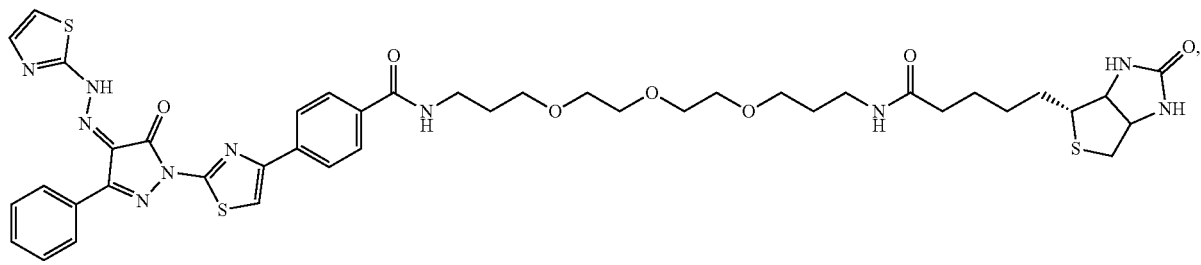
Gav1-028
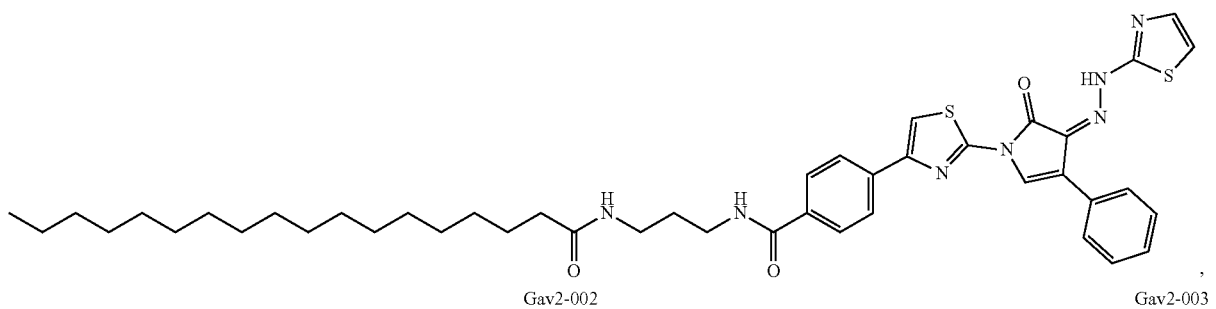
Gav1-037
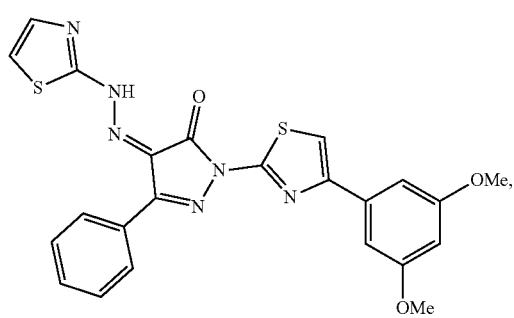
Gav2-002
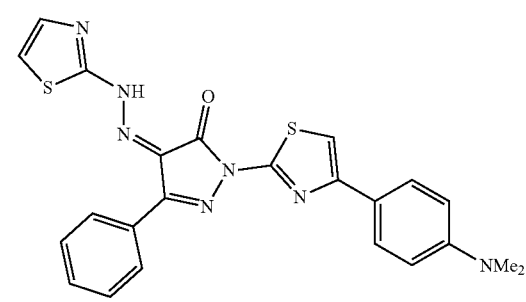
Gav2-003
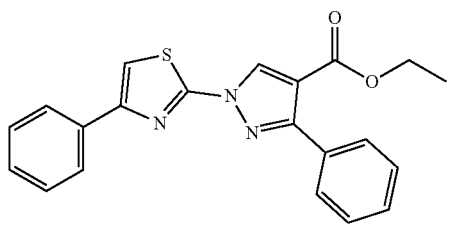
Gav2-004
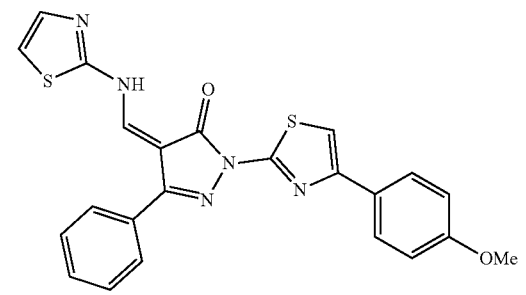
Gav2-005

-continued
Gav2-006
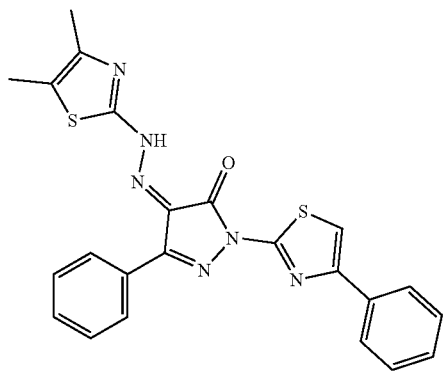
Gav2-007
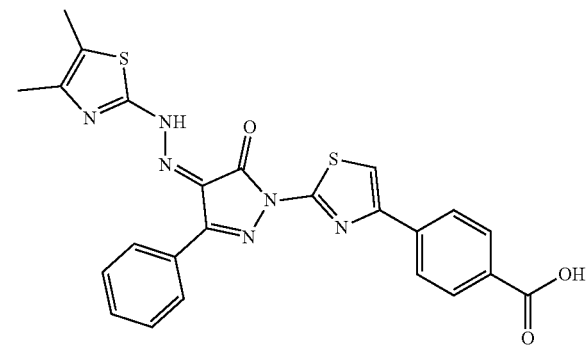
Gav2-008
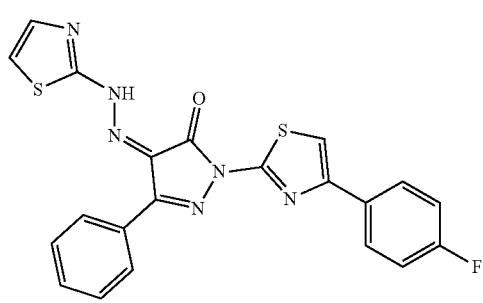
Gav2-009
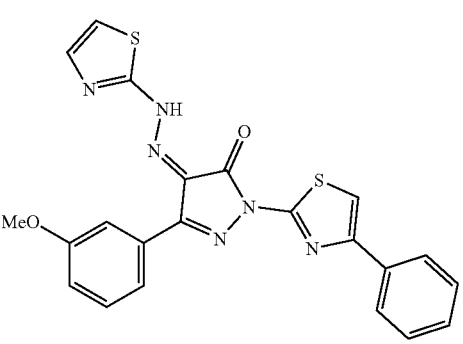
Gav2-010
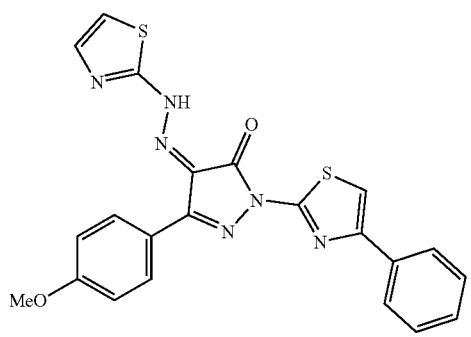
Gav2-011
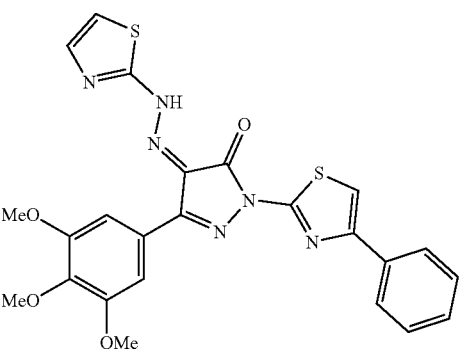
Gav2-012
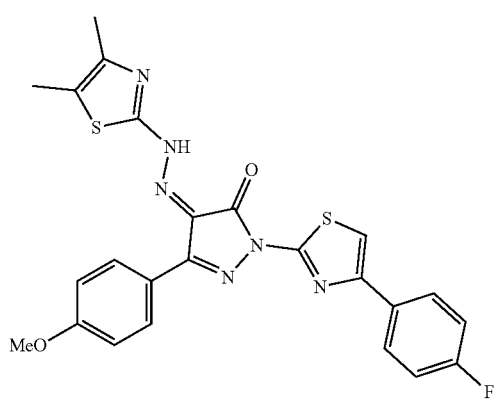
Gav2-013
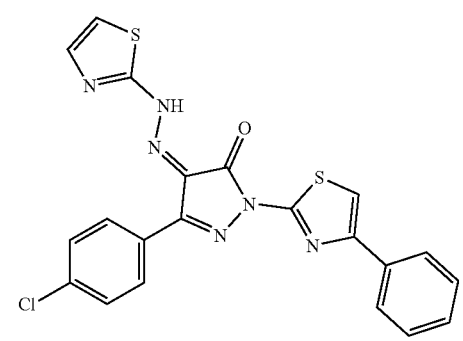

-continued
Gav2-014
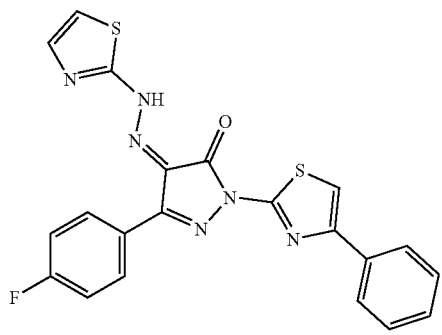
Gav2-015
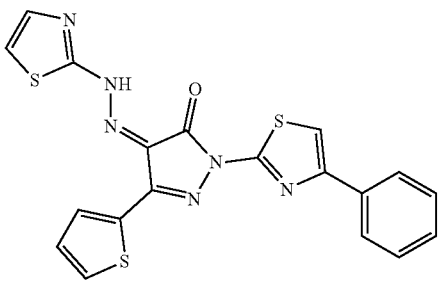
Gav2-016
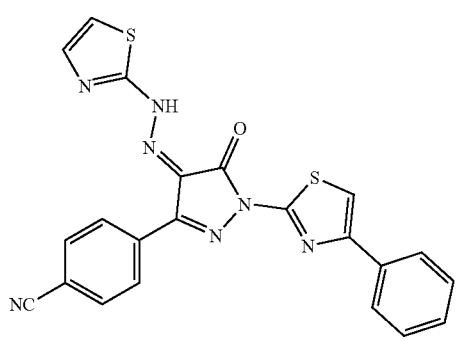
Gav2-017
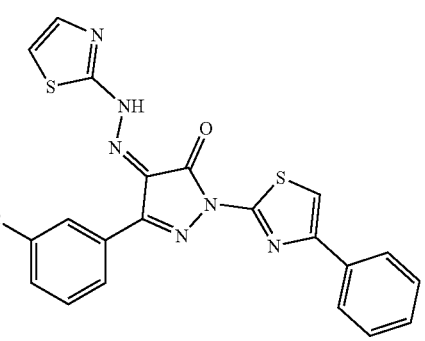
Gav2-018
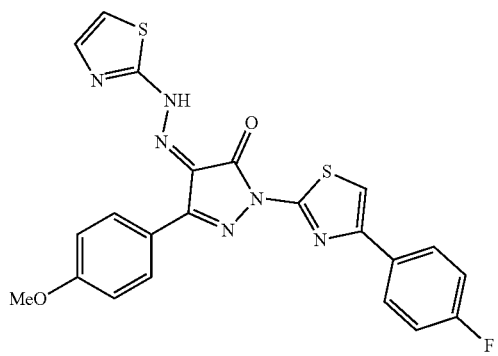
Gav2-019
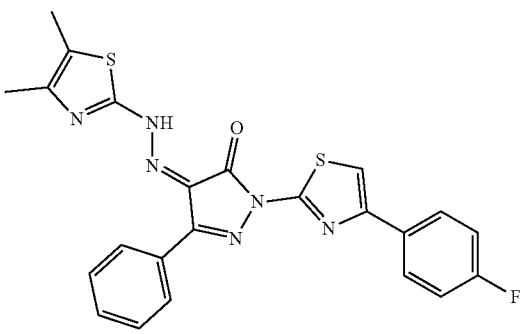
Gav2-020
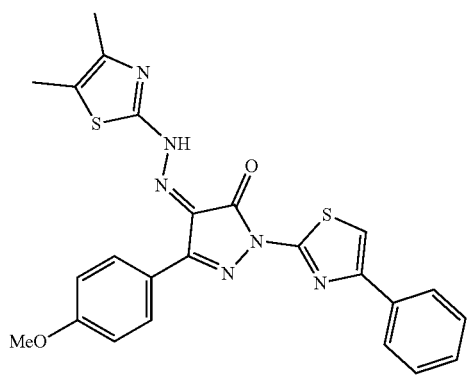
Gav2-021
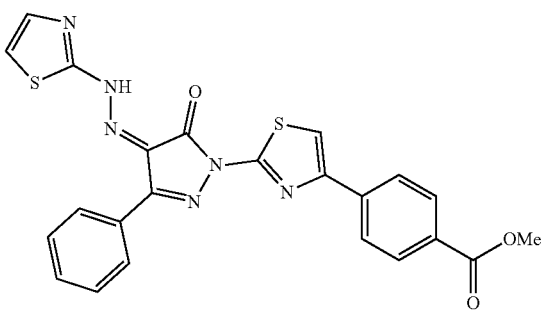

-continued
Gav2-022
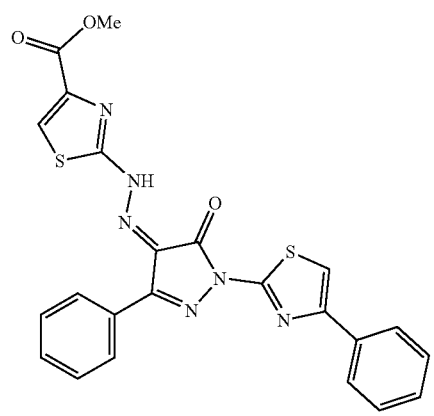
Gav2-023
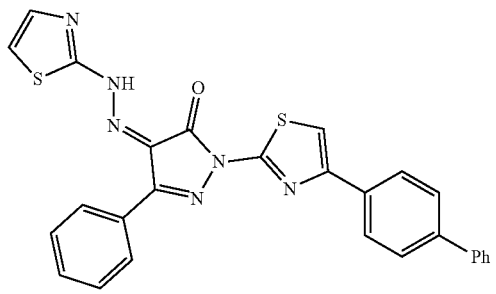
Gav2-024
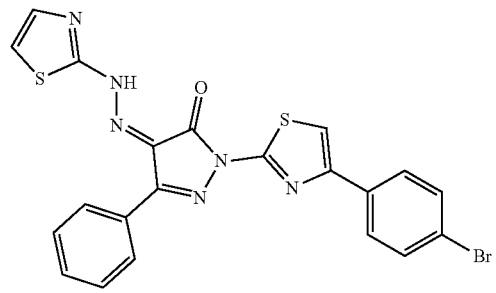
Gav2-025
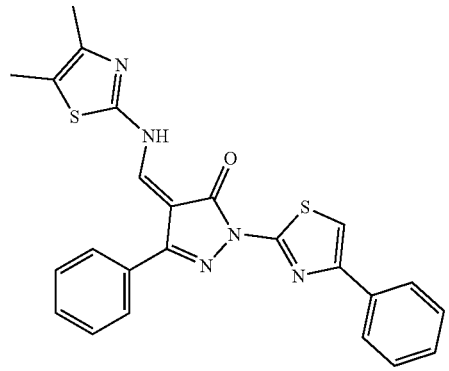
Gav2-026
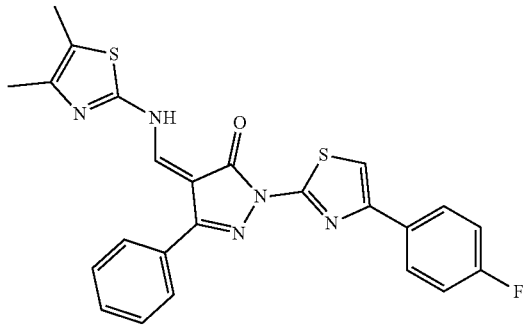
Gav2-027
Gav2-028
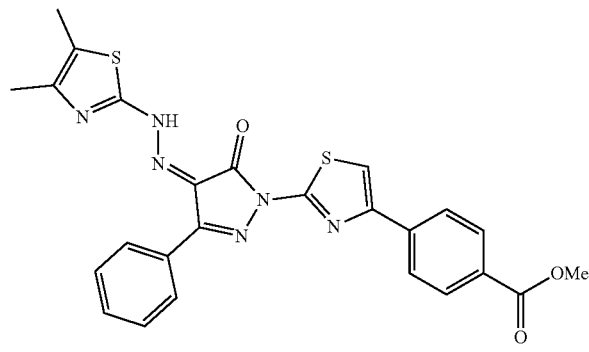
Gav2-031
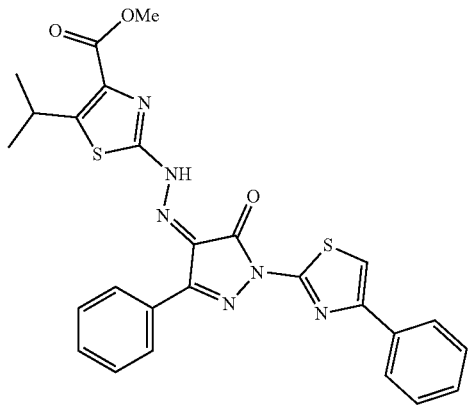

-continued
Gav2-032
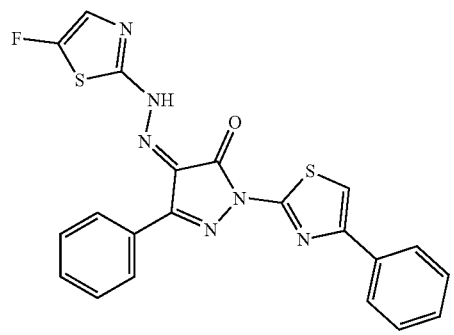
Gav2-033
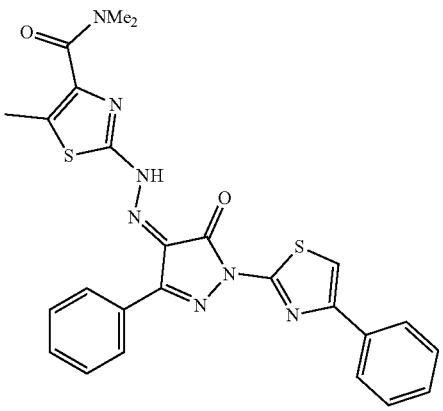
Gav2-034
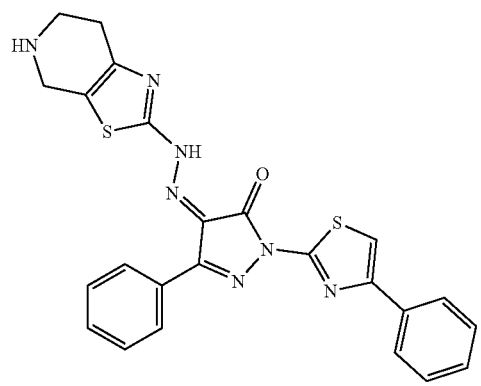
Gav-1-034
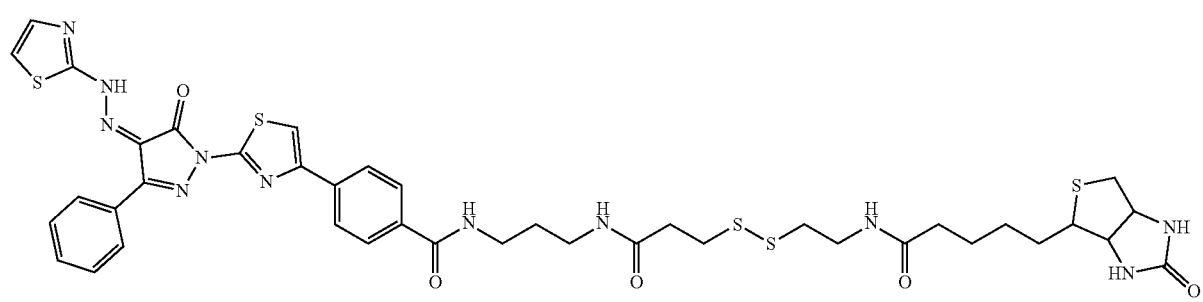
Gav-1-040
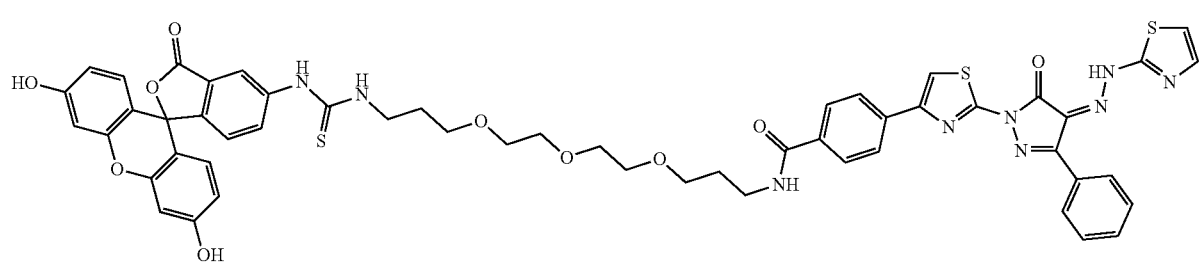

21
-continued
22
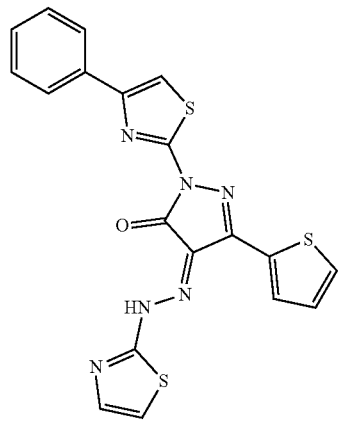 , 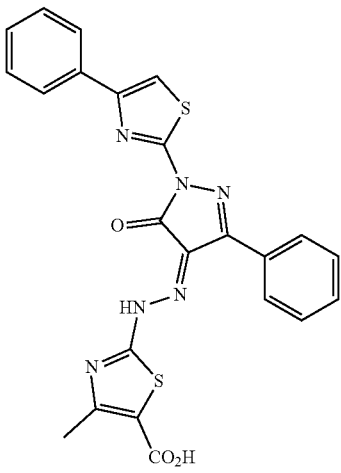 , 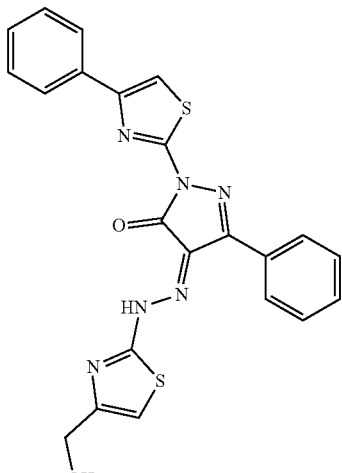 ,
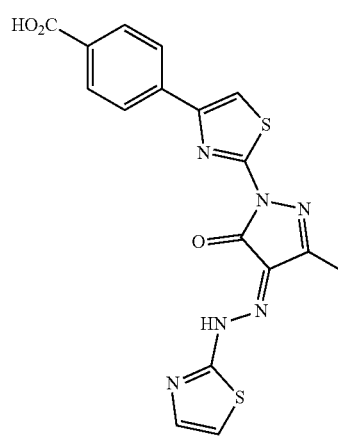 , 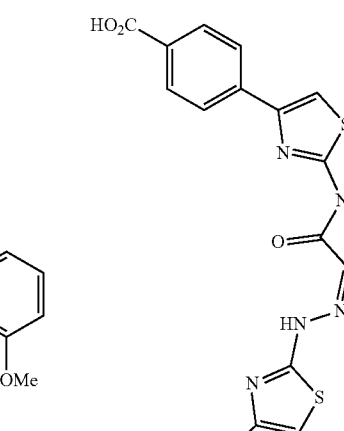 ,
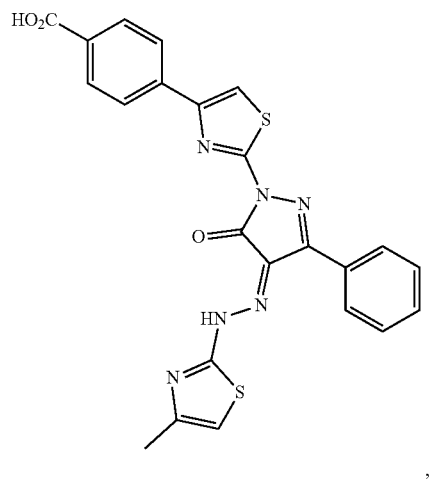 , 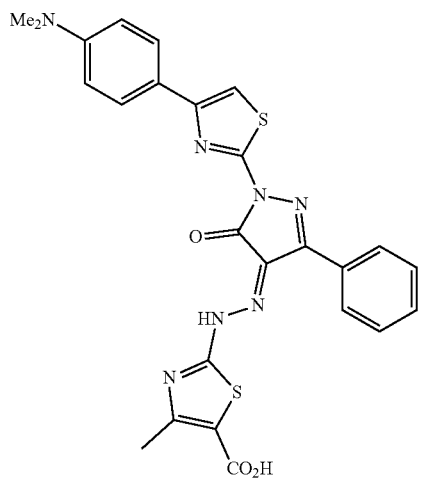 ,

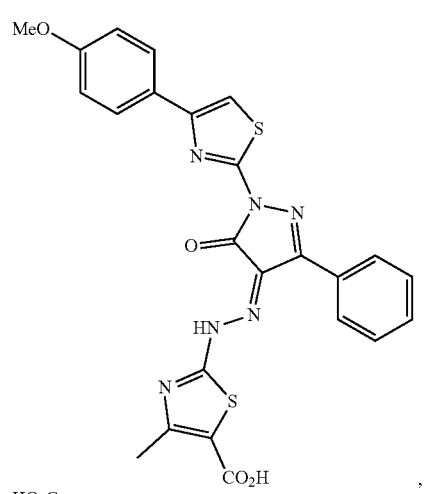
,
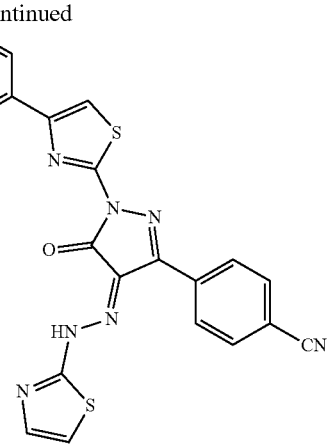
,
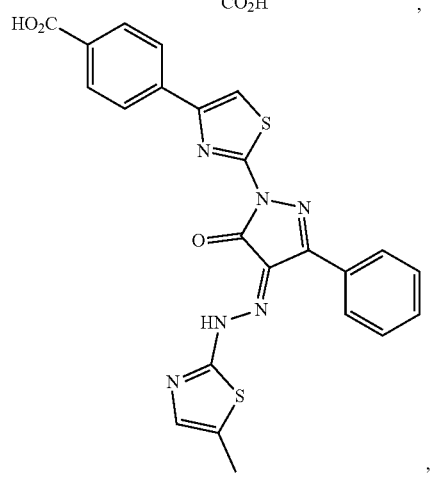
,
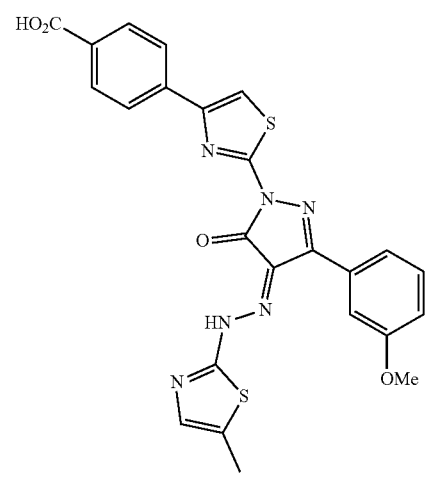
,
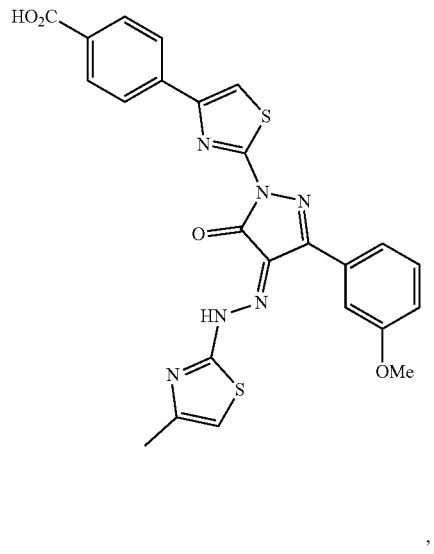
,
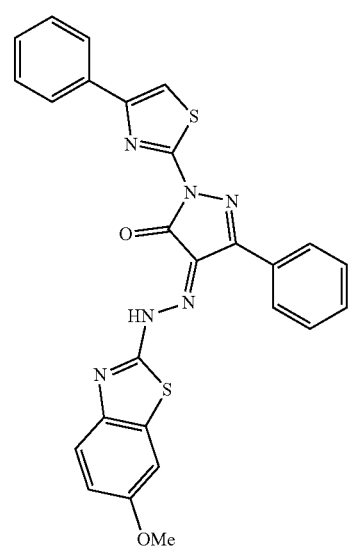
,
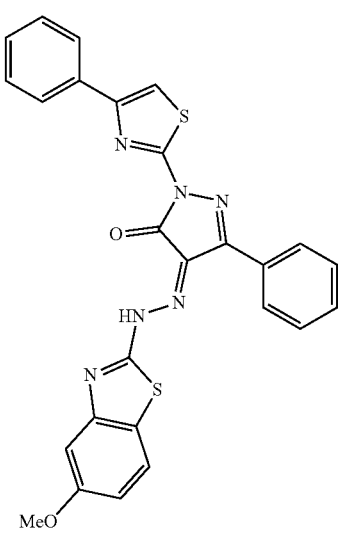
, -continued
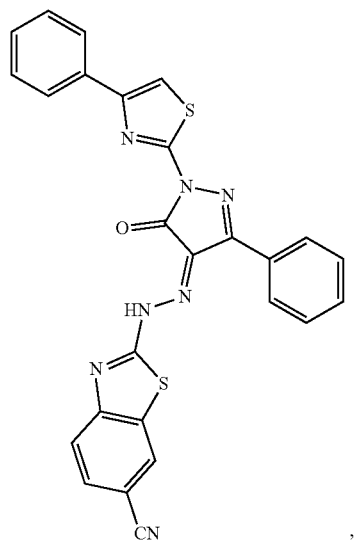 , 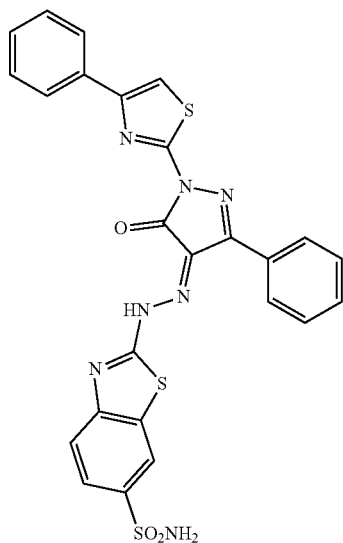 , 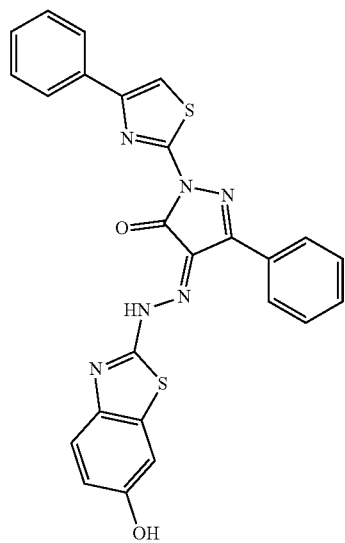 ,
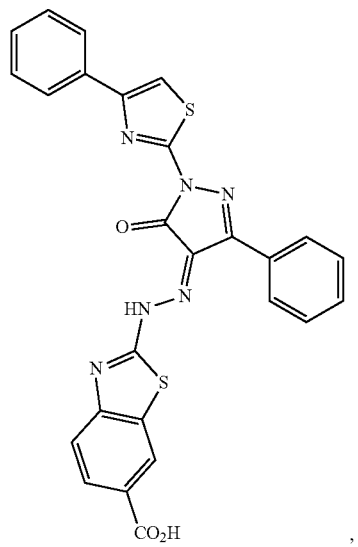 , 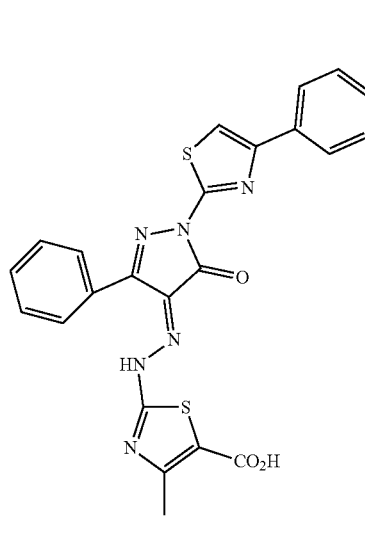 , 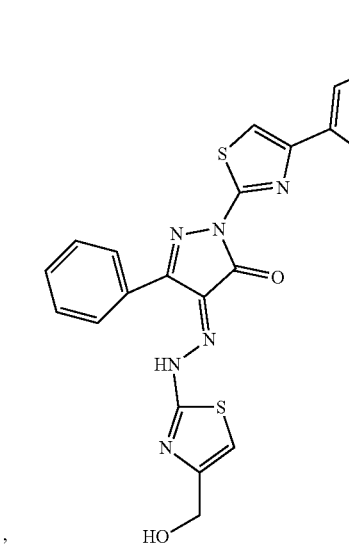 ,
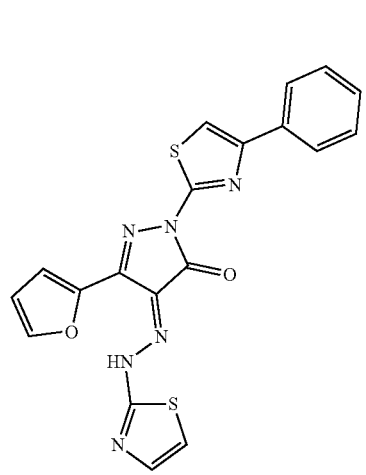 , 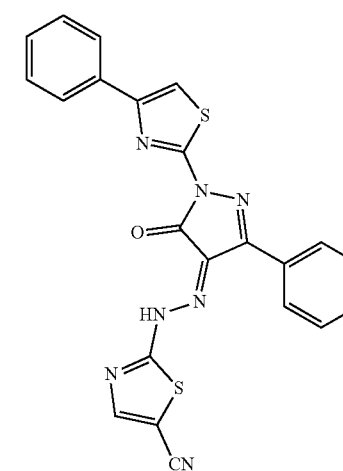 , 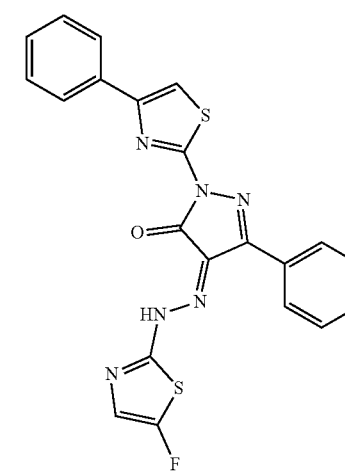 , -continued
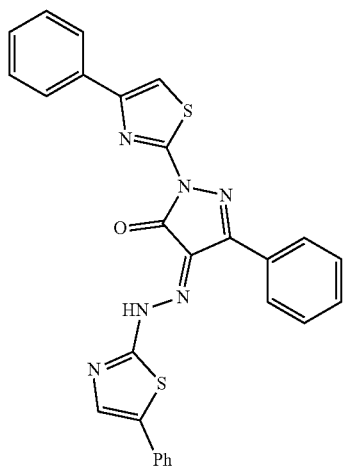
,
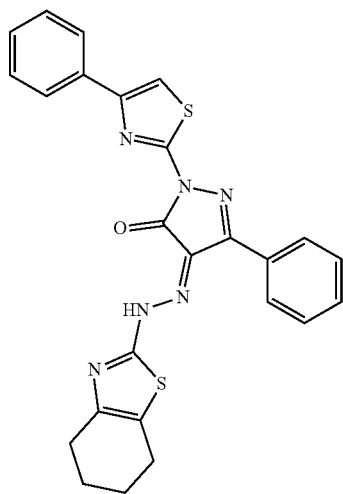
,
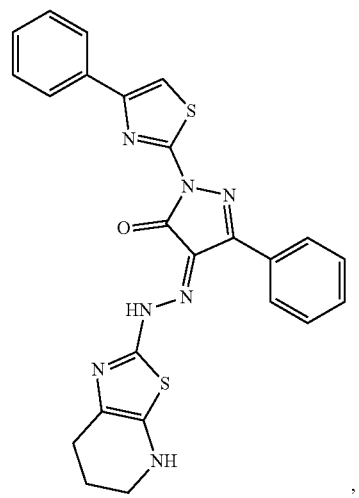
,
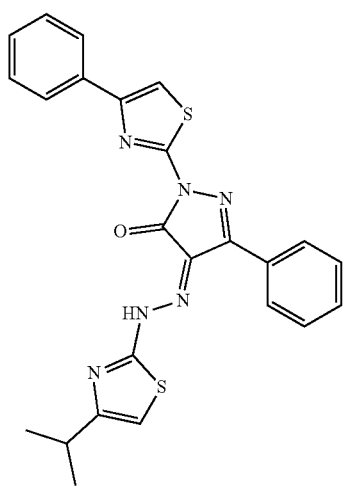
,
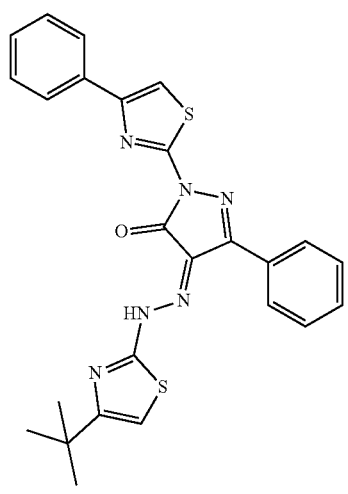
,
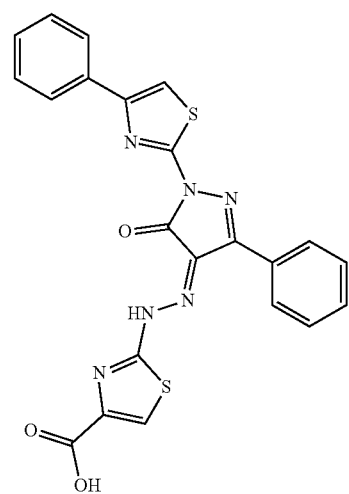
,
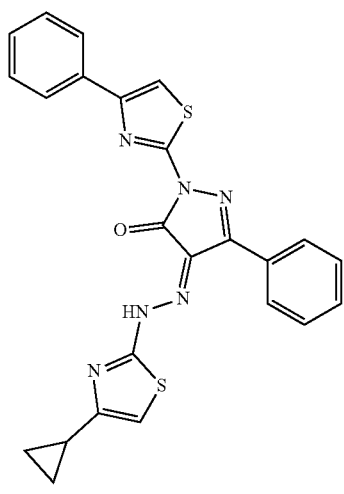
,
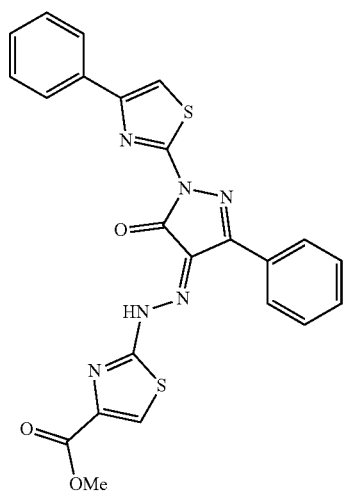
,
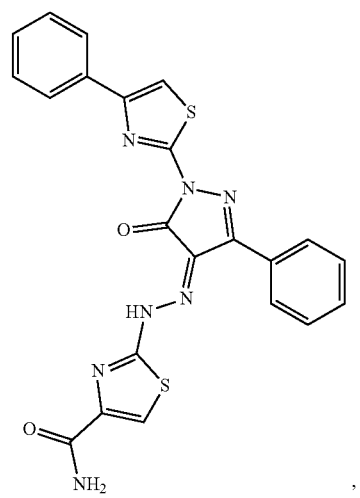
, -continued
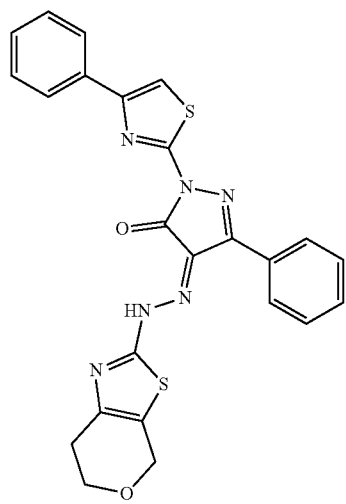 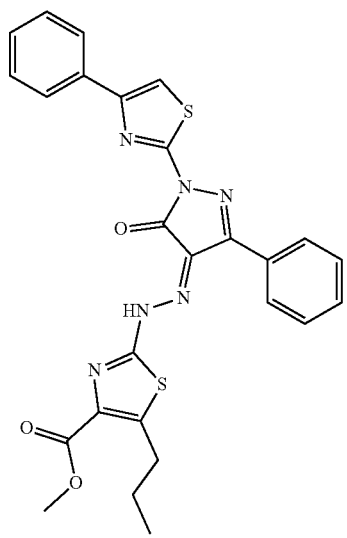 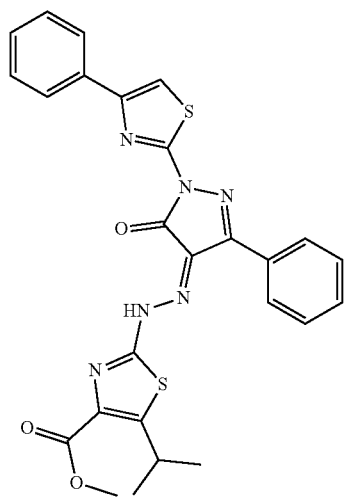
,
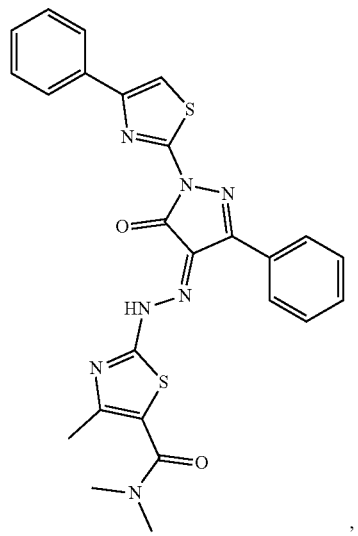 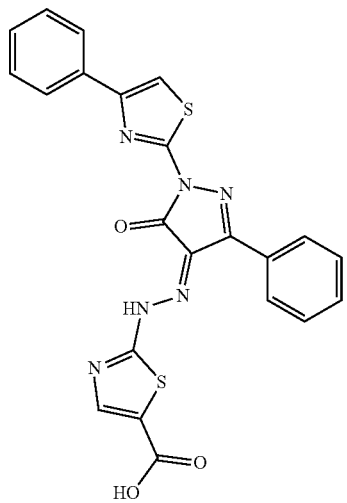 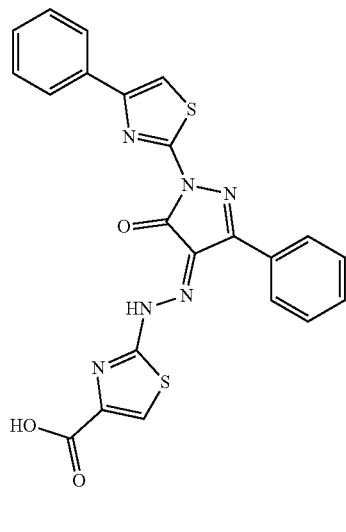
,
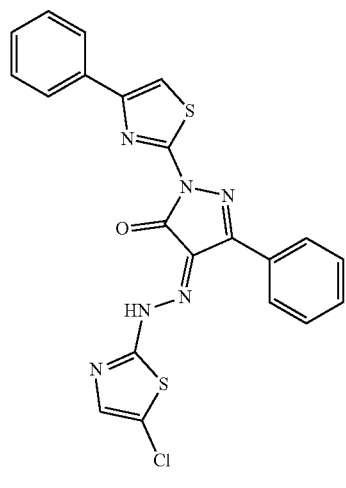 and 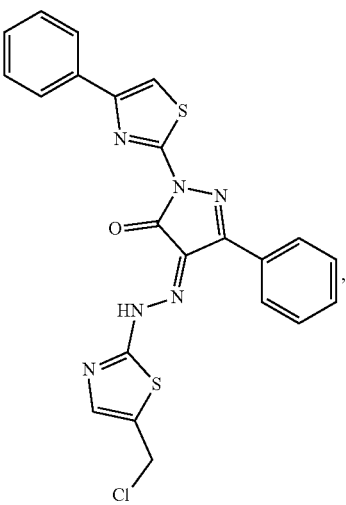
, -continued
Gav1-001
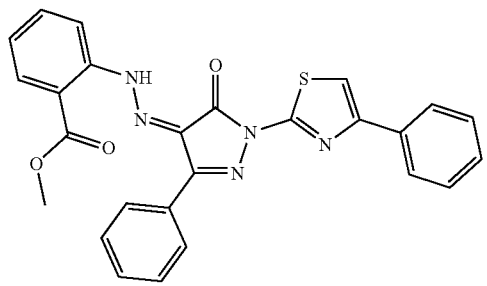
Gav1-002
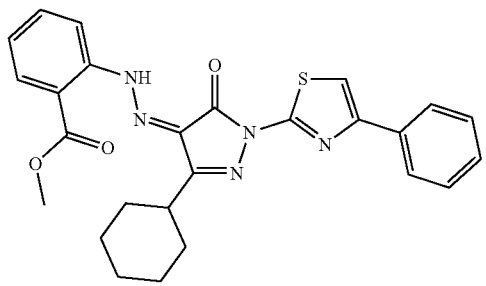
Gav1-003
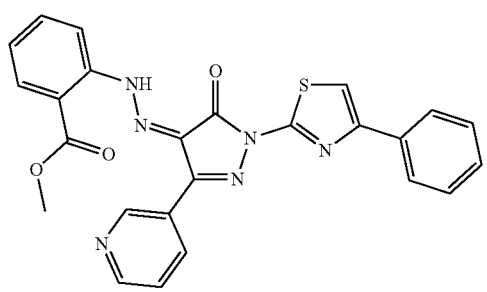
Gav1-004
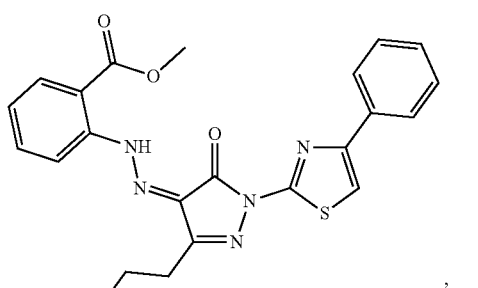
Gav1-005
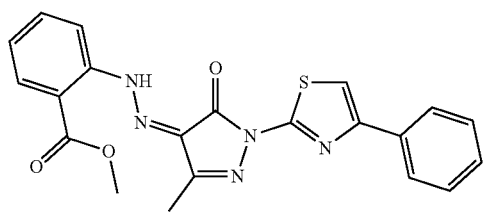
Gav1-010
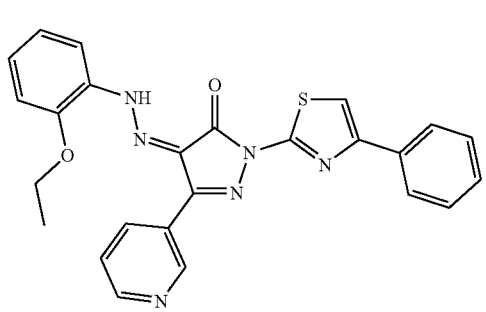
Gav1-020
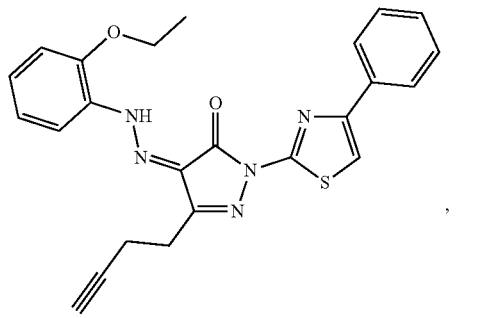
Gav1-024
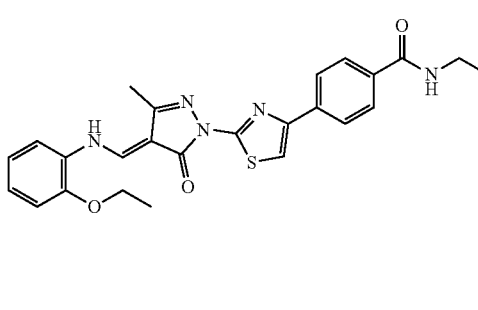
Gav1-025
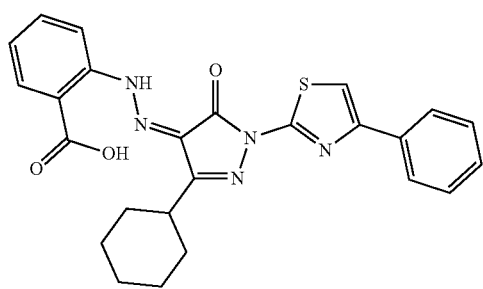
Gav1-026
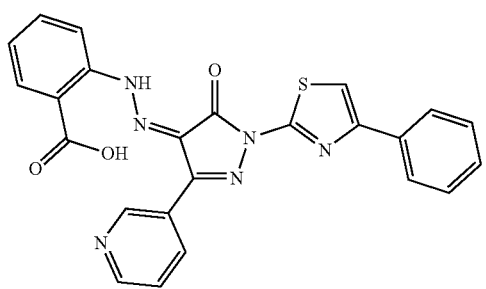

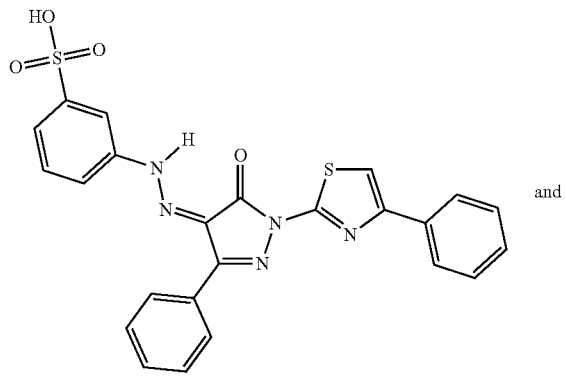
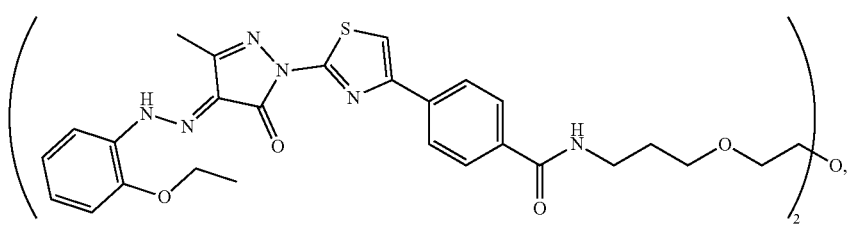
or a pharmaceutically acceptable salt, ester or prodrug thereof.
Also provided are prodrug compounds of BAX activators selected from the group consisting of
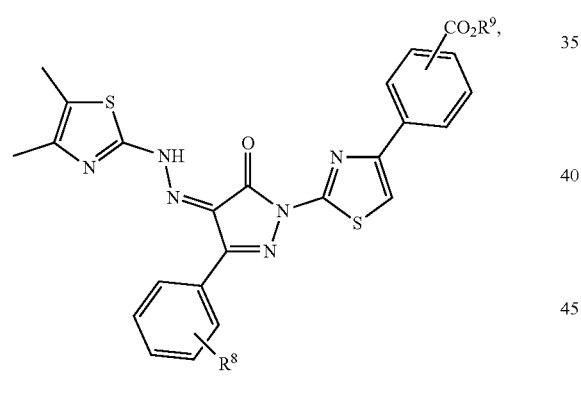
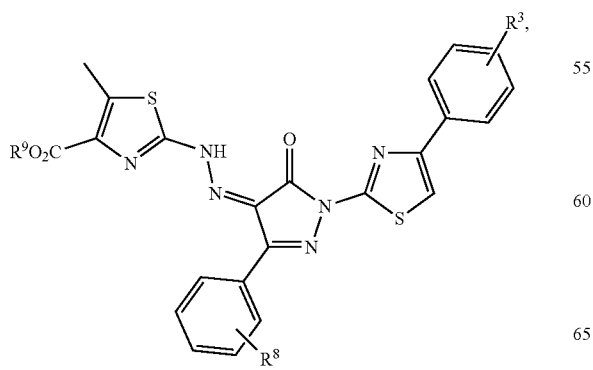
-continued
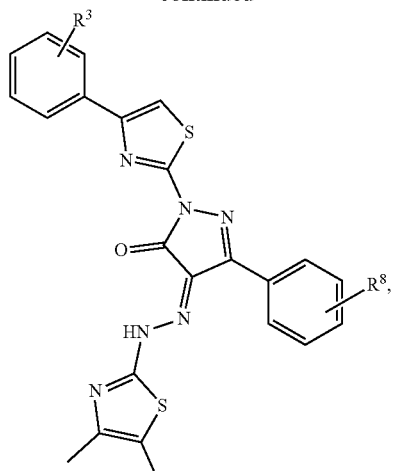
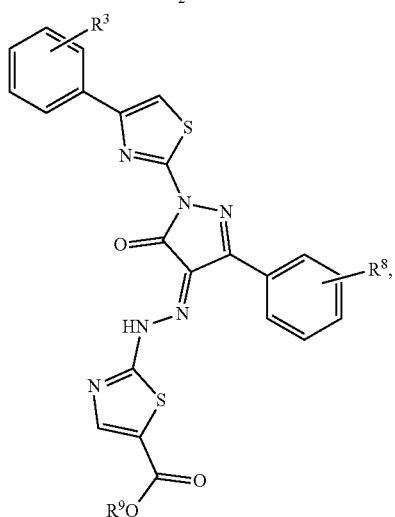

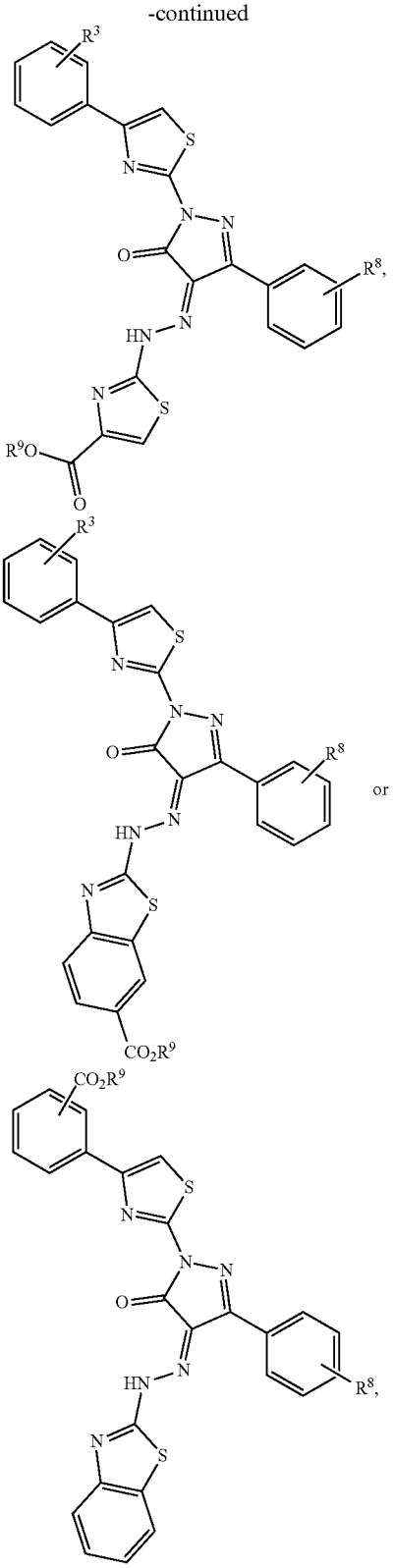

wherein

R3 is H, F, Cl, Br, I, OH, SH, CF$_3$, NO$_2$, R6, COOH, COOR6, CHO, CN, NH$_2$, SO$_4$H, SO$_2$NH$_2$, NHNH$_2$, ONH$_2$, NHC=(O)NHNH$_2$, NHC=(O)NH$_2$, NHC=(O)H, NHC(O)—OH, NHOH, OCF$_3$, OCHF$_2$, NHR6, NHCONH$_2$, NHCONHR6, NHCOR6, NHSO$_2$R6, OR6, OCR6, COR6, CH$_2$R6, CON(R6,R7), CH=N—OR6, CH=NR6, OR6, SR6, SOR6, SO$_2$R6, COOR6, CH$_2$N(R6, R7), N(R6,R7), lower (C1-C4) alkyl, alkenyl, or alkynyl;

R6 and R7 are independently H, C1-C6 alkyl, C1-C6 haloalkyl, C3-C6 cycloalkyl, C1-C6 alkoxy, C1-C6 haloalkoxy, C1-C6 thioalkoxy, or C1-C6 thiolhaloalkoxy;

R8 is F, CF$_3$, Cl, Br, I, OH, SH, CF$_3$, NO$_2$, SO$_4$H, SO$_2$NH$_2$, NHNH$_2$, ONH$_2$, NHC=(O)NHNH$_2$, NHC=(O)NH$_2$, NHC=(O)H, NHC(O)—OH, NHOH, OCF$_3$, OCHF$_2$, R6, COOH, COOR6, CHO, CN, NH$_2$, NHR6, NHCONH$_2$, NHCONHR6, NHCOR6, NHSO$_2$R6, OCR6, COR6, CH$_2$R6, CON(R6,R7), CH=N—OR6, CH=NR6, OR6, SR6, SOR6, SO$_2$R6, COOR6, CH$_2$N(R6, R7), N(R6,R7), lower (C1-C4) alkyl, alkenyl, or alkynyl;

R9 is H, CH$_3$, CH$_2$CH$_3$, CH$_2$CH$_2$CH$_3$, CH—(CH$_3$)$_2$, C—(CH$_3$)$_3$;

or a pharmaceutically acceptable salt thereof.

Preferably, the compound is present in the pharmaceutical composition in an amount effective to activate BCL-2-associated X-protein (BAX). Preferably, the compound activates cytosolic BAX and/or mitochondrial BAX. In one embodiment, wherein the compound specifically targets the N-terminal activation site of BAX with nanomolar affinity.

In different embodiments, one or more of R1, R2 and R3 is not H, or two or more of R1, R2 and R3 are not H, or all of R1, R2 and R3 are not H.

In different embodiments, the compound has the proviso that the compound is not one or more of 1H-Pyrazole-4,5-dione, 3-phenyl-1-(4-phenyl-2-thiazolyl)-, 4-[2-(2-thiazolyl)hydrazone], 1H-Pyrazole-4,5-dione, 3-methyl-1-(4-phenyl-2-thiazolyl)-, 4-[(4-phenyl-2-thiazolyl)hydrazone], 1H-Pyrazole-4,5-dione, 3-methyl-1-(4-phenyl-2-thiazolyl)-, 4-[(4-phenyl-2-thiazolyl)hydrazone] (9Cl), 1H-Pyrazole-4,5-dione, 1-[4-(4-methoxyphenyl)-2-thiazolyl]-3-phenyl-, 4-[2-(2-thiazolyl)hydrazone], 1H-Pyrazole-4,5-dione, 3-methyl-1-(4-phenyl-2-thiazolyl)-, 4-[[4-(4-methylphenyl)-2-thiazolyl]hydrazone], 1H-Pyrazole-4,5-dione, 3-methyl-1-(4-phenyl-2-thiazolyl)-, 4-[[4-(4-methylphenyl)-2-thiazolyl]hydrazone] (9Cl), 1H-Pyrazole-4,5-dione, 3-methyl-1-[4-(4-methylphenyl)-2-thiazolyl]-, 4-[2-(4-phenyl-2-thiazolyl)hydrazone], 1H-Pyrazole-4,5-dione, 3-methyl-1-[4-(4-methylphenyl)-2-thiazolyl]-, 4-(2-thiazolylhydrazone), 1H-Pyrazole-4,5-dione, 3-methyl-1-[4-(4-methylphenyl)-2-thiazolyl]-, 4-(2-thiazolylhydrazone) (9Cl), 1H-Pyrazole-4,5-dione, 3-methyl-1-[4-(4-methylphenyl)-2-thiazolyl]-, 4-[2-[4-(4-methylphenyl)-2-thiazolyl]hydrazone], 1H-Pyrazole-4,5-dione, 3-methyl-1-(4-phenyl-2-thiazolyl)-, 4-(2-thiazolylhydrazone), 1H-Pyrazole-4,5-dione, 3-methyl-1-(4-phenyl-2-thiazolyl)-, 4-(2-thiazolylhydrazone), 1H-Pyrazole-4,5-dione, 1-[4-(4-chlorophenyl)-2-thiazolyl]-3-methyl-, 4-[(4-phenyl-2-thiazolyl)hydrazone] (9Cl), 1H-Pyrazole-4,5-dione, 1-[4-(4-chlorophenyl)-2-thiazolyl]-3-methyl-, 4-[(4-phenyl-2-thiazolyl)hydrazone] (9Cl), 1H-Pyrazole-4,5-dione, 3-methyl-1-(4-phenyl-2-thiazolyl)-, 4-[2-[4-(4-methoxyphenyl)-2-thiazolyl]hydrazone], 1H-Pyrazole-4,5-dione, 3-methyl-1-(4-phenyl-2-thiazolyl)-, 4-[2-[4-(4-chlorophenyl)-2-thiazolyl]hydrazone], 1H-Pyrazole-4,5-dione, 1-[4-(4-methoxyphenyl)-2-thiazolyl]-3-methyl-, 4-[2-(4-phenyl-2-thiazolyl)hydrazone], 1H-Pyrazole-4,5-dione, 3-methyl-1-(4-phenyl-2-thiazolyl)-, 4-[2-[4-(4-bromophenyl)-2-thiazolyl]hydrazone], 1H-Pyrazole-4,5-dione, 3-methyl-1-[4-(4-methylphenyl)-2-thiazolyl]-, 4-[2-[4-(4-chlorophenyl)-2-thiazolyl]hydrazone], 1H-Pyrazole-4,5-dione, 3-methyl-1-[4-(4-methylphenyl)-2-thiazolyl]-, 4-[2-[4-(4-bromophenyl)-2-thiazolyl]hydrazone], 1H-Pyrazole- 4,5-dione, 1-[4-(4-chlorophenyl)-2-thiazolyl]-3-methyl-, 4-[2-[4-(4-methylphenyl)-2-thiazolyl]hydrazone], 1H-Pyrazole-4,5-dione, 1-[4-(4-bromophenyl)-2-thiazolyl]-3-methyl-, 4-[2-[4-(4-methylphenyl)-2-thiazolyl]hydrazone], 1H-Pyrazole-4,5-dione, 3-methyl-1-[4-(4-methylphenyl)-2-thiazolyl]-, 4-[2-[4-(4-methoxyphenyl)-2-thiazolyl]hydrazone], 1H-Pyrazole-4,5-dione, 1-[4-(4-methoxyphenyl)-2-thiazolyl]-3-methyl-, 4-[2-[4-(4-methylphenyl)-2-thiazolyl]hydrazone], 1H-Pyrazole-4,5-dione, 3-methyl-1-(5-methyl-4-phenyl-2-thiazolyl)-, 4-[2-(5-methyl-2-thiazolyl)hydrazone], 1H-Pyrazole-4,5-dione, 1-[4-(4-bromophenyl)-2-thiazolyl]-3-methyl-, 4-(2-thiazolylhydrazone), 1H-Pyrazole-4,5-dione, 1-[4-(4-bromophenyl)-2-thiazolyl]-3-methyl-, 4-(2-thiazolylhydrazone) (9Cl), 1H-Pyrazole-4,5-dione, 3-methyl-1-(4-phenyl-2-thiazolyl)-, 4-(2-benzothiazolylhydrazone), 1H-Pyrazole-4,5-dione, 3-methyl-1-(4-phenyl-2-thiazolyl)-, 4-(2-benzothiazolylhydrazone) (9Cl), 1H-Pyrazole-4,5-dione, 1-[4-(4-methoxyphenyl)-2-thiazolyl]-3-methyl-, 4-(2-thiazolylhydrazone), 1H-Pyrazole-4,5-dione, 1-[4-(4-methoxyphenyl)-2-thiazolyl]-3-methyl-, 4-(2-thiazolylhydrazone) (9Cl), 1H-Pyrazole-4,5-dione, 3-methyl-1-[4-(4-methylphenyl)-2-thiazolyl]-, 4-(2-benzothiazolylhydrazone), 1H-Pyrazole-4,5-dione, 3-methyl-1-[4-(4-methylphenyl)-2-thiazolyl]-, 4-(2-benzothiazolylhydrazone) (9Cl), 1H-Pyrazole-4,5-dione, 1-[4-(4-chlorophenyl)-2-thiazolyl]-3-methyl-, 4-[2-(2-thiazolyl)hydrazone], 1H-Pyrazole-4,5-dione, 1-[4-(4-methoxyphenyl)-2-thiazolyl]-3-methyl-, 4-[2-[4-(4-methoxyphenyl)-2-thiazolyl]hydrazone], 1H-Pyrazole-4,5-dione, 1-[4-(4-bromophenyl)-2-thiazolyl]-3-methyl-, 4-[2-[4-(4-bromophenyl)-2-thiazolyl]hydrazone], 1H-Pyrazole-4,5-dione, 1-[4-(4-chlorophenyl)-2-thiazolyl]-3-methyl-, 4-[2-[4-(4-chlorophenyl)-2-thiazolyl]hydrazone], 1H-Pyrazole-4,5-dione, 1-[4-(4-bromophenyl)-2-thiazolyl]-3-methyl-, 4-[2-[4-(4-chlorophenyl)-2-thiazolyl]hydrazone], 1H-Pyrazole-4,5-dione, 1-[4-(4-chlorophenyl)-2-thiazolyl]-3-methyl-4-[2-[4-(4-bromophenyl)-2-thiazolyl]hydrazone], 1H-Pyrazole-4,5-dione, 3-methyl-1-(4-phenyl-2-thiazolyl)-, 4-[2-[4-(3-nitrophenyl)-2-thiazolyl]hydrazone], 1H-Pyrazole-4,5-dione, 3-methyl-1-[4-(4-methylphenyl)-2-thiazolyl]-, 4-[2-[4-(4-nitrophenyl)-2-thiazolyl]hydrazone], 1H-Pyrazole-4,5-dione, 3-methyl-1-(4-phenyl-2-thiazolyl)-, 4-[2-(5-phenyl-1H-pyrazol-3-yl)hydrazone], 1H-Pyrazole-4,5-dione, 1-[4-(4-chlorophenyl)-2-thiazolyl]-3-methyl-, 4-[2-[4-(4-methoxyphenyl)-2-thiazolyl]hydrazone], 1H-Pyrazole-4,5-dione, 1-[4-(4-methoxyphenyl)-2-thiazolyl]-3-methyl-, 4-[2-[4-(4-chlorophenyl)-2-thiazolyl]hydrazone], 1H-Pyrazole-4,5-dione, 1-[4-(4-bromophenyl)-2-thiazolyl]-3-methyl-, 4-[2-[4-(4-methoxyphenyl)-2-thiazolyl]hydrazone], 1H-Pyrazole-4,5-dione, 1-[4-(4-methoxyphenyl)-2-thiazolyl]-3-methyl-, 4-[2-[4-(4-bromophenyl)-2-thiazolyl]hydrazone], 1H-Pyrazole-4,5-dione, 3-methyl-1-[4-(3-nitrophenyl)-2-thiazolyl]-, 4-[2-[4-(4-methylphenyl)-2-thiazolyl]hydrazone], 1H-Pyrazole-4,5-dione, 3-methyl-1-[4-(3-nitrophenyl)-2-thiazolyl]-, 4-[2-[4-(3-nitrophenyl)-2-thiazolyl]hydrazone], 1H-Pyrazole-4,5-dione, 3-phenyl-1-(4-phenyl-2-thiazolyl)-, 4-(2-benzothiazolylhydrazone), 1H-Pyrazole-4,5-dione, 3-phenyl-1-(4-phenyl-2-thiazolyl)-, 4-(2-benzothiazolylhydrazone) (9Cl), 1H-Pyrazole-4,5-dione, 1-[4-(4-methoxyphenyl)-2-thiazolyl]-3-phenyl-, 4-(2-benzothiazolylhydrazone), and 1H-Pyrazole-4,5-dione, 1-[4-(4-methoxyphenyl)-2-thiazolyl]-3-phenyl-, 4-(2-benzothiazolylhydrazone) (9Cl).

Pharmaceutically acceptable salts that can be used with compounds of the present invention are non-toxic salts derived, for example, from inorganic or organic acids including, but not limited to, salts derived from hydrochloric, sulfuric, phosphoric, acetic, lactic, fumaric, succinic, tartaric, gluconic, citric, methanesulphonic and p-toluenesulphonic acids.

Esters of the compounds can include, for example, an alkyl ester (e.g., $C_1$-$C_3$ alkyl, or $C_3$-$C_6$ alkyl, or $C_3$-$C_6$ branched alkyl, e.g., t-butyl, isopropyl, isobutyl), ester groups derived from aliphatic carboxylic acids, formates, acetates, propionates, butyrates, acrylates and ethylsuccinates.

Prodrugs of the compounds can include, for example, mono-, di-, or triphosphate prodrugs, peptidyl derivatives, succinates, phosphate esters, acetates, and carbonyl groups, carbamate prodrugs, and carbonate prodrugs. Various forms of prodrugs are known in the art. See, for Bundgaard, (ed.), Design of Prodrugs, Elsevier (1985), Krogsgaard-Larsen, et al., (ed). Design and Application of Prodrugs, Textbook of Drug Design and Development (1991); and Higuchi and Stella (eds.) Prodrugs as Novel Drug Delivery Systems, American Chemical Society (1975), the contents of which are herein incorporated by reference.

Also provided is a pharmaceutical composition comprising any of the compounds disclosed herein and a pharmaceutically acceptable carrier. The term "carrier" is used in accordance with its art-understood meaning, to refer to a material that is included in a pharmaceutical composition but does not abrogate the biological activity of pharmaceutically active agent(s) that are also included within the composition. Typically, carriers have very low toxicity to the animal to which such compositions are to be administered. In some embodiments, carriers are inert. Pharmaceutically acceptable carriers and diluents that can be used herewith encompasses any of the standard pharmaceutical carriers or diluents, such as, for example, a sterile isotonic saline, phosphate buffered saline solution, water, and emulsions, such as an oil/water or water/oil emulsions.

Also provided is a medicament for treating cancer comprising any of the compounds disclosed herein or any of the pharmaceutical compositions disclosed herein, wherein the compound is in an amount effective to activate BCL-2-associated X-protein (BAX).

Also provided is a method of treating a cancer in a subject comprising administering to the subject any of the compounds disclosed herein in an amount effective to activate BCL-2-associated X-protein (BAX) in a subject.

The invention also provides a method of treating a cancer in a subject comprising administering to the subject an activator of BCL-2-associated X-protein (BAX) in combination with an inhibitor of BCL-2 or with an inhibitor of BCL-xL and BCL-2, in an amount effective to treat a cancer in a subject.

As used herein, to "treat" or "treating" a cancer means to reduce or eliminate the cancer in a subject, or to reduce the further spread of cancer in the subject, or to reduce or eliminate a sign or symptom of the cancer in the subject. In terms of tumors, "treat" a tumor means to eradicate the tumor, to reduce the size of the tumor, to stabilize the tumor so that it does not increase in size, or to reduce the further growth of the tumor. Treatment of the cancer can be achieved, for example, by inducing apoptosis in cancer cells and/or in leukemia stem cells.

The invention also provides a method of inducing apoptosis in cancer cells and/or in leukemia stem cells in a subject comprising administering any of the BAX activators disclosed herein to the subject in an amount effective to induce apoptosis in cancer cells and/or in leukemia stem cells in a subject.

The cancer can be, for example, a leukemia or a solid tumor. The cancer can be, for example, acute lymphoblastic leukemia (ALL), acute myeloid leukemia (AML), chronic lymphocytic leukemia (CLL) or chronic myeloid leukemia (CML).

The cancer can be, for example, one or more of breast cancer, prostate cancer, lymphoma, skin cancer, pancreatic cancer, colon cancer, melanoma, malignant melanoma, ovarian cancer, brain or spinal cord cancer, primary brain carcinoma, medulloblastoma, neuroblastoma, glioma, head-neck cancer, glioma, glioblastoma, liver cancer, bladder cancer, stomach cancer, kidney cancer, placental cancer, cancer of the gastrointestinal tract, non-small cell lung cancer (NSCLC), head or neck carcinoma, breast carcinoma, endocrine cancer, eye cancer, genitourinary cancer, cancer of the vulva, ovary, uterus or cervix, hematopoietic cancer, myeloma, leukemia, lymphoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, chronic granulocytic leukemia, acute granulocytic leukemia, acute myelogenous leukemia, chronic myelogenous leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft tissue cancer, soft-tissue sarcoma, osteogenic sarcoma, sarcoma, primary macroglobulinemia, central nervous system cancer and retinoblastoma.

The cancer cells can be, for example, leukemia cells, solid tumor cells, non-small cell lung cancer (NSCLC) cells, colon cancer cells, central nervous system cancer cells, melanoma cells, ovarian cancer cells, renal cancer cells, prostate cancer cells, or breast cancer cells. The cancer cells can be, for example, acute lymphoblastic leukemia (ALL), acute myeloid leukemia (AML), chronic lymphocytic leukemia (CLL) or chronic myeloid leukemia (CML) cells. The cancer cells can include, for example, tumor cells, neoplastic cells, malignant cells, metastatic cells, and hyperplastic cells.

The activator of BAX can be, for example, any of the BAX activators disclosed herein, for example, Gav2-006, Gav2-008 or Gav2-010. The inhibitor of BCL-2 can be, for example, ABT-199 or ABT-263. The inhibitor of BCL-2 and BCL-xL can be, for example, ABT-263.

ABT-199 is also known as venetoclax or as 4-(4-{[2-(4-Chlorophenyl)-4,4-dimethyl-1-cyclohexen-1-yl]methyl}-1-piperazinyl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide. ABT-263 is also known as navitoclax or as 4-(4-{[2-(4-Chlorophenyl)-5,5-dimethyl-1-cyclohexen-1-yl]methyl}-1-piperazinyl)-N-[(4-{[(2R)-4-(4-morpholinyl)-1-(phenylsulfanyl)-2-butanyl]amino}-3-[(trifluoromethyl)sulfonyl]phenyl)sulfonyl]benzamide.

Preferably, the combination of the activator of BAX with the inhibitor of BCL-2 or the inhibitor of BCL-xL and BCL-2 induces apoptosis in cancer cells and/or in leukemia stem cells. Preferably, the combination of the activator of BAX with the inhibitor of BCL-2 or the inhibitor of BCL-xL and BCL-2 results in a synergistic treatment effect. Preferably, the combination of the activator of BAX with the inhibitor of BCL-2 or the inhibitor of BCL-xL and BCL-2 allows a treatment effect to be achieved at a lower dose of the inhibitor than in the absence of the BAX activator.

Preferably, the BAX activator activates BCL-2-associated X-protein (BAX) and does not induce apoptosis in healthy tissue. Preferably, the BAX activator activates cytosolic BAX.

The compounds disclosed herein can in some embodiments be administered to the subject in combination with one or more additional therapeutic agents and/or in combination with, for example, radiation therapies, ultrasound, and/or surgical interventions. Additional therapeutic agents include, for example, agents that induce apoptosis; polynucleotides (e.g., anti-sense, ribozymes, siRNA); polypeptides (e.g., enzymes and antibodies); biological mimetics; agents that bind to and inhibit anti-apoptotic proteins (e.g., agents that inhibit anti-apoptotic BCL-2 proteins); alkaloids; alkylating agents; antitumor antibiotics; antimetabolites; hormones; platinum compounds; monoclonal or polyclonal antibodies (e.g., antibodies conjugated with anticancer drugs, toxins, defensins, etc.), toxins, radionuclides; biological response modifiers (e.g., interferons (e.g., IFN-.alpha., etc.) and interleukins (e.g., IL-2, etc.), etc.); adoptive immunotherapy agents; hematopoietic growth factors; agents that induce tumor cell differentiation (e.g., all-trans-retinoic acid, etc.); gene therapy reagents (e.g., antisense therapy reagents and nucleotides); tumor vaccines; angiogenesis inhibitors; proteosome inhibitors: NF kappa beta modulators; anti-CDK compounds; and HDAC inhibitors. Agents that induce apoptosis include, for example, radiation (e.g., X-rays, gamma rays, UV); kinase inhibitors (e.g., Epidermal Growth Factor Receptor (EGFR) kinase inhibitor, Vascular Growth Factor Receptor (VGFR) kinase inhibitor, Fibroblast Growth Factor Receptor (FGFR) kinase inhibitor, Platelet-derived Growth Factor Receptor (PDGFR) kinase inhibitor, and Bcr-Abl kinase inhibitors such as GLEEVEC); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; and staurosporine.

Preferably, for any of the methods or compounds disclosed here, the compound or BAX activator specifically targets the N-terminal activation site of BAX with nanomolar affinity, i.e. with an affinity <1,000 nanomolar.

As used herein, "BAX" is BCL-2-associated X-protein. In an embodiment, the BAX is mammalian. In a preferred embodiment, the BAX is a human BAX. In an embodiment, the human BAX has or comprises consecutive amino acid residues having the following sequence:

(SEQ ID NO: 1)
MDGSGEQPRGGGPTSSEQIMKTGALLLQGFIQDRAGRMGGEAPELALD

PVPQDASTKKLSECLKRIGDELDSNMELQRMIAAVDTDSPREVFFRVA

ADMFSDGNFNWGRVVALFYFASKLVLKALCTKVPELIRTIMGWTLDFL

RERLLGWIQDQGGWDGLLSYFGTPTWQTVTIFVAGVLTASLTIWKKMG.

Human BCL-2 alpha isoform has or comprises the following sequence. This isoform has been selected as the canonical sequence for the BCL-2 protein.

(SEQ ID NO: 2)
MAHAGRTGYDNREIVMKYIHYKLSQRGYEWDAGDVGAAPPGAAPAPGI

FSSQPGHTPHPAASRDPVARTSPLQTPAAPGAAAGPALSPVPPVVHLT

LRQAGDDFSRRYRRDFAEMSSQLHLTPFTARGRFATVVEELFRDGVNW

GRIVAFFEFGGVMCVESVNREMSPLVDNIALWMTEYLNRHLHTWIQDN

GGWDAFVELYGPSMRPLFDFSWLSLKTLLSLALVGACITLGAYLGHK.

Human BCL-2 beta isoform has or comprises the following sequence:

(SEQ ID NO: 3)
MAHAGRTGYDNREIVMKYIHYKLSQRGYEWDAGDVGAAPPGAAPAPGI

FSSQPGHTPHPAASRDPVARTSPLQTPAAPGAAAGPALSPVPPVVHLT

LRQAGDDFSRRYRRDFAEMSSQLHLTPFTARGRFATVVEELFRDGVNW

GRIVAFFEFGGVMCVESVNREMSPLVDNIALWMTEYLNRHLHTWIQDN

GGWVGALGDVSLG.

Human BCL-xL alpha isoform has or comprises the following sequence:

(SEQ ID NO: 4)
MSQSNRELVVDFLSYKLSQKGYSWSQFSDVEENRTEAPEGTESEMETP

SAINGNPSWHLADSPAVNGATGHSSSLDAREVIPMAAVKQALREAGDE

FELRYRRAFSDLTSQLHITPGTAYQSFEQVVNELFRDGVNWGRIVAFF

SFGGALCVESVDKEMQVLVSRIAAWMATYLNDHLEPWIQENGGWDTFV

ELYGNNAAAESRKGQERFNRWFLTGMTVAGVVLLGSLFSRK.

Human BCL-xL beta isoform has or comprises the following sequence:

(SEQ ID NO: 5)
MSQSNRELVVDFLSYKLSQKGYSWSQFSDVEENRTEAPEGTESEMETP

SAINGNPSWHLADSPAVNGATGHSSSLDAREVIPMAAVKQALREAGDE

FELRYRRAFSDLTSQLHITPGTAYQSFEQVVNELFRDGVNWGRIVAFF

SFGGALCVESVDKEMQVLVSRIAAWMATYLNDHLEPWIQENGGWVRTK

PLVCPFSLASGQRSPTALLLYLFLLCWVIVGDVDS.

The BAX dimer structure reveals a dimerization interface that includes the interaction of two structural surfaces critical for the activation of BAX; the N-terminal trigger site from one BAX protomer and a C-terminal surface from the second BAX protomer that includes the C-terminal α9 helix. The BAX dimer conformation is inactive and resistant to activation compared to monomeric BAX indicating that the BAX dimer may form an autoinhibited conformation. BAX activation requires disruption of the BAX dimer conformation.

In an embodiment, the compounds described herein are administered in the form of a composition comprising the compound and a carrier. The compounds and compositions of the present invention can be administered to subjects using routes of administration known in the art. The administration can be systemic or localized to a specific site. Routes of administration include, but are not limited to, intravenous, intramuscular, intrathecal or subcutaneous injection, transdermal, oral or rectal administration, and injection into a specific site.

All combinations of the various elements described herein, including all subsets, are within the scope of the invention unless otherwise indicated herein or otherwise clearly contradicted by context. Where a numerical range is provided herein for any parameter, it is understood that all numerical subsets of that numerical range, and all the individual integer values contained therein, are provided as part of the invention. Thus, C1-C6 alkyl includes, for example, the subset of alkyls which are 1-3 carbon atoms, the subset of alkyls which are 2-5 carbon atoms etc. as well as an alkyl which has 1 carbon atom, an alkyl which has 3 carbon atoms, an alkyl which has 6 carbon atom, etc.

The subject can be any mammal, such a mouse, a rat, a cat, a dog, a horse, a sheep, a cow, a steer, a bull, livestock, a primate, a monkey, and is preferably a human.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

It was hypothesized that induction of apoptosis by mimicking the BAX-activating interactions of select BH3 domains to deploy BAX offers the possibility of a new anti-cancer strategy. Toward this end, the understanding of the precise regulatory mechanisms of pro-apoptotic BAX has dramatically evolved in recent years and details of the activation mechanism of BAX by BH3-only proteins such as BIM, BID and PUMA have been elucidated (Czabotar et al., 2013; Gavathiotis et al., 2008; Kim et al., 2009; Llambi et al., 2011; Lovell et al., 2008).

Small molecules were sought that activate BAX through interaction with the N-terminal activation site (trigger site) of BAX (Gavathiotis et al., 2008; Gavathiotis et al., 2010). This unique binding site compared to the canonical BH3 grooves of BAX, BAK and anti-apoptotic BCL-2 proteins may provide a BAX-selective targeting strategy. Previously, an in silico docking screen was used to target the trigger site of BAX and identify a BAX activator molecule 7 (BAM7), which induces activation of BAX in vitro, albeit, at relatively weak potency (Gavathiotis et al., 2012; Walensky et al. 2016). The efficacy in cancer models in vitro and in vivo was undetermined and given that BAX is expressed in cancer cells as well as normal cells the specificity and therapeutic window for targeting BAX in cancer remains unknown. To identify the therapeutic potential and utility for clinical application of BAX activators in cancer, compounds with potency, selectivity and drug-like properties needed to be developed.

Here, a potent and selective BAX activator with drug-like properties, BAX trigger site activator 1 (BTSA1) (also known as BAM38) is described. BTSA1 induces activation of soluble (cytosolic) BAX leading to prompt and robust mitochondrial apoptosis in several leukemia cell lines despite overexpression of the anti-apoptotic BCL-2 proteins. BTSA1 is effective in killing patient leukemia blasts and stem cell-enriched populations, without affecting healthy counterparts. Mechanistic studies demonstrate that BAX expression levels and cytosolic conformation regulate cellular response to BTSA1. Moreover, BTSA1 exhibits potent efficacy in vivo in a preclinical human AML leukemia model while sparing cells of the hematopoietic system and healthy tissues. Finally, BTSA1 demonstrates remarkable synergy with venetoclax in killing leukemia cells demonstrating its utility in combination with other BCL-2 family drugs. The data present the therapeutic potential of BTSA1 and indicate direct BAX activation through the BAX trigger site as a novel therapeutic strategy.

Materials and Methods

Compounds.

Hydrocarbon-stapled peptides corresponding to the BH3 domain of BIM, Ac-BIM SAHB$_{A2}$: N-acetylated EIWIAQELRS5IGDS$_5$FNAYYA-CONH$_2$ (SEQ ID NO:6) and FITC-BIM SAHB$_{A2}$: FITC-βAla-EIWIAQELRS$_5$IGDS$_5$FNAYYA-CONH$_2$ (SEQ ID NO:7), where S5 represents the non-natural amino acid inserted for olefin metathesis, were synthesized, purified at >95% purity by CPC Scientific Inc. and characterized as previously described (Gavathiotis et al., 2008). BTSA2 compound was obtained from Scientific Exchange, Inc. (cat. #X-013360). BAX channel blocker was obtained from EMD Millipore (cat. #196805). Chemical synthesis procedures and analytical characterization for BTSA1 and biotinylated BTSA1 is provided in Supplemental Experimental Procedures. Compounds were >95% pure, reconstituted in 100% DMSO and diluted in aqueous buffers or cell culture medium for assays.

Production of Recombinant Proteins.

Human, recombinant and tagless BAX, BCL-xLΔC, MCL-1ΔNΔC, BFL-1/A1ΔC were expressed in *Escherichia coli* and purified as previously reported (Gavathiotis et al, 2012; Uchime et al., 2016). BAX wild type and mutant monomers were purified by size exclusion chromatography in a buffer containing 20 mM HEPES pH 7.2, 150 mM KCl, 1 mM DTT. BCL-XLΔC, MCL-1ΔNΔC, and BFL-1/A1ΔC monomeric proteins were purified by size exclusion chromatography in a buffer containing 50 mM Tris pH 7.4, 150 mM NaCl, 1 mM DTT. Superdex 75 10/300 GL and 200 10/300 GL (GE Healthcare) columns were used.

Fluorescence Polarization Binding Assays.

Fluorescence polarization assays (FPA) were performed as previously described (Gavathiotis et al., 2012). Firstly, direct binding isotherms were generated by incubating FITC-BIM SAHB$_{A2}$ (50 nM) with serial dilutions of full-length BAX, BCL-XLΔC, MCL-1ΔNΔC, BFL-1/A1ΔC and fluorescence polarization was measured at 20 minutes on a F200 PRO microplate reader (TECAN). Subsequently, in competition assays, a serial dilution of small molecule or acetylated BIM SAHB$_{A2}$ (Ac-BIM SAHB) was combined with FITC-BIM SAHBA2 (50 nM), followed by the addition of recombinant protein at ~EC75 concentration, as determined by the direct binding assay (BAX: 500 nM; BCL-XLΔC, MCL-1ΔNΔC, BFL-1/A1ΔC: 200 nM). Fluorescence polarization was measured at 20 minutes and IC$_{50}$ values calculated by nonlinear regression analysis of competitive binding curves using Prism software (Graphpad).

NMR Samples and Spectroscopy.

The uniformly $^{15}$N-labelled protein samples were prepared by growing the bacteria in minimal medium containing $^{15}$N-labeled NH$_4$Cl followed by the same purification procedure as previously described (Uchime et al., 2016). Protein samples were prepared in 25 mM sodium phosphate, 50 mM NaCl solution at pH 6.0 in 5% D$_2$O. Correlation $^{1}$H—$^{15}$N-HSQC spectra were recorded on $^{15}$N-labelled BAX at 50 μM and titrations up to 100 μM of BTSA1 were performed. NMR spectra were acquired at 25° C. on a Bruker 600 MHz spectrometer equipped with a cryoprobe, processed using Topsin and analyzed with CCPNMR. BAX wild type cross-peak assignments were applied as previously reported (Gavathiotis et al., 2008). The weighted average chemical shift difference Δ(CSP) was calculated as √(ΔδH$^1$) 2+(ΔδN$^{15}$/5)2 in p.p.m. The absence of a bar indicates no chemical shift difference, or the presence of a proline or a residue that is overlapped and not used in the analysis. The significance threshold for backbone amide chemical shift changes (0.01 p.p.m.) was calculated based on the average chemical shift across all residues plus the standard deviation, in accordance with standard methods. Mapping of chemical shifts on BAX structure and structural analysis was performed with PYMOL (Schrodinger, LLC). BAX activation and oligomerization were monitored by $^{1}$H-$^{15}$N-HSQC spectra using BAX at 50 μM and BTSA1 at 100 μM or BIM SAHB$_{42}$ at 100 μM in the presence of NMR buffer plus 0.3% CHAPS to stabilize the oligomeric BAX in solution.

Molecular Docking and Molecular Dynamics.

NMR-guided docking of BTSA1 into the NMR structure of BAX (PDB ID: 2KW7) was performed using GLIDE (Glide, version 6.5, Schrödinger, LLC, New York, N.Y., 2014) with or without constraints based on residues undergoing significant chemical shifts. BTSA1 was converted to 3D all atom structure with LIGPREP (LigPrep, version 3.2, Schrödinger, LLC, New York, N.Y., 2014) and assigned partial charges with EPIK (Epik, version 3.0, Schrödinger, LLC, New York, N.Y., 2014). BTSA1 was docked using the extra precision (XP) docking mode. The lowest-energy docking pose is consistent with the observed NMR-chemical shift perturbation data. The lowest energy structure pose from XP docking was selected for further analysis and subjected to a 10 ns molecular dynamics (MD) simulation using DESMOND (DESMOND, version 3, Schrödinger, LLC, New York, N.Y., 2014). The lowest energy BAX structure from the NMR ensemble (PDB ID: 1F16) was subjected to a 10 ns MD simulation using DESMOND for comparison. MD runs were performed in truncated octahedron SPC water box using OPLS_2005 force field, 300 K and constant pressure of 1.0325 bar. Clustering and analysis of the trajectory was performed with MAESTRO tools (Maestro, version 10.0, Schrödinger, LLC, New York, N.Y., 2014). PYMOL (The PyMOL Molecular Graphics System. Version 1.7; Schrödinger, LLC: New York, 2014) was used for preparing the highlighted poses.

BAX Oligomerization Assay.

The NMR samples started from mixtures of BTSA1-BAX monomer and BIM SAHBA2-BAX monomer as well as a BAX monomer sample were subjected to analysis by size-exclusion chromatography using a SD75 column in 25 mM sodium phosphate and 50 mM NaCl solution at pH 6.0 running buffer. The monomeric and oligomeric BAX fractions elute at ~13.0 min and ~8.5 min, respectively. Protein standards (GE Healthcare) were used to calibrate the molecular weights of gel filtration peaks. Replicates were performed using independent preparations of freshly SEC-purified monomeric BAX protein.

BAX Conformational Change Assay.

The N-terminal conformational change exposing the 6A7 epitope on activated BAX (1 μM) was measured by immunoprecipitation assay in 20 mM Hepes pH 7.2, 150 mM KCl buffer containing increasing doses of BTSA1 for 15 min at room temperature. The mixture was added to 280 µl 3% BSA in PBS and 30 µl of the resulting mixture (10%) was kept for input analysis. The remaining mixture was mixed with 3 µl 6A7 antibody (sc-23959, Santa Cruz) and pre-washed protein A/G beads (Santa Cruz) and incubated for 2 h at 4° C. with rotation. Beads were collected by brief spin, washed three times with 1 mL of 3% BSA buffer, and then solubilized with 25 µl LDS/DTT loading buffer. Samples were resolved by SDS-PAGE electrophoresis and western blot analysis using the BAX N20 antibody (Santa Cruz).

Cell Culture.

HL-60, NB4, THP-1, U937 and HPB-ALL cells were maintained in RPMI 1640 media (Invitrogen) supplemented with 10% FBS, 100 U ml-1 penicillin/streptomycin, 2 mM 1-glutamine, and 50 µM β-mercaptoethanol. OCI-AML3 was maintained in MEM α (Invitrogen) supplemented with 10% FBS, 100 U ml-1 penicillin/streptomycin, 2 mM 1-glutamine and 50 µM β-mercaptoethanol. WT MEFs, BAX/BAK DKO MEFs and BAX KO MEFs were maintained in DMEM (Invitrogen) supplemented with 10% FBS, 100 U ml-1 penicillin/streptomycin, 2 mM 1-glutamine, 0.1 mM MEM nonessential amino acids, and 50 µM β-mercaptoethanol. H9C2 myocytes and 3T3 fibroblasts were maintained in DMEM (Invitrogen) supplemented with 10% FBS, 100 U ml-1 penicillin/streptomycin and 2 mM 1-glutamine.

Western Blotting.

Protein lysates were obtained by cell lysis in Triton X-100 buffer (50 mM Tris-HCL pH 7.40, 150 mM NaCl, 5 mM $MgCl_2$, 1 mM EGTA, 10% Glycerol, 1% Triton X-100 [Sigma]). Protein samples were electrophoretically separated on 4-12% NuPage (Invitrogen) gels, transferred to mobilon-FL PVDF membranes (Millipore) and subjected to immunoblotting. For visualization of proteins with Odyssey Infrared Imaging System (LI-COR Biosciences) membranes were blocked in PBS containing 5% dry milk. Primary antibodies were incubated overnight at 4° C. in a 1:1,000 dilution. After washing, membranes were incubated with an IRdye800-conjugated goat anti-rabbit IgG or IRdye800-conjugated goat anti-mouse IgG secondary antibodies (LI-COR Biosciences) in a 1:5,000 dilution. Proteins were detected with Odyssey Infrared Imaging System.

Western Blot Protein Quantification.

Densitometry of protein bands were acquired using a LI-COR Odyssey® scanner. Quantification and analysis was performed using the Western Analysis tool from the Image Studio 3.1 software.

Isolation of Mitochondria.

Liver from Bak$^{-/-}$ mouse was homogenized in mitochondria isolation buffer [MIB: 250 µM Sucrose, 10 mM Tris-HCl, 0.1 mM EGTA, complete protease inhibitors (Roche Applied Science) by using a Teflon Dounce homogenizer and mitochondria recovered by differential centrifugation at 7000×g for 10 min at 4° C.

BAX Crosslinking.

BAX oligomerization was detected using a crosslinking approach by incubating isolated mitochondria from liver and recombinant BAX protein (200 nM) at indicated doses of BTSA1 with 20× Bismaleimidohexane (BMH, Pierce) for 30 min at RT followed by quenching with 1 mM DTT. Samples were denatured at 95° C. and analyzed by 4-12% NuPage (Invitrogen) gel electrophoresis followed by immunoblotting with anti-BAX antibody (Cell Signaling Cat. 2772).

Pull Down Assay.

OCI-AML3, MEFs and HPB-ALL cytosolic and mitochondrial lysates were generated by Dounce Homogenization. Cells were lysed by Dounce homogenizer in lysis buffer (LB) containing 10 mM Tris, pH 7.5, 1 mM EGTA, 200 mM sucrose plus Complete Protease Inhibitors. The cell lysates were centrifuged at 700×g for 10 min to remove unbroken cells and nuclei. The supernatants were centrifuged at 12000×g for 10 min at 4° C. and the resulting pellet was collected as the mitochondrial fraction and supernatant as the cytosolic fraction. The mitochondrial fraction was resuspended in LB+1% CHAPS to solubilize proteins. In summary, 500 µg of lysates were incubated for 2 hours at room temperature with biotinylated BTSA1 or vehicle. Biotin capture was achieved by incubation with high capacity streptavidin agarose (50 µL 50% slurry/reaction—Pierce) for 1 hour at room temperature. The streptavidin beads were washed (3×) at room temperature with 1×PBS. Cellular BAX bound to the biotinylated-BTSA1 was eluted by boiling for 20 minutes in LDS buffer and then subjected to BAX (2772S, Cell Signaling), BCL-2 (BD Biosciences Cat. 610539), BCL-XL (Cell Signaling Cat. 2764) and MCL-1 (Cell Signaling Cat. 4572) western blot analysis.

Cell Viability Assay.

AML cells ($2 \times 10^4$ cells/well) were seeded in 96-well opaque plates and incubated with serial dilutions of BTSA1 or BTSA1-1 or vehicle (0.15% DMSO) in no FBS media for 2 hours, followed by 10% FBS replacement to a final volume of 100 µl. Cell viability was assayed at 24 hours by addition of CellTiter-Glo reagent according to the manufacturer's protocol (Promega), and luminescence measured using a F200 PRO microplate reader (TECAN). Viability assays were performed in at least triplicate and the data normalized to vehicle-treated control wells. $IC_{50}$ values were determined by nonlinear regression analysis using Prism software (Graphpad). For healthy cells, WT MEFs ($1 \times 10^4$ cells/well), BAX/BAK DKO MEFs ($1 \times 10^4$ cells/well), BAX KO MEFs ($1 \times 10^4$ cells/well), H9C2 ($1 \times 10^4$ cells/well) and 3T3 ($1 \times 10^4$ cells/well) cells (~75%-80% cellular confluence) were seeded in 96-well opaque plates for 18 hours, then cells were treated with serial dilutions of BTSA1 or vehicle (0.15% DMSO) in serum-free growth media for 2 hours followed by serum replacement for a final volume of 100 µl containing 10% FBS. Cell viability was measured at 24 hours or at the indicated time point.

Mitochondrial BAX Translocation Assay.

Intact cells: Cells ($1 \times 10^6$ cells/well) were seeded in 6-well clear bottom plate and incubated with serial dilutions of BTSA1 or vehicle (0.2% DMSO) in media with no FBS in a final volume of 2000 µL. After 2 hours, FBS was supplemented to a final concentration of 10%. Following 4-hour treatment, cells were lysed in 100 µL of digitonin buffer [20 mM Hepes, pH 7.2, 10 mM KCl, 5 mM $MgCl_2$, 1 mM EDTA, 1 mM EGTA, 250 mM sucrose, 0.025% Digitonin (from 5% w/v stock) and complete protease inhibitors (Roche Applied Science)] and incubated on ice for 10 min. The supernatants were isolated by centrifugation at 15,000×g for 10 min and the mitochondrial pellets solubilized in 1% Triton X-100/PBS for 1 h at 4° C. Pellets were solubilized, subjected to a 15,000×rpm spin for 10 min, and 50 ng of protein was mixed with 25 µl LDS/DTT loading buffer. The equivalent fractional volume of the corresponding supernatant samples was mixed with 25 µl LDS/DTT loading buffer. The mitochondrial supernatant and pellet fractions were then separated by 4-12% NuPage (Invitrogen) gels, and analyzed by immunoblotting with anti-BAX antibody (2772S, Cell Signaling).

Isolated Mitochondria:

Mitochondria from liver of WT mice (1 mg/ml) were resuspended in experimental buffer (125 mM KCl, 10 mM Tris-MOPS [pH 7.4], 5 mM glutamate, 2.5 mM malate, 1 mM $K_3PO_4$, 0.1 mM EGTA-Tris [pH 7.4]) and treated with the indicated concentrations of BTSA1 and recombinant BAX protein (200 nM), singly and in combination, and incubated at room temperature for 60 min. The supernatant fractions were isolated by centrifugation at 5500×g for 10 min and the mitochondrial pellets resuspended and washed with 0.1 M sodium carbonate (pH 11.5) for 30 min, centrifuged at 13,000×g for 10 min at 4° C., and then solubilized in 1% Triton X-100/PBS for 1 h at 4° C. Mitochondrial supernatant and pellet fractions were separated by 4-12% NuPage (Invitrogen) gels and analyzed by immunoblotting with anti-BAX antibody (Cell Signaling Cat. 2772).

Mitochondrial Cytochrome c Release Assay.

Intact cells: Cells ($1 \times 10^6$ cells/well) were seeded in 6-well clear bottom plate and incubated with serial dilutions of BTSA1 or vehicle (0.2% DMSO) in RPMI media with no FBS in a final volume of 2000 µL. After 2 hours, FBS was supplemented to a final concentration of 10%. Following 4-hour treatment, cells were lysed in 100 µL of digitonin buffer [20 mM Hepes, pH 7.2, 10 mM KCl, 5 mM $MgCl_2$, 1 mM EDTA, 1 mM EGTA, 250 mM sucrose, 0.025% Digitonin (from 5% w/v stock) and complete protease inhibitors (Roche Applied Science)] and incubated on ice for 10 min. The supernatants were isolated by centrifugation at 15,000×g for 10 min and the mitochondrial pellets solubilized in 1% Triton X-100/PBS for 1 h at 4° C. Pellets were solubilized, subjected to a 15,000×g rpm spin for 10 min, and 50 ng of protein was mixed with 25 µl LDS/DTT loading buffer. The equivalent fractional volume of the corresponding supernatant samples was mixed with 25 µl LDS/DTT loading buffer. The mitochondrial supernatant and pellet fractions were then separated by 4-12% NuPage (Invitrogen) gels, and analyzed by immunoblotting with anti-cytochrome c antibody (BD Biosciences Cat. 556433).

Isolated Mitochondria:

Mitochondria from liver of WT mice (1 mg/ml) were resuspended in experimental buffer (125 mM KCl, 10 mM Tris-MOPS [pH 7.4], 5 mM glutamate, 2.5 mM malate, 1 mM $K_3PO_4$, 0.1 mM EGTA-Tris [pH 7.4]) and treated with the indicated concentrations of BTSA1 and recombinant BAX protein (200 nM), singly and in combination, and incubated at room temperature for 90 min. The supernatants were isolated by centrifugation at 5500×g for 10 min and the mitochondrial pellets solubilized in 1% Triton X-100/PBS. Mitochondrial supernatant and pellet fractions were separated by 4-12% NuPage (Invitrogen) gels and analyzed by immunoblotting with anti-cytochrome c antibody (BD Biosciences Cat. 556433).

Caspase-3/7 Activation Assay.

Cells were treated with BTSA1 as described above for cell viability assays, and caspase-3/7 activation was measured at 6 hours or at the indicated time points by addition of the Caspase-Glo 3/7 chemiluminescence reagent in accordance with the manufacturer's protocol (Promega). Luminescence was detected by a F200 PRO microplate reader (TECAN).

Mitochondrial Depolarization Assay ($mt\Delta\Psi$).

Cells ($3 \times 10^5$ cells/well) were seeded in 6-well clear bottom plate and incubated with serial dilutions of BTSA1 or vehicle (0.2% DMSO) as described for cell viability assays. Following BTSA1 treatment, cells were stained with 100 nM TMRE (Sigma Cat. 87917) for 30 minutes at 37° C. Subsequently, cells were pelleted by centrifugation and resuspended in 1×PBS to eliminate background fluorescence and transfer to a black 96 well plate. Fluorescence intensity was detected by a M100 microplate reader (TECAN, Ex: 540 nm, Em: 579 nm).

Cellular Transfections.

Anti-Apoptotic BCL-2 proteins over-expression: NB4 cells were transfected with human Bcl-2, BCL-xL or MCL-1 using the Amaxa Nucleofector Kit V according to the manufacturer's protocol. Briefly, $3 \times 10^6$ cells were resuspended into Amaxa N solution V with 2 µg human Bcl-2 pCDNA3, human Mcl-1 pCDNA3 or human BCL-xL Kozark start-stop pCDNA3 followed by electroporation using program X-001 of Nucleofector Device. Nucleofected cells ($3 \times 10^6$) were incubated for 48 h before protein extraction and 30 µg protein/sample were separated by 4-12% NuPage (Invitrogen) gels and analyzed by immunoblotting with anti-Bcl-2 (BD Biosciences Cat. 610539), anti-Mcl-1 (Cell Signaling Cat. 4572) or BCL-XL (Cell Signaling Cat. 2764) to evaluate transfection efficiency. For viability experiments, 48 h post-nucleofection, NB4 cells were treated with BTSA1 as described above for cell viability assays. Bax silencing: NB4 cells were transfected with siBAX using the Amaxa Nucleofector Kit V according to the manufacturer's protocol. Briefly, $3 \times 10^6$ cells were resuspended into Amaxa N solution V with 300 nM siBAX s1890 (Invitrogen Cat. 4390824) or 300 nM Select Negative Control No. 2 siRNA (Invitrogen Cat. 4390846) followed by electroporation using program X-001 of Nucleofector Device. Nucleofected cells ($3 \times 10^6$) were incubated for 24 h before protein extraction and 30 µg protein/sample were separated by 4-12% NuPage (Invitrogen) gels and analyzed by immunoblotting with anti-BAX antibody (Cell Signaling Cat. 2772) to evaluate transfection efficiency. For viability experiments, 24 h post-nucleofection, NB4 cells were treated with BTSA1 as described above for cell viability assays.

Pharmacokinetic Analysis.

ICR (CD-1) male mice were fasted at least three hours and water was available ad libitum before the study. Animals were housed in a controlled environment, target conditions: temperature 18 to 29° C., relative humidity 30 to 70%. Temperature and relative humidity was monitored daily. An electronic time controlled lighting system was used to provide a 12 h light/12 h dark cycle. 3 mice for each indicated time point were administered 10 mg/Kg BTSA1 in 1% DMSO, 30% PEG-400, 65% D5W (5% dextrose in water), 4% Tween-80 either by an oral gavage or intravenous injection. Mice were sacrificed, and plasma samples were harvested at 0 h, 0.25 h, 0.5 h, 1 h, 2 h, 4 h, 8, 24 h, 48 h and analyzed for BTSA1 levels using LC-MS/MS. Pharmacokinetics parameters were calculated using Phoenix WinNonlin 6.3. All animal experiments were approved by and performed within the guidelines and regulations approved by the Institutional Animal Care and Use Committee of the Albert Einstein College of Medicine. Experiments performed at SIMM-SERVIER joint Biopharmacy Laboratory.

Human Leukemia Xenografts and In Vivo Efficacy Study.

All animal experiments were approved by and performed in compliance with the guidelines and regulations approved by the Institutional Animal Care and Use Committee of the Albert Einstein College of Medicine. For survival experiments, 6-8 week old NOD-SCID IL2Rγ null (NSG) mice (Jackson Laboratory) were subjected to sublethal (200 rad) total body irradiation and 3 hours later injected with $5 \times 10^5$ THP-1 cells by tail vein. Ten days after inoculation, mice with AML disease, were divided into two groups (n=7 per arm), and treated with vehicle and 10 mg/kg BTSA1 by IP route every two days. The vehicle for BTSA1 was 1% DMSO, 30% PEG-400, 65% D5W, 4% Tween-80. The survival distributions of BTSA1- and vehicle-treated mice were determined using the Kaplan-Meier method and compared using the log-rank test. Body weight and blood counts of animals were monitored during disease progression and treatment. For measurement of THP-1 infiltration, 6-8 week old NOD-SCID IL2Rγ null (NSG) mice were subjected to sublethal (200 rad) total body irradiation and 3 hours later injected with $3 \times 10^5$ THP-1 cells by tail vein. Experiments were repeated as above with two groups (n=4 per arm) and mice sacrificed after 30 days and tissues collected for FACS analysis. Peripheral blood from NOD-SCID IL2Rγ null (NSG) mice was obtained by facial vein puncture and collected in EDTA-coated tubes (BD cat. 365973). Blood counts were determined on a Forcyte Veterinary Hematology Analyzer (Oxford Science Inc.)

Flow Cytometric Determination of Engraftment and Tumor Burden.

To determine human cells in THP-1-transplanted NOD-SCID IL2Rγ null (NSG) mice, cells from blood, bone marrow, liver and spleen were isolated. Briefly, mononuclear cells were purified by lysis of erythrocytes. To distinguish donor from host cells in transplanted mice, cells were stained with murine CD45 Ly-5 30-F11 (eBioscience cat. 12-0451-83) human CD45 2D1 (eBioscience cat. 17-9459-42) and human CD15 HI98 (eBioscience cat. 11-0159-42). Analysis and sorting were performed using a FACSAria II Special Order System (BD Biosciences, San Jose, Calif.).

Toxicity Studies In Vivo.

6-8 week old NOD-SCID IL2Rγ null (NSG) mice (Jackson Laboratory) were divided into three groups (n=3 per arm), and treated with vehicle and 15 mg/Kg BTSA1 by IP route every other day. Mice were monitored daily and body weight was monitored every two days. After 30 days of vehicle and drug treatments mice were subjected to euthanasia and necropsy (Animal Pathology Core, Albert Einstein College of Medicine) and tissues (e.g. bone marrow, spleen, liver, kidney, lung heart, brain) were harvested for fixation in 10% buffered formalin (Fisher Scientific). Paraffin-embedded sections (5 m) were stained with H&E. Peripheral blood from NOD-SCID IL2Rγ null (NSG) mice was obtained by facial vein puncture and collected in EDTA-coated tubes (BD cat. 365973). Blood counts were determined on a Forcyte Veterinary Hematology Analyzer (Oxford Science Inc.).

Evaluation of Apoptosis in Primary AML Leukemia and Healthy Cells.

Primary human AML and healthy control samples were incubated with 5 and 10 μM of BTSA1 in Iscove's modified Dulbecco's medium with 10% fetal bovine serum at 37° C. After 48 hours, cells were rinsed with PBS and stained with antibodies against CD34 (8G12) and CD38 (HIT2). After washing with PBS, cells were mixed with prediluted fluorescein isothiocyanate-conjugated annexin V (Invitrogen), incubated at room temperature for 15 minutes, and resuspended in 0.5 mL of annexin binding buffer (Invitrogen). Just before flow cytometric analysis, DAPI (Acros Organics) was added to the cells at a final concentration of 1 μg/mL. Viability, apoptosis, and necrosis of CD34+/CD38− stem cells were analyzed by flow cytometry using a FACSAria II Special Order System (BD Biosciences) as performed previously (Schinke et al., 2015).

Multiplexed Cytotoxicity Assay.

Cells were grown in RPMI 1640, 1% FBS, 2 mM L-alanyl-L-glutamine, 1 mM Na pyruvate, or a special medium. Cells were seeded into 384-well plates and incubated in a humidified atmosphere of 5% $CO_2$ at 37° C. Compounds were added the day following cell seeding. At the same time, a time zero untreated cell plate was generated. After a 3-day incubation period, cells were fixed and stained with fluorescently labeled antibodies and nuclear dye to allow imaging of nuclei, apoptotic cells and mitotic cells.

Compounds were serially diluted in half-log steps from the highest test concentration, and assayed over 10 concentrations with a maximum assay concentration of 0.1% DMSO. Automated fluorescence microscopy was carried out using a Molecular Devices ImageXpress Micro XL high-content imager, and images were collected with a 4× objective. 16-bit TIFF images were acquired and analyzed with MetaXpress 5.1.0.41 software.

Data Analysis.

Cell proliferation was measured by the fluorescence intensity of an incorporated nuclear dye. The output is referred to as the relative cell count, where the measured nuclear intensity is transformed to percent of control (POC) using the following formula:

$$POC = \frac{I_x}{I_0} \times 100$$

where $I_x$ is the nuclear intensity at concentration x, and $I_0$ is the average nuclear intensity of the untreated vehicle wells.

Cellular response parameters were calculated using non-linear regression to a sigmoidal single-site dose response model:

$$y = A + \frac{B - A}{1 + (C/x)^D}$$

where y is a response measured at concentration x, A and B are the lower and upper limits of the response, C is the concentration at the response midpoint ($EC_{50}$), and D is the Hill Slope (Fallahi-Sichani et al. 2013).

Time zero non-treated plates were used to determine the number of doublings during the assay period, using the formula:

$$\text{Doublings} = \log_2\left(\frac{N}{N_{T0}}\right)$$

where N is the cell number in untreated wells at the assay end point and $N_{T0}$ is the cell number at the time of compound addition.

Cell count $IC_{50}$ is the test compound concentration at 50% of maximal possible response. $EC_{50}$ is the test compound concentration at the curve inflection point or half the effective response (parameter C of the fitted curve solution). $GI_{50}$ is the concentration needed to reduce the observed growth by half (midway between the curve maximum and the time zero value). Activity area is an estimate of the integrated area above the curve (Barretina et al. 2012). Activity area values range from 0-10, where a value of zero indicates no inhibition of proliferation at all concentrations, and a value of 10 indicates complete inhibition of proliferation at all concentrations. In rare instances, values <0 or >10 may be observed. In these instances, values <0 should be considered as equivalent to 0, whereas values >10 should be considered equivalent to 10.

An antibody to activated caspase-3 was used to label cells from early to late stage apoptosis (Thornberry et al. 1998). The output is shown as a fold increase of apoptotic signal over vehicle background normalized to the relative cell count in each well. The concentration of test compound that caused a 5-fold induction in the caspase-3 signal is reported, indicating a significant apoptosis induction.

An antibody to phosphorylated histone H3 was used to label mitotic cells (Gasparri et al. 2006). The output is shown as a fold induction of mitotic signal over vehicle background normalized to the relative cell count in each well. The concentration of test compound that caused a 2-fold increase or decrease in the phospho-histone H3 signal is reported. A >2-fold increase indicates the test agent induced an accumulation of cells in the G2/M phase of the cell cycle. A >2-fold decrease indicates G1/S block, but only when cytotoxicity levels are below the measured cell count $IC_{95}$. When this decrease is observed at concentrations higher than the cell count $IC_{95}$, the loss in mitotic cells is most likely due to a more general cytotoxicity effect rather than a true G1/S phase block.

The concentration of compound that achieved 6 standard deviations above the mean of vehicle background in either caspase-3 or phospho-histone H3 is also reported. Wells with cell count POC values <5% were eliminated from caspase-3 or phospho-histone H3 induction analysis.

Curve-fitting, calculations, and report generation was performed using a custom data reduction engine and MathIQ based software (AIM).

Human Leukemia Xenografts and In Vivo Efficacy Study.

For measurement of MOLM-13 infiltration, 6-8 week old NOD-SCID IL2Rγ null (NSG) mice (Jackson Laboratory) were subjected to sublethal (200 rad) total body irradiation and 3 hours later injected with $5 \times 10^5$ MOLM-13 cells by tail vein. Three days after inoculation, mice with AML disease, were divided into two groups (n=5 per arm), and treated with vehicle, 10 mg/kg BTSA1 by IP every two days. For MOLM-13 transplanted NOD-SCID IL2Rγ null (NSG) mice, infiltration was assayed two weeks after inoculation by bone marrow aspirate extraction of blood samples followed by FACS analysis. Additionally, infiltration was also quantified from sacrificed animals three weeks after inoculation by FACS analysis from spleen, bone marrow, peripheral blood and liver samples.

Flow Cytometric Determination of Engraftment and Tumor Burden.

To determine human cells in THP-1-transplanted NOD-SCID IL2Rγ null (NSG) mice, cells from blood, bone marrow, liver and spleen were isolated. Briefly, mononuclear cells were purified by lysis of erythrocytes. To distinguish donor from host cells in transplanted mice, cells were stained with murine CD45 Ly-5 30-F11 PE (eBioscience Cat. 12-0451-83) human CD45 2D1 APC (eBioscience Cat. 17-9459-42) and human CD15 HI98 FITC (eBioscience Cat. 11-0159-42) conjugated antibodies. To distinguish donor from MOLM-13 cells in transplanted mice, cells were stained with murine CD45.1 FITC Monoclonal Antibody (A20) (Affymetrix Cat. 11045382), human CD45 PE (BD Cat. 560975) and human CD15 PB (Thermo Fisher Cat. MHCD1528) conjugated antibodies. Analysis and sorting were performed using a FACSAria II Special Order System (BD Biosciences, San Jose, Calif.).

Mitochondrial Depolarization Assay (mΔΨ) from Bone Marrow Samples from MOLM-13 Xenografts.

NOD-SCID IL2Rγ null (NSG) mice (Jackson Laboratory) were subjected to sublethal (200 rad) total body irradiation and 3 hours later injected with $5 \times 10^5$ MOLM-13 cells by tail vein. 15 days after transplantation, mice were treated with 10 mg/kg BTSA1 or vehicle via IP for two consecutive days. Following treatment, mice were sacrificed and peripheral blood and bone marrow samples harvested. Briefly, erythrocytes from bone marrow samples were lysed using an ACK buffer. Immediately, samples were resuspended in RPMI 1640 media (Invitrogen) supplemented with 10% FBS, 100 U ml-1 penicillin/streptomycin, and 2 mM l-glutamine. Samples were then stained with 100 nM TMRE (Sigma Cat. 87917) for 30 minutes at 37° C. Subsequently, cells were pelleted by centrifugation and washed two times in 1×PBS/0.5% BSA. Cells were then stained with murine CD45.1 FITC Monoclonal Antibody (A20) (Affymetrix Cat. 11045382), human CD45 PE (BD Cat. 560975) and human CD15 PB (Thermo Fisher Cat. MHCD1528) for 30 minutes on ice. After incubation, cells were pelleted by centrifugation followed by two washes with 1×PBS/0.5% BSA. Cells where then resuspended in 300 μL of 1×PBS/0.5% BSA and analyzed by FACS. Analysis and sorting were performed using a FACSAria II Special Order System (BD Biosciences, San Jose, Calif.).

Immunohistochemistry (IHC) Analysis of Bone Marrow Samples.

Femur from MOLM-13 xenografts of mice treated with 10 mg/kg BTSA1 or vehicle for 3 weeks were dissected and fixed in 10% buffered formalin (Fisher Scientific) for 24 hours followed by decalcification of bone. Paraffin-embedded sections were then stained with cleaved caspase-3 antibody (Cell Signaling Cat. 9661) or with the ApopTag Peroxidase in situ Apoptosis Detection Kit (Millipore Cat. S7100), which detects apoptotic cells in situ by labeling and detecting DNA strand breaks by the TUNEL method. Stained slides were imaged using the PerkinElmer P250 High Capacity Slide Scanner under brightfield using a 20× objective. Quantification and analysis of densitometry of IHC was performed using Panoramic Viewer. Using Panoramic Viewer, bone marrow sections from slides were selected followed by analysis using the "Densito Quant Module" This module measures the density of immunostain on the digital slides by distributing pixels to negative and 3 grades of positive classes by their RGB values. For caspase cleavage stain, the percentage of total positive signals of BTSA1 or vehicle treated samples was obtained using the Densito Quant Module and plotted as bar-graphs. For TUNEL stain, the percentage of the total medium and strong positive signals of BTSA1 or Vehicle treated samples was obtained using the Densito Quant Module and plotted as bar-graphs.

Statistics.

Statistical significance for pair-wise comparison of groups was determined by 2-tailed Student's t test and by one-way ANOVA using GraphPad PRISM software (Graph Pad Inc., CA). P values of less than 0.05 were considered significant.

Materials and Methods for the Chemical Syntheses.

All chemical reagents and solvents were obtained from commercial sources (Aldrich, Acros, Fisher) and used without further purification unless otherwise noted. Anhydrous solvents (tetrahydrofurane, toluene, dichloromethane, diethyl ether) were obtained using a Pure Solv™ AL-258 solvent purification system. Ethanol was dried over activated 4 Å molecular sieves. Microwave reactions were performed on an Anton Paar Monowave 300. Chromatography was performed on a Teledyne ISCO CombiFlash $R_f$ 200i using disposable silica cartridges (4, 12, and 24 g). Analytical thin layer chromatography (TLC) was performed on aluminum-backed Silicycle silica gel plates (250 μm film thickness, indicator F254). Compounds were visualized using a dual wavelength (254 and 365 nm) UV lamp and/or staining with CAM (cerium ammonium molybdate) or KMnO$_4$ stains. NMR spectra were recorded on Bruker DRX300 and DRX 600 spectrometers. $^1$H and $^{13}$C chemical shifts (δ) are reported relative to tetramethyl silane (TMS, 0.00/0.00 ppm) as internal standard or to residual solvent (CD$_3$OD: 3.31/49.00 ppm; CDCl$_3$: 7.26/77.16 ppm; dmso-d$_6$: 2.50/39.52 ppm). Mass spectra were recorded on a Shimadzu LCMS2010EV (direct injection unless otherwise noted). High-resolution electrospray ionization mass spectra (ESI-MS) were obtained at the Albert Einstein College of Medicine's Laboratory for Macromolecular Analysis and Proteomics. Elemental analyses were obtained from Intertek USA, Inc. (Whitehouse, N.J.; worldwideweb.intertek.com/pharmaceutical/analysis/whitehouse-nj).

N-(3-(2-(2-(3-aminopropoxy)ethoxy)ethoxy)propyl)-5-((3aS,4S,6aR)-2-oxohexahydro-1H-thieno[3,4-d]imidazol-4-yl)pentanamide (Hang et al. 2004) was synthesized according to a literature procedure.

Synthesis of Compounds 1 and 2.

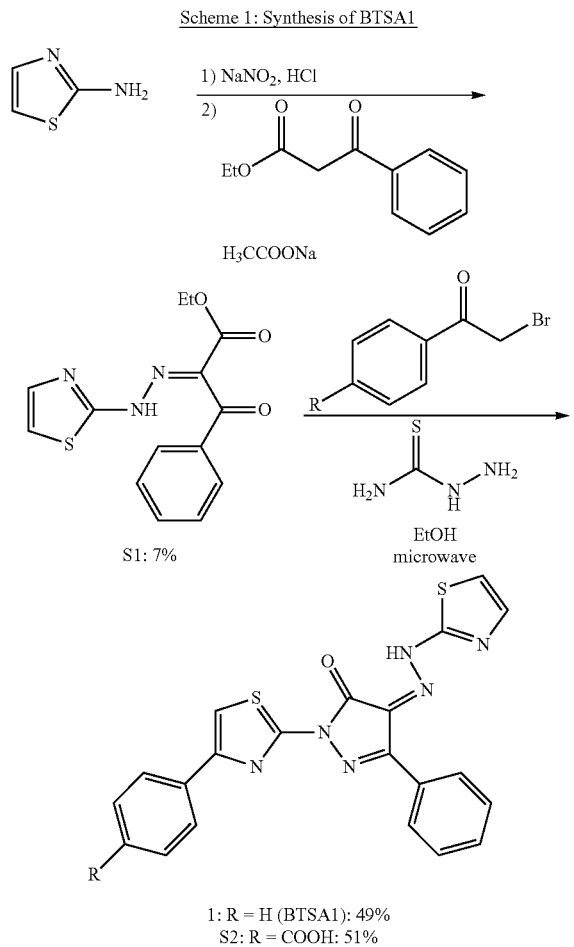

(1) and the carboxylate-decorated analog S2. 2-Aminothiazole was diazotized and reacted in situ with ethyl 3-oxo-3-phenylpropanoate to give intermediate S1. S1 was reacted with the respective 2-bromoacetophenone and hydrazinecarbothioamide under microwave conditions to give BTSA1 (1) or S2, respectively.

Synthesis of ethyl-3-oxo-3-phenyl-2-(2-(thiazol-2-yl)hydrazono)propanoate (S1): To a solution of thiazol-2-amine (1.00 g, 9.99 mmol) in hydrochloric acid (3.94 mL, 130 mmol) and water (3.94 mL) at T<−5° C. [Note: internal thermometer, ice/NaCl cooling bath; additional cooling with N$_2$(l) droplets in the reaction vessel] was added drop-wise a solution of sodium nitrite (689 mg, 9.99 mmol) in water (4.0 mL). The temperature was kept between −5 and 0° C. The diazonium salt was formed as a clear, red-orange solution. After stirring this solution at the given temperature for another 10 min, it was added in small portions, down the thermometer, to a pre-cooled (0° C.) slurry of ethyl 3-oxo-3-phenylpropanoate (0.384 g, 1.997 mmol) and sodium acetate (12.29 g, 150 mmol) in ethanol (20.0 mL). The first drops caused a color change to dark green. After complete addition, the now dark brown slurry was stirred over night at RT. Water (ca 300 mL) was added, the resulting mixture extracted with EtOAc (first 600 mL, then 2×150 mL). The combined organic layers were dried (MgSO$_4$), filtered and evaporated in vacuo to yield the crude product as dark purple resin.

After purification on the Isco CombiFlash (absorbed on ca 15 g silica for loading; 80 g column; gradient 10→30% EtOAc in hexanes), ethyl-3-oxo-3-phenyl-2-(2-(thiazol-2-yl)hydrazono)propanoate (S1; 1.06 g, 3.50 mmol, 7%) was obtained as viscous red-orange oil (mixture of E/Z isomers). TLC: R$_f$ 0.24 (4:1, hex:EtOAc). $^1$H-NMR (600 MHz, CDCl$_3$): (Signals of major isomer given) δ 7.96 (dd, J=8.2, 1.2 Hz, 2H), 7.61-7.58 (m, 1H), 7.48 (dd, J=8.2, 7.6 Hz, 2H), 7.38 (d, J=3.5 Hz, 1H), 6.83 (d, J=3.5 Hz, 1H), 4.37 (q, J=7.1 Hz, 2H), 1.32 (t, J=7.1 Hz, 3H). $^{13}$C-NMR (151 MHz, CDCl$_3$): δ 188.4, 167.0, 162.6, 140.0, 136.3, 133.3, 130.0, 128.3, 113.2, 62.2, 14.0. ESI-MS m/z (rel int): (pos) 325.9 ([M+Na]$^+$, 65), 303.9 ([M+H]$^+$, 100); (neg) 301.9 ([M−H]$^−$, 10).

Synthesis of 5-phenyl-2-(4-phenylthiazol-2-yl)-4-(2-(thiazol-2-yl)hydrazono)-2,4-dihydro-3H-pyrazol-3-one (1): 2-Bromo-1-phenylethan-1-one (33.0 mg, 0.166 mmol) was weighed into a dry 10 mL microwave vessel, equipped with a rubber septum and stir bar, under an argon atmosphere. Dry ethanol (0.40 mL) was added at room temperature, upon which most of the starting material dissolved. To this mixture was added hydrazinecarbothioamide (15.1 mg, 0.166 mmol) neat, in one portion. The reaction mixture was stirred at room temperature for a 60 min. To the solution obtained from the first step, a solution of ethyl (Z)-3-oxo-3-phenyl-2-(2-(thiazol-2-yl)hydrazono)propanoate (S1; 50.0 mg, 0.165 mmol) in ethanol (1.10 mL) was added. The mixture was heated in the microwave (130° C., 30 min) (conventional heating can also be used). At the end of the reaction, a dark red-purple precipitate was submerged in a dark red solution. TLC analysis indicated full conversion of the starting material, MS analysis confirmed product mass. The precipitate was filtered in a buchner filter, washed first with little cold EtOH (ca 1 mL), then with diethyl ether b(ca 1 mL). The product was dried in high vacuum. (Z)-5-phenyl-2-(4-phenylthiazol-2-yl)-4-(2-(thiazol-2-yl)hydrazono)-2,4-dihydro-3H-pyrazol-3-one (1; 35 mg, 0.081 mmol, 49.3% yield) was obtained as dark ruby-red solid. As an alternative to the microwave heating, conventional heating in an oil bath (80° C., 4 h), afforded comparable results. The crude products after filtration are pure as judged by their $^1$H and $^{13}$C NMR spectra. However, elemental analyses of crude samples as well as samples from commercial sources revealed remaining impurities (that cannot be explained by trace solvent remainders). The crude product can be additionally purified by column chromatography (silica gel, gradient of MeOH in CH$_2$Cl$_2$) or crystallization from 1,4-dioxane. Only the latter afforded material that gives satisfactory data in the elemental analysis (calculated: C: 58.59; H: 3.28; N: 19.52; S: 14.89; found: C: 58.52; H: 3.18; N:

19.17; S: 14.63). However, all samples showed very similar activities well within the error margins. TLC: R$_f$ 0.75 (19:1, CH$_2$Cl$_2$/MeOH); 0.11 (1:1, hex:EtOAc). $^1$H-NMR (600 MHz, dmso-d$_6$): δ 8.16 (d, J=7.0 Hz, 2H), 7.99 (dd, J=8.2, 1.1 Hz, 2H), 7.83 (s, 1H), 7.71 (d, J=4.0 Hz, 1H), 7.57-7.51 (m, 3H), 7.46 (t, J=7.7 Hz, 2H), 7.37-7.34 (m, 2H). $^{13}$C-NMR (151 MHz, dmso-d$_6$): δ 179.0, 154.7, 152.9, 149.9, 149.0, 134.1, 131.9, 130.5, 129.9(6), 129.9(2), 128.7, 128.5, 127.9(7), 127.9(6), 125.9, 114.0, 109.0. ESI-MS m/z (rel int): (pos) 883.2 ([2M+Na]$^+$, 35), 452.9 ([M+Na]$^+$,20), 430.9 ([M+H]$^+$, 60), 168.8 (100) (neg) 429.0 ([M−H]$^−$, 100). HRMS calculated for C$_{21}$H$_{15}$N$_6$OS$_2$ (M+H): 431.0749. found: 431.0767.

Synthesis of 4-(2-(5-oxo-3-phenyl-4-(2-(thiazol-2-yl)hydrazono)-4,5-dihydro-1H-pyrazol-1-yl)thiazol-4-yl)benzoic acid (S2): Synthesized as described for 1 using 4-(2-bromoacetyl)benzoic acid (40.0 mg, 0.165 mmol) instead of 2-bromo-1-phenylethan-1-one. S2 was obtained as red solid (40.0 mg, 0.084 mmol, 51%). The product contained about 6% of the corresponding ethyl ester as an impurity, and was used in the next step without further purification. Note: microwave conditions are required for this substrate, as no complete conversion was obtained using conventional heating. TLC: R$_f$ 0.30 (19:1, CH$_2$Cl$_2$/MeOH). $^1$H-NMR (600 MHz, dmso-d$_6$): δ 8.15 (s, 2H), 8.11 (d, J=8.5 Hz, 2H), 8.03 (m, 3H), 7.72 (d, J=4.0 Hz, 1H), 7.58-7.52 (m, 3H), 7.36 (d, J=4.0 Hz, 1H). $^{13}$C-NMR (151 MHz, dmso-d$_6$): δ 179.8, 167.5, 155.3, 153.4, 149.7, 149.3, 138.4, 132.3, 131.0, 130.4(1), 130.4(0), 130.3, 130.2, 129.0, 128.5, 126.4, 114.5, 111.8. ESI-MS m/z (rel int): (473.0 ([M−H]$^−$, 100). HRMS calculated for C$_{22}$H$_{13}$N$_6$O$_3$S$_2$(M−H) 473.0491. found: 473.0512.

Scheme 2: Synthesis of the Biotin-tagged BTSA1-analog 2.

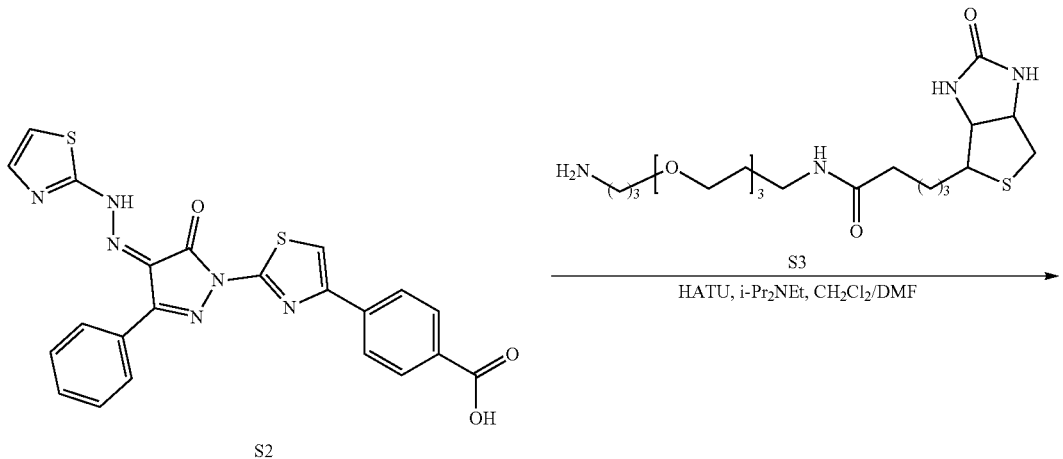

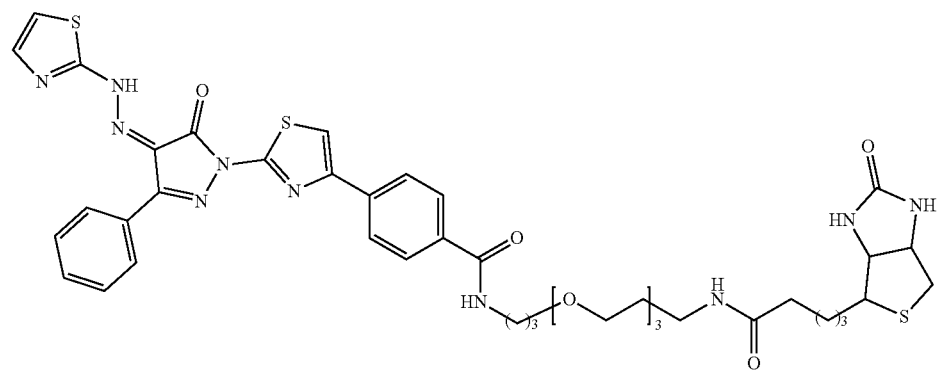

The carboxylic acid S2 was coupled with the known Biotin tag, N-(3-(2-(2-(3-aminopropoxy)ethoxy)ethoxy)propyl)5-((4S)-2-oxohexahydro-1H-thieno[3,4-d]imidazol-4-yl)pentanamide (S3) using a standard HATU protocol.

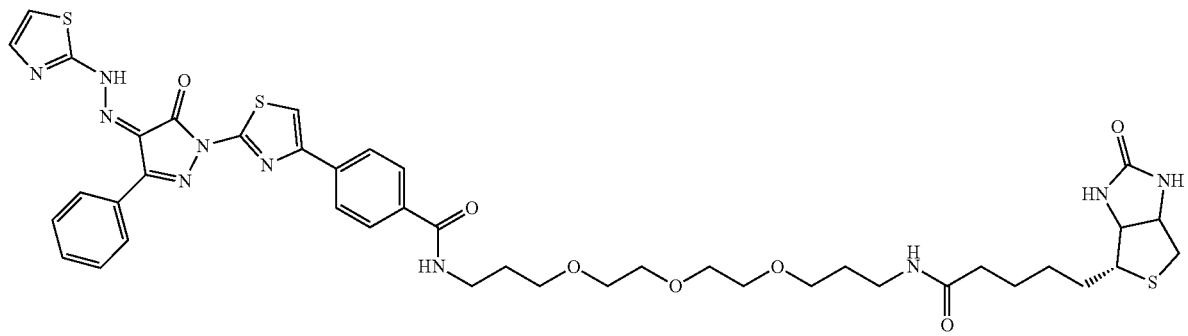 [SMILES: O=C(CCCC[C@H]1SCC2NC(=O)NC21)NCCCOCCOCCOCCCNC(=O)c1ccc(-c2csc(N3N=C(c4ccccc4)/C(=N/Nc4nccs4)C3=O)n2)cc1]

Synthesis of N-(15-oxo-19-((4R)-2-oxohexahydro-1H-thieno[3,4-d]imidazol-4-yl)-4,7,10-trioxa-14-azanonadecyl)-4-(2-(5-oxo-3-phenyl-4-(2-(thiazol-2-yl)hydrazono)-4,5-dihydro-1Hpyrazol-1-yl)thiazol-4-yl)benzamide (2): 4-(2-(5-Oxo-3-phenyl-4-(2-(thiazol-2-yl)hydrazono)-4,5-dihydro-1H-pyrazol-1-yl)thiazol-4-yl)benzoic acid (S2; 15.0 mg, 0.032 mmol) was dissolved in dry dichloromethane (500 µL). N-ethyl-N-isopropylpropan-2-amine (27 µL, 0.16 mmol) was added. followed by HATU (13.2 mg, 0.035 mmol). Dry dimethylformamide (200 µL) was added to improve solubility. After 25 min, N-(3-(2-(2-(3-aminopropoxy)ethoxy)ethoxy)propyl)-5-((4S)-2-oxohexahydro-1H-thieno[3,4-d]imidazol-4-yl)pentanamide (15.5 mg, 0.035 mmol) in dimethylformamide (500 µL) was added at room temperature. LC-MS and TLC analysis of a reaction aliquot (micro-workup: satd. aq. NaHCO$_3$/EtOAc) after 2 h indicated full conversion. The solvent was evaporated on the rotary evaporator, then by vacuum destillation. The residue was dissolved in dichloromethane/MeOH, absorbed on silica gel and subjected to column chromatography (silica; 17:3:1, EtOAc:MeOH:NH$_4$OH). N-(15-oxo-19-((4S)-2-oxohexahydro-1H-thieno[3,4-d]imidazol-4-yl)-4,7,10-trioxa-14-azanonadecyl)-4-(2-(5-oxo-3-phenyl-4-(2-(thiazol-2-yl)hydrazono)-4,5-dihydro-1H-pyrazol-1-yl)thiazol-4-yl)benzamide (2; 12.9 mg, 0.014 mmol, 45%) was obtained as bright orange-red solid in form of an ammonium salt (as identified by $^1$H-NMR). TLC: R$_f$0.47 (17:3:1, EtOAc/MeOH/NH$_4$OH). $^1$H-NMR (600 MHz, dmso-d$_6$): δ 8.49 (t, J=5.5 Hz, 1H), 8.21 (dd, J=6.1, 0.6 Hz, 2H), 8.07 (d, J=8.4 Hz, 2H), 7.92 (d, J=8.4 Hz, 2H), 7.84 (s, 1H), 7.73 (dd, J=7.3, 3.8 Hz, 1H), 7.65 (d, J=3.2 Hz, 1H), 7.51-7.49 (m, 2H), 7.44 (t, J=7.3 Hz, 1H), 7.25 (d, J=3.2 Hz, 1H), 6.41 (s, 1H), 6.34 (s, 1H), 4.28 (dd, J=7.4, 5.2 Hz, 1H), 4.11 (ddd, J=7.4, 4.8, 2.1 Hz, 1H), 3.55-3.50 (m, 6H), 3.49-3.46 (m, 4H), 3.38 (t, J=6.7 Hz, 2H), 3.34 (t, J=6.7 Hz, 2H), 3.09-3.05 (m, 3H), 2.80 (dd, J=12.4, 5.2 Hz, 1H), 2.56 (d, J=12.4 Hz, 1H), 2.04 (dd, J=9.7, 5.2 Hz, 2H), 1.78 (quintet, J=6.6 Hz, 2H), 1.60 (dd, J=8.6, 4.9 Hz, 3H), 1.48 (t, J=7.3 Hz, 3H), 1.23 (s, 2H). $^{13}$C-NMR (151 MHz, dmso-d$_6$): δ 182.7, 171.9, 165.8, 162.7, 155.4, 152.9, 149.8, 148.4, 141.2, 136.9, 133.4, 132.8, 128.6, 128.1(2), 128.0(5), 127.6, 125.5, 121.9, 115.4, 109.6, 69.8(0), 69.7(7), 69.6, 69.5, 68.3, 68.1, 61.0, 59.2, 55.4, 39.8 (concealed by the solvent signal, identified by HSQC experiment), 36.7, 35.7, 35.2, 29.4 (2 carbons, as confirmed by HSQC experiment), 28.2, 28.0, 25.3. ESI-MS m/z (rel int): (pos) 903.4 ([M+H]$^+$, 15), 545.3 (85), 405.1 (100), 295.2 (50); (neg) 901.5 ([M−H]$^−$, 15), (312.8, 30). HRMS calculated for C$_{42}$H$_{49}$N$_{10}$O$_7$S$_3$ (M−H): 901.2948. found: 901.3000.

An additional synthetic route, using BTSA1 as an example, is shown below.

Scheme 3: Synthesis of fluorescein-labeled BTSA1 3.

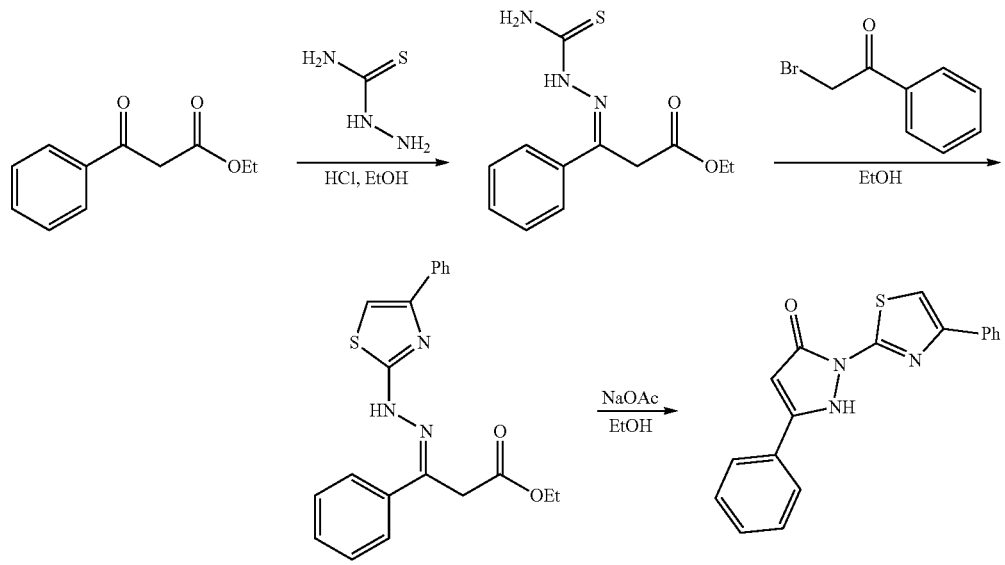

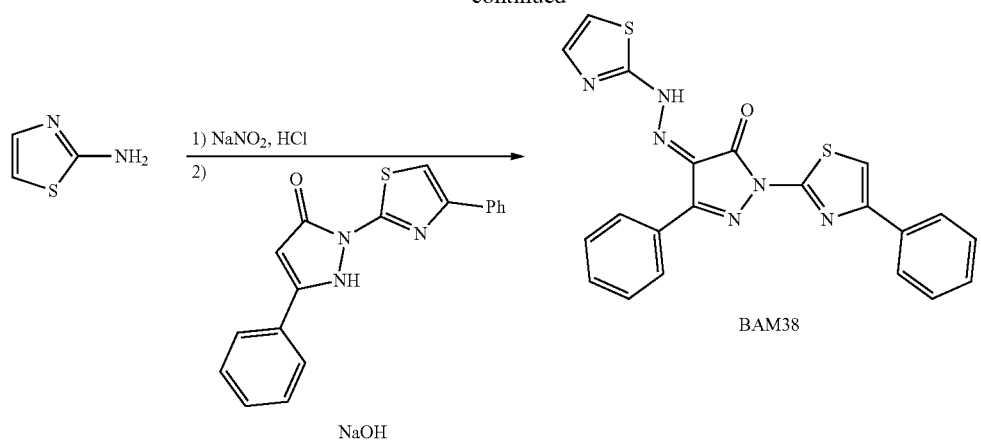
BAM38
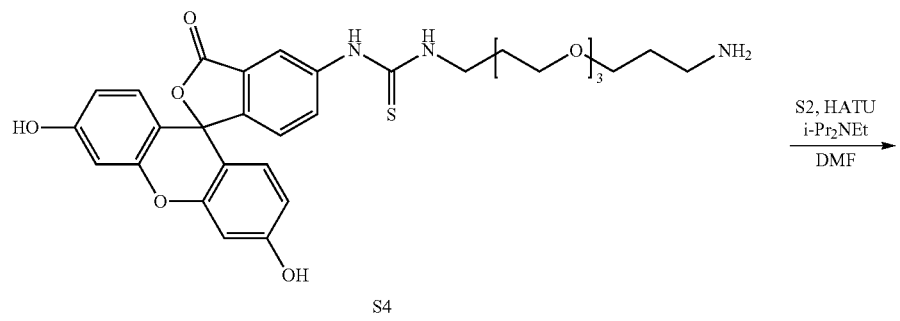
S4
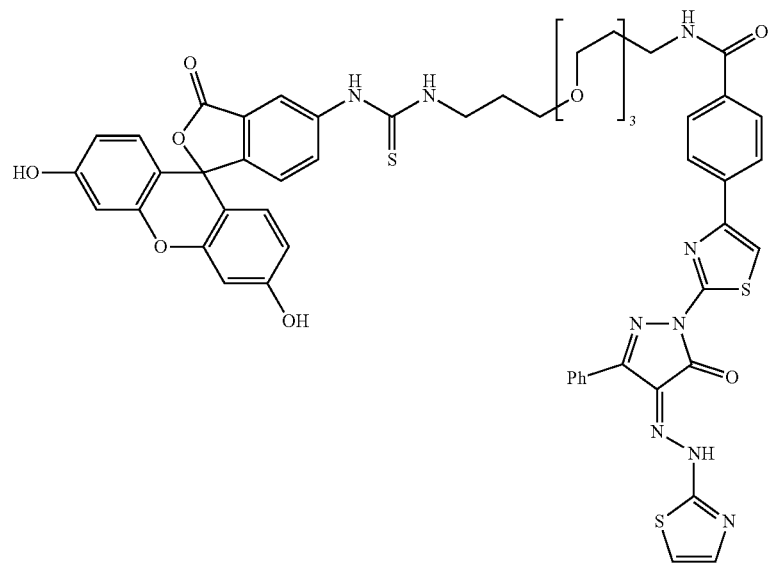
3
The PEG linker-eqipped FitC derivative S4 (synthesized according to literature) was attached to the carboxylic acid of BTSA1-analog S2 utilizing standard HATU coupling chemistry. HATU = 1-[Bis˜(di˜methylamino)methylene]-1H-1,2,3-triazolo[4,5-b]pyridinium hexafluoro˜phos˜phate; DMF = N,N-dimethylformamide.

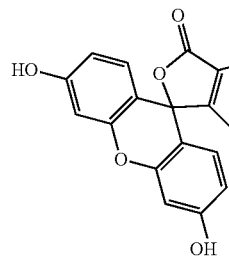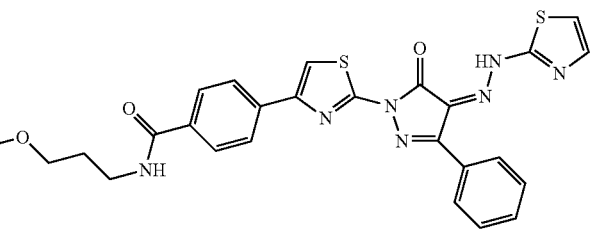

Synthesis of N-(1-((3',6'-dihydroxy-3-oxo-3H-spiro [isobenzofuran-1,9'-xanthen]-5-yl) amino)-1-thioxo-6,9,12-trioxa-2-azapentadecan-15-yl)-4-(2-(5-oxo-3-phenyl-4-(2-(thi-α-zol-2-yl)hydrazineylidene)-4,5-dihydro-1H-pyrazol-1-yl)thiazol-4-yl)benzamide (3): In a dry conical tube with stir bar and septum, S2 (22.0 mg, 46.0 µmol) and HATU (19.4 mg, 50.0 µmol, 1.10 equiv) were dissolved in dry N,N-dimethylformamide (DMF; 1.00 mL). Hunig's Base (40.5 µL, 0.232 mmol, 5.00 equiv) was added at RT and the mixture was stirred for 30 min. 1-(3-(2-(2-(3-aminopropoxy)ethoxy)ethoxy)pro-pyl)-3-(3',6'-di-hydroxy-3-oxo-3H-spiro[isobenzofuran-1,9'-xanthen]-5-yl)thiourea (S4; 28.3 mg, 46.0 µmol, 1.00 equiv) in dry DMF (4.00 mL) was added at RT, and the resulting mixture was stirred at RT in the dark. After 18 h, MS analysis of a reaction aliquot indicated product formation (TLC analysis was nconclusive). The solvent was evaporated in vacuo. Purification on the Isco CombiFlash (silica gel, 1731-mix (17:3:1 EtOAc: MeOH:H$_2$O) in EtOAc, 40%→85%) afforded N-(1-((3',6'-dihydroxy-3-oxo-3H-spiro[isobenzofuran-1,9'-xanthen]-5-yl)amino)-1-thioxo-6,9,12-trioxa-2-azapentadecan-15-yl)-4-(2-(5-oxo-3-phenyl-4-(2-(thiazol-2-yl)hydrazineylidene)-4,5-dihydro-1H-pyrazol-1-yl)thiazol-4-yl)-benzamide (3; 13.2 mg, 12 µmol, 27%, >90% purity as estimated based on the 1H-NMR trace) as light red solid. TLC: R$_f$=0.28 (1:1, EtOAc:1731-mix). $^1$H-NMR (600 MHz, dmso-d$_6$): δ 10.13 (s, 2H), 9.97 (s, 1H), 8.50 (t, J=5.6 Hz, 1H), 8.25-8.18 (m, 3H), 8.13 (s, 1H), 8.07 (d, J=8.4 Hz, 2H), 7.92 (d, J=8.4 Hz, 2H), 7.82 (s, 1H), 7.73 (d, J=6.7 Hz, 1H), 7.64 (d, J=3.1 Hz, 1H), 7.49 (t, J=7.5 Hz, 2H), 7.42 (t, J=7.3 Hz, 1H), 7.24 (d, J=3.5 Hz, 1H), 7.17 (d, J=8.3 Hz, 1H), 6.66 (s, 2H), 6.60 (d, J=8.7 Hz, 2H), 6.56 (dd, J=8.7, 2.0 Hz, 2H), 3.55-3.47 (m, 16H), 1.84-1.76 (m, 4H). $^{13}$C-NMR (151 MHz, dmso-d$_6$): δ 182.8, 180.4, 168.6, 165.9, 159.5, 155.4, 153.0, 151.9, 149.9, 148.4, 141.5, 141.3, 136.9, 133.4, 132.9, 129.4, 129.1, 128.5, 128.1, 128.1, 127.6, 125.6, 124.1, 121.7, 116.5, 115.5, 112.7, 109.8, 109.6, 102.2, 69.8(2), 69.7(6), 69.6 (2 carbons, based on signal shape and HSQC correlation[1]), 68.4, 68.2, 41.5, 36.7, 29.4, 28.6. HRMS (for C$_{53}$H$_{48}$N$_9$O$_{10}$S3): calculated: 1066.2681; found: 1066.2719.
[1]Based on the HSQC data, an unambiguous assignment was not possible, due to the overlap of the corresponding signals in the proton spectrum. However, the group of 3 signals at around 69 ppm, based on the signals seen in the proton spectrum can be identified as the four ethylene glycol methylene groups from the PEG linker. The signal at 69.6 ppm appears to have a much broader base and higher amplitude than the neighboring signals at 69.82 and 69.76 ppm, respectively, suggesting that it is actually two overlapping methylene signals.

Derivatives of these compounds can be synthesized by standard techniques in the art, for example, see Modern Organic Synthesis in the Laboratory, Oxford University Press, USA (Sep. 10, 2007), and Advanced Organic Chemistry: Reactions, Mechanisms and Structure, Jerry March, John Wiley & Sons, New York (1992), which are hereby incorporated by reference.

Results

BTSA1 is a Potent and Selective BAX Trigger Site Activator

A pharmacophore model was generated based on the structural information of previously reported models of BIM BH3 helix and BAM7 compound bound to the N-terminal activation site (trigger site) of BAX. Synthesized compounds and chemical libraries were evaluated to fit the pharmacophore model and have an increased affinity for the BAX trigger site. A competitive fluorescence polarization assay that evaluates the capacity of compounds to compete a fluorescein-labeled stapled peptide of the BIM BH3 helix, FITC-BIM SAHBA2, from the BAX trigger site, was used to determine the binding potency (Gavathiotis et al., 2008; Gavathiotis et al., 2012). Compound, BTSA1 (FIG. 1A), competed FITC-BIM SAHB$_{A2}$ with IC$_{50}$ of 250 nM, and compared to the binding of BIM SAHB$_{A2}$ helix (IC$_{50}$=280 nM) and BAM7 (IC$_{50}$=3.2 µM) (FIG. 1B) demonstrated the most potent small-molecule binding for the BAX trigger site. Moreover, direct binding of fluorescein-labeled BTSA1 to BAX showed higher nanomolar affinity, EC$_{50}$=144 nM (FIG. 1C). BTSA1 has a pyrazolone group substituted with a phenyl, a thiazolhydrazone and a phenylthiazol. BTSA1 complies with the Lipinski's rule of five for drug-likeness and is generated with a two-step synthetic protocol. Because BIM BH3 helix binds the BH3 groove of anti-apoptotic BCL-2 proteins and BAX, it was investigated whether BTSA1 binds selectively to BAX. Unlabeled BIM SAHB$_{A2}$ helix effectively competed FITC-BIM SAHBA2 binding to the structurally diverse members of the anti-apoptotic BCL-2 proteins, BCL-X$_L$, MCL-1 and BFL-1/A1. In contrast, BTSA1 had no capacity to compete FITC-BIM SAHB$_{A2}$ from anti-apoptotic BCL-2 proteins at 50 µM, showing specificity for BAX and excluding nonspecific reactivity for BTSA1 (FIG. 1D).

NMR analysis of $^{15}$N-labeled full-length BAX upon BTSA1 titration revealed backbone amide chemical-shift changes consistent with BTSA1 binding reversibly to residues of the BAX trigger site (FIG. 1E-1F). Molecular docking driven by the NMR data, determined a lowest-energy pose for BTSA1 that is also consistent with the observed chemical shifts upon BTSA1 binding to BAX (FIG. 1G). BTSA1 is calculated to bind in the hydrophobic region at the juxtaposition of helices α1 and α6 formed by M20, K21, A24, L25, Q28, G138, L141, and R145 residues (FIG. 1H). BTSA1 mimics features of the binding pose of the BIM BH3 helix (FIG. 1I). Interestingly, the phenyl ring attached to the pyrazolone is in close proximity with the α1-α2 loop of BAX in its open conformation. This phenyl ring provides significant increase in potency as a BTSA1 analogue, BTSA2, that has the same structure but a methyl instead of a phenyl, displayed moderate binding affinity ($IC_{50}$=3.7 µM). To gain further insights, molecular dynamics (MD) simulations were performed of the BTSA1-bound and unbound BAX. BTSA1 retained its bound position during the MD trajectory and also the α1-α2 loop maintained an open conformation from interactions with the BTSA1; a feature that was shown to be essential for BAX activation and consistent with the exposure of the epitope (residues 12-24) that is recognized by the 6A7 antibody only upon BAX activation (Garner et al., 2016; Gavathiotis et al., 2010). In contrast, unbound BAX kept the α1-α2 loop in closed conformation during the MD trajectory. Taken together, BTSA1 binds with high affinity to BAX at a critical region associated with BAX activation, which is consistent with the high binding selectivity for BAX.

Figures 2A, 2B, 2C, 2D, 2E, 2F, 2G, 2H:
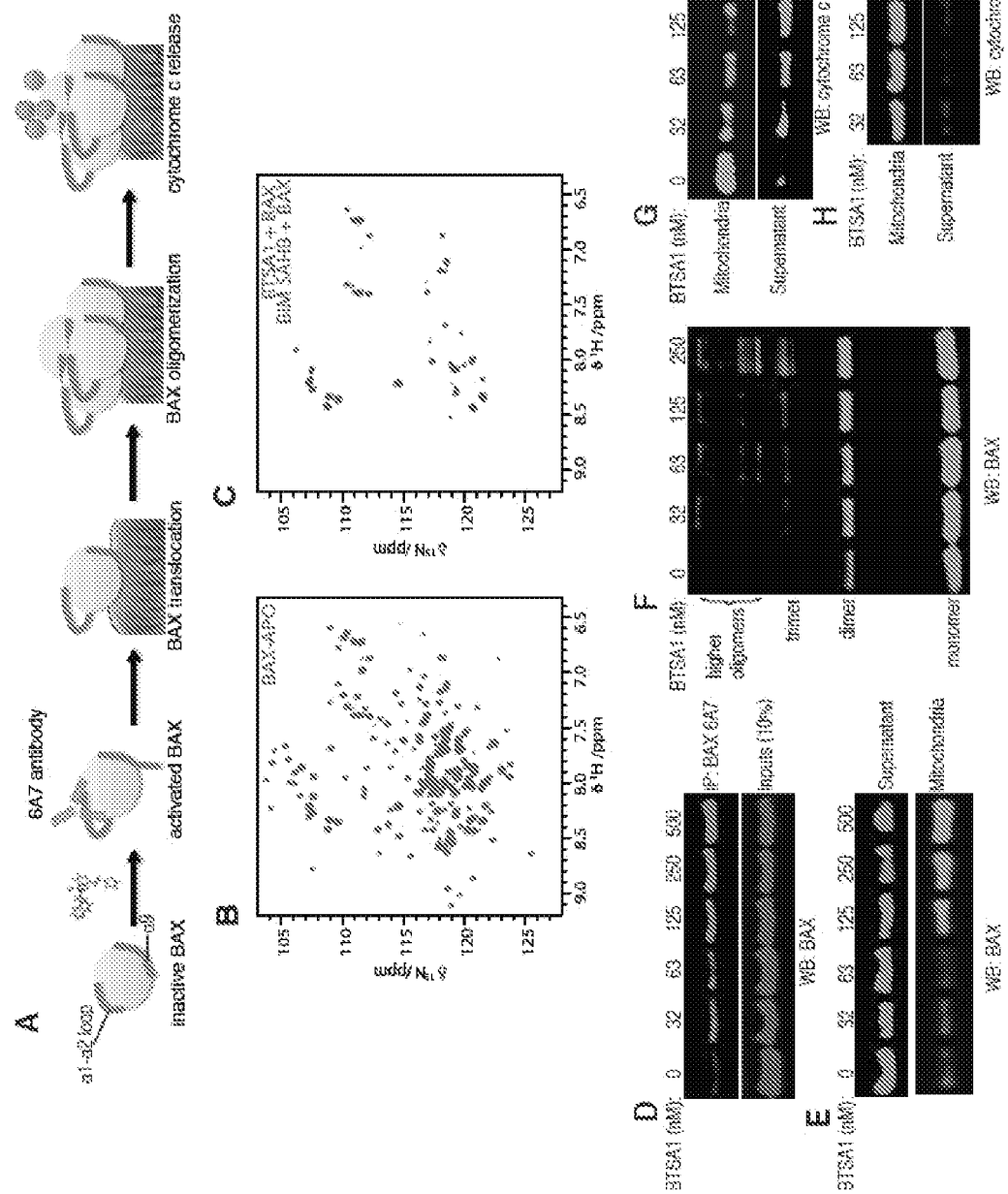
FIG. 2A-2H. BTSA1 induces all steps of the BAX activation pathway. (A) Cartoon representation of each step toward BTSA1-induced BAX activation leading to mitochondrial permeabilization. (B) $^1$H-$^{15}$N HSQC spectra of unbound and inactive BAX. (C) Overlaid $^1$H-$^{15}$N HSQC spectra of BAX activated by BTSA1 or BIM SAHB$_{A2}$ shows the formation of the same BAX oligomers. The appearance of several amide correlation cross peaks originates from the significant increase of the large size of the BAX oligomers. (D) BTSA1-induced exposure of the N-terminal BAX activation epitope recognized by the 6A7 antibody in an immunoprecipitation assay. BTSA1-induced BAX translocation (E), BAX oligomerization (F), and BAX-mediated cytochrome c release (G) upon BTSA1 titration with recombinant soluble BAX using isolated mitochondria. (H) No cytochrome c release in the absence of BAX upon BTSA1 titration. Data are representative of three independent experiments respectively.

Upon BH3-mediated activation, BAX undergoes conformational changes that transform the inactive cytosolic monomer into a mitochondrial oligomer capable of mitochondrial permeabilization (FIG. 2A) (Bleicken et al 2014; Czabotar et al., 2013; Gavathiotis et al., 2010; Zhang et al., 2015). Remarkably, BTSA1 binding to inactive and soluble BAX progressively leads to BAX oligomerization as evidenced by the disappearance of the BAX monomer in Heteronuclear Single-Quantum Correlation (HSQC) spectra and size-exclusion chromatography (SEC) trace and appearance of the corresponding BAX oligomer HSQC spectra and SEC trace (FIG. 2B, 2C). Using the conformation-specific antibody 6A7 that recognizes the exposure of the BAX activation epitope, BTSA1 potently exposed the 6A7 epitope of recombinant BAX consistent with the functional activation of BAX and structural model of BTSA1-bound BAX (FIG. 2D, 1H). The binding of BTSA1 to BAX was investigated in the presence of isolated mitochondria from mouse liver that contain no BAX or BAK. BTSA1-binding to recombinant BAX potently and dose-responsively induced mitochondrial membrane translocation of soluble BAX to mitochondrial membrane, which was followed by BAX oligomerization (FIG. 2E, 2F). Consistently, BTSA1-induced BAX activation resulted in mitochondrial outer membrane permeabilization and release of cytochrome c from mitochondria (FIG. 2G). BTSA1 had no effect on mitochondria in the absence of BAX (FIG. 2H). Taken together, the biophysical, structural and biochemical data demonstrate that BTSA1's high affinity and specific binding to the BAX trigger site leads to functional and effective BAX activation.

BTSA1-Induced BAX Activation Induces Apoptosis in Cancer Cells

Figures 3A, 3B, 3C, 3D, 3E, 3F, 3G, 3H, 3I, 3J:
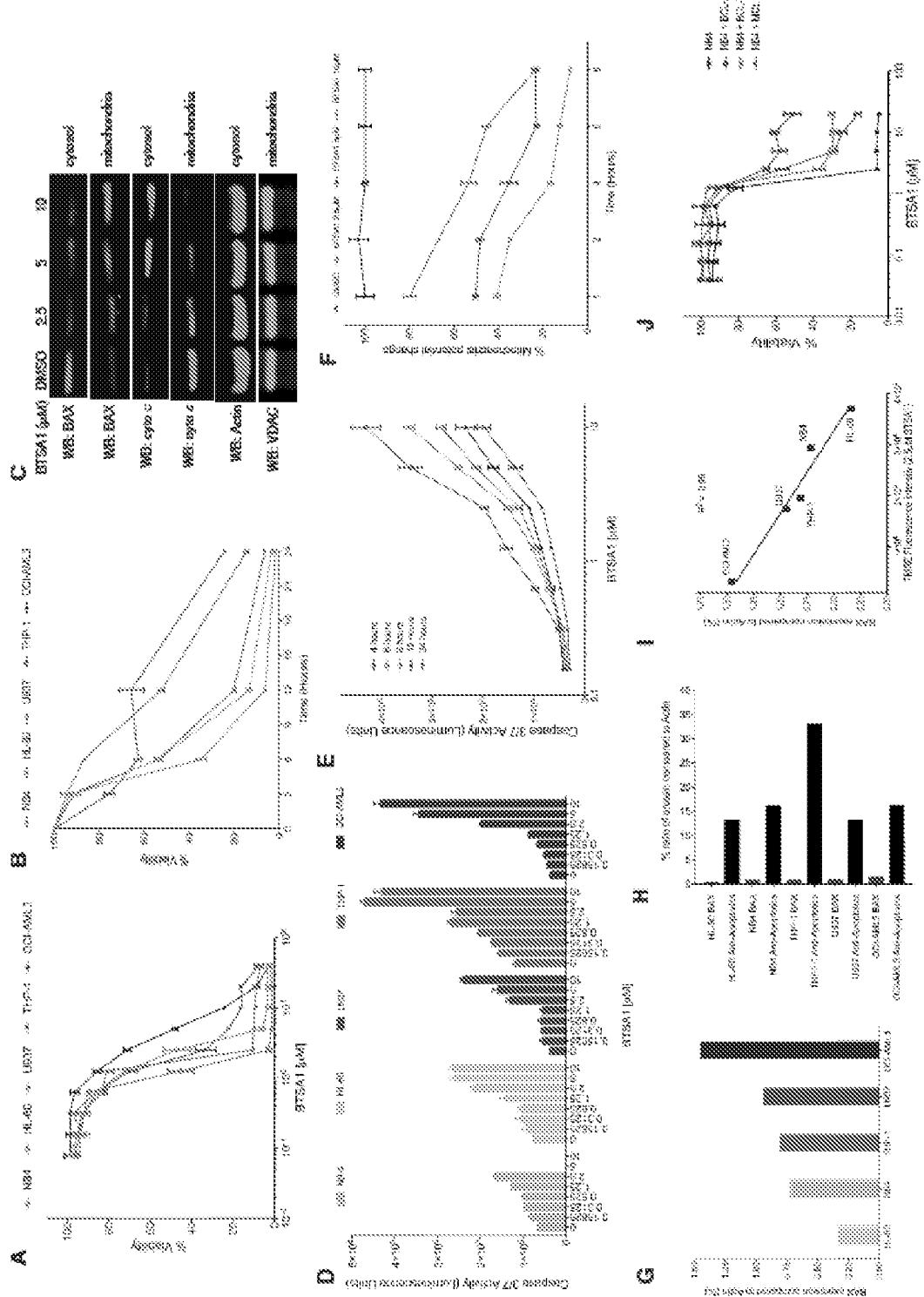
FIG. 3A-3J. BTSA1 induced robust and rapid BAX-mediated apoptosis. (A) Viability assay of AML cell lines exposed to BTSA1 for 24 hrs or (B) 5 μM BTSA1 for 6, 12 and 24 hrs. (C) Western blot analysis of BAX translocation and cytochrome c release from NB4 cells treated with BTSA1 for 6 h. Actin and VDAC are loading controls for cytosolic and mitochondrial fractions respectively. (D) Caspase 3/7 assay in AML cells treated with BTSA1 for 6 hrs. (E) Caspase 3/7 assay in OCI-AML3 cells treated with BTSA1 at 4, 6, 8, 12 and 24 hrs. (F) TMRE mitochondrial potential assay in OCI-AML3 cells treated with serial dilution doses of BTSA1 at indicated time points. (G) Percent BAX expression levels relative to Actin as measured by quantitative IR fluorescence western for five AML cell lines. (H) Percent expression level of BAX, BCL-2, BCL-XL and MCL-1 relative to Actin as measured by quantitative IR fluorescence western for five AML cell lines. (I) Linear correlation of percentage of BAX expression levels relative to Actin for the five AML cell lines with the amount of mitochondrial depolarization detected at 2 hrs with 2.5 μM BTSA1. (J) Viability assay of BTSA1-treated NB4 cells and NB4 cells over-expressing BCL-2, BCL-XL and MCL-1 proteins. Data represent mean±SD (n=3) from three independent experiments or are representative of three independent experiments.

The BCL-2 protein family regulates apoptosis in hematologic malignancies, which are characterized by defective apoptosis and oncogenic alterations that promote cell growth (Reed et al., 2008). The ability of BTSA1 to induce apoptosis was evaluated in human acute myeloid leukemia cell lines that have p53 and/or NRAS mutations and a range of expression levels for BAX and anti-apoptotic BCL-2 proteins: HL60, THP-1, NB4, OCI-AML3 and U937. Remarkably, BTSA1 reduced viability of all five AML cell lines in a dose-dependent manner with mean effective concentration ($EC_{50}$) values ranged between 1-4 µM that leads to complete killing within 24 h treatment (FIG. 3A). Cellular viability measured at different time points displayed substantial cell death activity by BTSA1 within 6 h of treatment (FIG. 3B). The substantial and rapid loss of viability of leukemia cells is consistent with the biochemical effects that characterize BAX activation and apoptosis, which was observed promptly after BTSA1 treatment. Significant BAX mitochondrial translocation was induced in a BTSA1 dose-dependent manner (FIG. 3C). BTSA1-induced BAX translocation coincided with the release of cytochrome c from the mitochondria to the cytosol (FIG. 3C). BTSA1 induced dose-dependent caspase-3/7 activation in all five AML cell lines (FIG. 3D). Caspase-3/7 activation was monitored within 4-24 hours and maximal caspase-3/7 activation was detected in 4 hours consistent with prompt BAX translocation and release of cytochrome c (FIG. 3E).

A more direct consequence of the BTSA1 activity is considered to be the loss of mitochondrial membrane potential that can be caused by BAX mitochondrial translocation. Consistently, significant mitochondrial potential loss occurred within 2 h and in a dose-responsive manner upon BTSA1 treatment (FIG. 3F). To investigate the correlation of the BTSA1 activity to BAX and mitochondrial apoptosis, the protein levels of BAX, BCL-2, BCL-XL and MCL-1 were measured and compared to actin by an infrared-based quantification method (FIG. 3G, 3H). Interestingly, a linear response was found with BAX protein levels and the degree of mitochondrial membrane potential loss induced by BTSA1, suggesting that mitochondrial damage induced by BTSA1 is proportional to BAX levels in leukemia cells (FIG. 3I). There is no correlation of BTSA1 activity and levels of anti-apoptotic BCL-2 proteins consistent with its specificity to BAX (FIG. 3H). The protein levels for BCL-2, BCL-XL and MCL-1 were consistently higher in the AML cell lines compared to BAX (FIG. 3H). Moreover, transient overexpression of BCL-XL, BCL-2 and MCL-1 decreased cell killing from BTSA1-induced BAX activation, consistent with the established mechanism of action for heterodimeric blockade of BAX (FIG. 3J). Taken together, BTSA1 induces robust apoptosis in leukemia cells through rapid BAX activation, which both overcomes the endogenous expression of anti-apoptotic BCL-2 proteins and directly correlates with BAX protein levels.

Figures 4A, 4B, 4C, 4D, 4E, 4F, 4G, 4H, 4I, 4J:
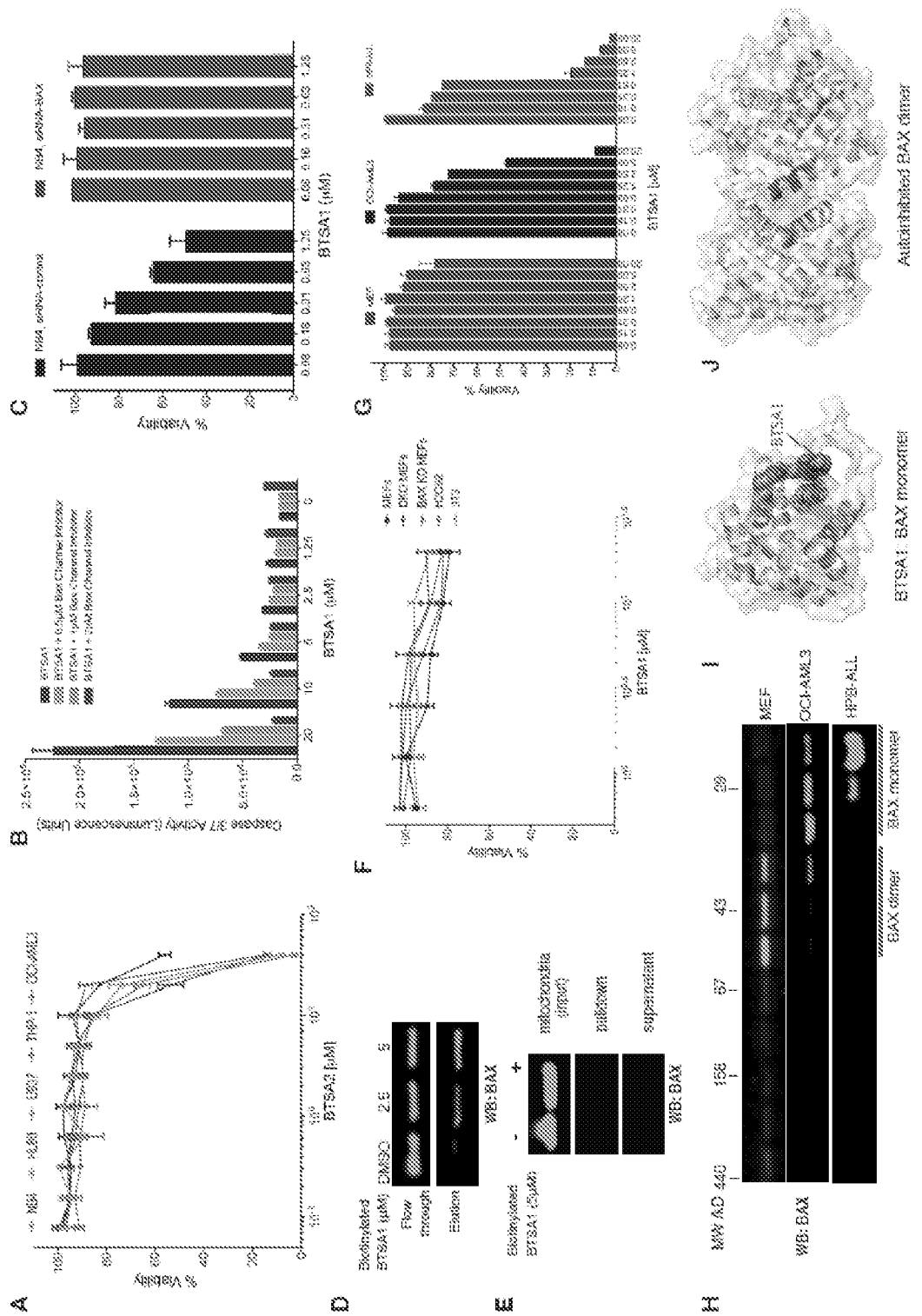
FIG. 4A-4J. BTSA1 specifically targets cytosolic BAX conformation primed for activation to induce selective apoptosis in leukemia cells. (A) A weaker BAX activator, BTSA2, has markedly reduced potency in killing AML cell lines compared to BTSA1 (B) Caspase 3/7 assay of BTSA1-treated NB4 cells exposed to a BAX channel inhibitor. (C) Viability assay of BTSA1-treated NB4 cells silenced for BAX expression using BAX siRNA. (D, E) Western blot analysis of BAX from pulldown assay using biotinylated BTSA1 exposed to cytosolic fractions or mitochondrial fractions, respectively, of OCI-AML3. (F) Viability assay of non-cancerous cell lines treated with BTSA1. (G) Viability assay of OCI-AML3, HPB-ALL and MEFs cells treated with BTSA1. (H) Size-exclusion chromatography (Superdex 200, HR 10/30) of cytosolic extracts from MEF, OCI-AML and HPB-ALL. Fractions corresponding to increasing elution volumes from left to right and indicated molecular weights were analyzed by anti-BAX western blot. HPB-ALL contained monomeric BAX, OCI-AML contained predominantly monomeric BAX and MEF have no detected monomeric BAX. (I) Structural model of BAX monomer showing BTSA1 docked to the trigger site. (J) Crystal structure of autoinhibited cytosolic BAX dimer showing the trigger site residues blocked from residues of another BAX molecule within the dimer. Data represent mean±SD (n=3) from three independent experiments or are representative of three independent experiments.

BTSA1 Cell Killing is Specific to BAX and is Regulated by BAX Cytosolic Conformation Since BAX is found at the nexus of several signaling pathways, cellular specificity of BTSA1 to directly induce BAX activation was investigated. Firstly, the weaker analogue BTSA2 was used. The reduction in binding capacity to BAX (~10 fold) resulted in a similar reduction in cell death induction in all AML cell lines (FIG. 4A). Moreover, BTSA1-mediated apoptosis was prevented with a pharmacological inhibitor of the BAX mitochondrial associated channel, which resulted in complete inhibition as measured by caspase-3/7 activation (FIG. 4B) (Bombrun et al., 2003). Likewise, genetic knockdown of BAX using an siRNA for BAX markedly reduced cell death activity of BTSA1 (FIG. 4C). Finally, direct engagement of BTSA1 with BAX in cells was investigated. Using the structural model of BTSA1 bound to BAX, a biotin group was attached to a BTSA1 analogue with a carboxylic acid at the phenylthiazol group and a hydrophilic linker of an appropriate size. The biotinylated BTSA1 retained binding to recombinant BAX although binding affinity was reduced ten-fold ($IC_{50}$=2 µM). Biotinylated BTSA1, at 2.5 µM dose, binds to cellular BAX and preferentially binds to cytosolic BAX but not to BAX associated with the mitochondrial outer membrane, consistent with BTSA1 targeting the BAX trigger site that is only available in the cytosolic BAX conformation (FIG. 4D, 4E) (Gavathiotis et al., 2008; Kim et al., 2009). Moreover, biotinylated BTSA1 failed to pull down other anti-apoptotic BCL-2 family proteins, confirming the selectivity to targeting BAX in cells. Thus, these data provide strong evidence for the cellular specificity and on-target engagement of BTSA1.

Non-leukemia cell lines that have no BAX expression such as mouse embryonic fibroblasts Bax$^{-/-}$ (BAX KO) MEF and doubly Bax$^{-/-}$/Bak$^{-/-}$ (DKO) MEF, were treated with BTSA1 and exhibit resistance to BTSA1 treatment (FIG. 4F). The insensitivity of BAX KO and DKO MEF demonstrate the specificity of BTSA1 activity for BAX. However, additional cells that express BAX such as wild type MEF, H9c2 myocytes and 3T3 fibroblasts still exhibit resistance to BTSA1 treatment at similar doses that BTSA1 induces complete levels of cell death in AML cells (FIG. 4F). To further investigate the resistance to BTSA1 treatment, it was tested whether BTSA1 can promote BAX activation in wild type MEF. BTSA1 had no capacity to induce BAX translocation, suggesting that the ability of BTSA1 to activate BAX is suppressed. Cytosolic BAX can form an autoinhibited dimeric conformation that regulates sensitivity to BAX activation and BAX-dependent apoptosis (Garner et al., 2016). Thus, an analysis was performed of the conformation of BAX present in cytosolic extracts of wild type MEF, OCI-AML and HPB-ALL cells that display different sensitivity to BTSA1-induced killing (FIG. 4G). Consistently, OCI-AML3 and HPB-ALL cells have cytosolic BAX in monomeric conformation in contrast to MEF that have cytosolic BAX in dimeric conformation. Thus, leukemia cells' sensitivity to BTSA1-induced BAX activation is consistent with the ability of BTSA1 to bind the BAX trigger site, which is readily available in the BAX monomer (FIG. 4I). In contrast, the autoinhibited dimeric BAX in cells such as MEF prevents prompt BAX activation by BTSA1 (FIG. 4J).

BTSA1 Kills Primary AML Samples and Spares Healthy Cells

Figures 5A, 5B, 5C, 5D, 5E, 5F:
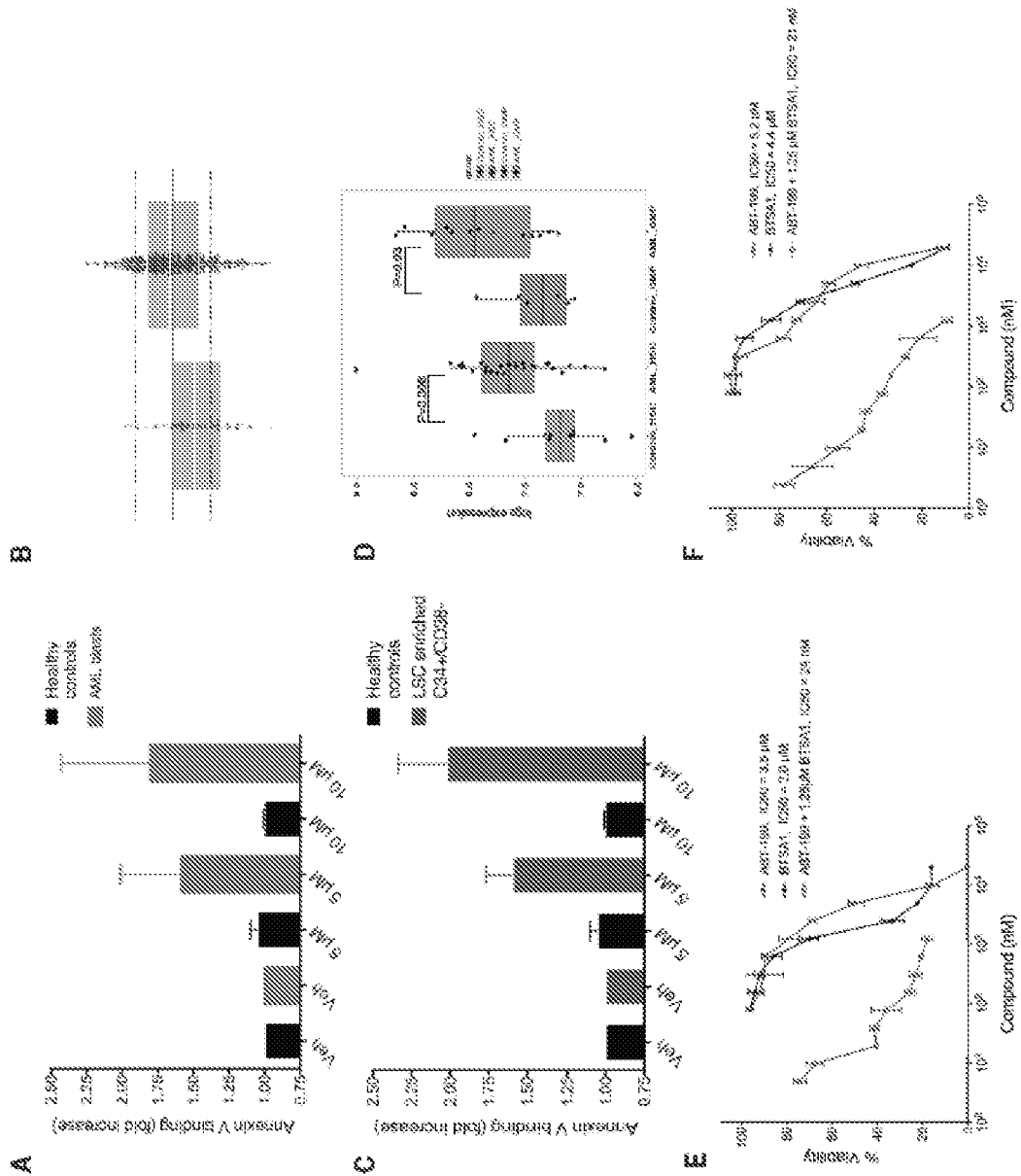
FIG. 5A-5F. BTSA1 is effective against patient AML blasts and pre-leukemic stem cells without affecting normal hematopoietic progenitor cells and demonstrates significant synergy with venetoclax. (A) BTSA1 induced apoptosis (indicated by Annexin V positivity) in primary human AML blasts (n=4), but not in healthy control stem and progenitors cells (n=2). (B) BAX mRNA expression in AML patients cells (N=542) and healthy control cells (N=74) indicates significantly (p=3.26×10-07) higher expression of BAX in AML. (C) BTSA1 induced apoptosis in primary human CD34+CD38− (stem cell-enriched) AML cells (n=4), but not in healthy CD34+CD38-cells (n=2) exposed to BTSA1. (D) BAX mRNA expression in highly purified stem cells (CD34+, CD38−, Lin−) and progenitor cell populations (Granulocytic Macrophage Progenitors, GMPs, (Lin−, CD34+, CD38+, CD123+, CD45RA+) from AML patients and healthy controls. Viability assay of THP-1 (E) or OCI-AML3 (F) cells treated with venetoclax (ABT-199) or BTSA1 alone or in combination after 24 hrs treatment.

To evaluate the translational potential of BTSA1-induced BAX activation, BTSA1 was tested in primary samples from patients with high-risk AML. Strikingly, BTSA1 induced dose-dependent apoptosis in primary AML blast cells but not in healthy hematopoietic stem cells and progenitors (FIG. 5A). Consistent with BTSA1 activity, human AML cells obtained from patients demonstrate higher expression of BAX compared to healthy controls (FIG. 5B). BCL-2 protein, but not BCL-XL or MCL-1, has also higher expression in AML patients, supporting the sensitivity of BTSA1 in AML cells and suggesting BCL-2 as the major anti-apoptotic block for BTSA1-induced BAX activation. Remarkably, BTSA1 is also effective in leukemic stem cell-enriched fractions (CD34+CD38−) from these high-risk AML patients (FIG. 5C). In contrast, the same dosages of BTSA1 did not affect apoptosis of primary bone marrow CD34+ CD38− cells from healthy donors (FIG. 5C). Highly purified stem and progenitor cell populations from AML patients demonstrated higher expression of BAX when compared to healthy counterparts (Barreyro et al., 2003; Schinle et al., 2015) consistent with BTSA1 activity in pre-leukemic stem cells (FIG. 5D). In addition, similar analysis indicated higher expression for MCL-1, but not for BCL-2 or BCL-XL, in pre-leukemic stem cells from AML patients, indicating a favorable expression profile for selective killing by BTSA1. Taken together, the data demonstrate a significant killing selectivity for BTSA1-induced BAX activation in human AML blasts and pre-leukemic stem cells compared to healthy stem and progenitor cells, which is consistent with the observed elevation of BAX expression levels in human AML.

Comparative expression analysis of AML blasts compared to healthy controls demonstrated upregulation of BAX and BCL-2 upregulation in AML (FIG. 5B). It was hypothesized that BTSA1 would potentiate venetoclax, a BCL-2 protein inhibitor that is currently in clinical trials for AML. venetoclax and BTSA1 were tested in several AML cell lines that display similar susceptibility. When both drugs are evaluated in combination, BTSA1 at ~$EC_{10}$ dose displayed significant synergy with venetoclax increasing its $EC_{50}$ to low nM concentration from the low M range (FIG. 5E, 5F). Moreover, the synergistic effect of these two drugs is observed within hours, consistent with their kinetics of mitochondrial apoptosis activation. These results suggest that direct BAX activators such as BTSA1 can be an effective therapeutics for AML as monotherapy and in combination with BCL-2 inhibitors could have more potent and broader activity in AML (Goff et al., 2013; Lagadinou et al., 2013; Pan et al., 2014).

BTSA1 Suppresses Human AML Xenografts and is Well Tolerated

Figures 6A, 6B, 6C, 6D, 6E:
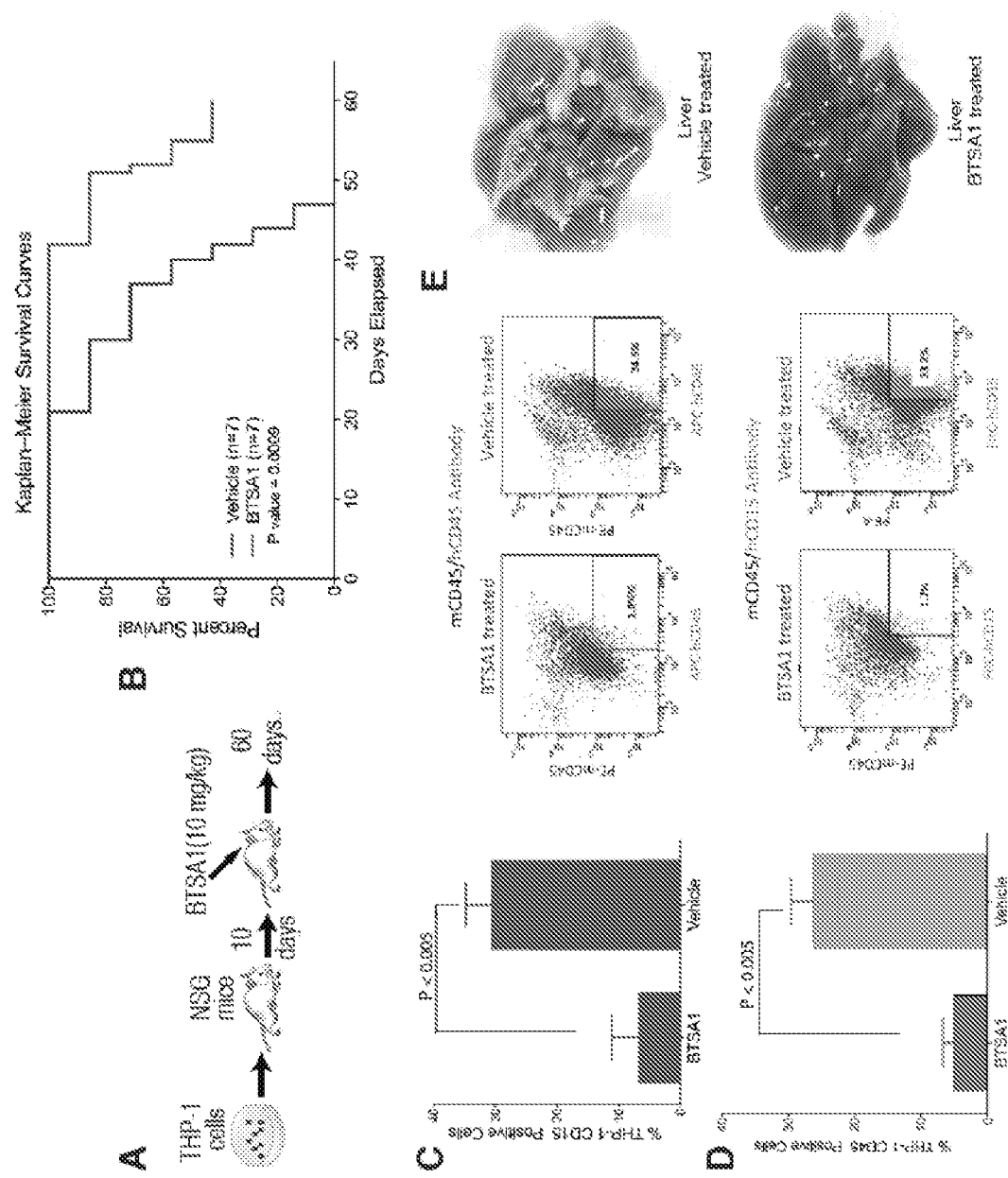
FIG. 6A-6E. BTSA1 demonstrates potent efficacy in killing human AML in vivo. (A) Schematic of the THP-1 xenograft mouse model experiment. (B) Kaplan-Meir survival curves of vehicle- and BTSA1-treated cohorts. (C, D) FACS analysis of tumor burden using mouse and human CD45 antibody or mouse CD45 antibody and human CD15 antibody from vehicle- and BTSA1-treated cohorts. (E) An example of liver infiltrates from a vehicle- and BTSA1-treated mice.
Figures 7A, 7B, 7C, 7D, 7E:
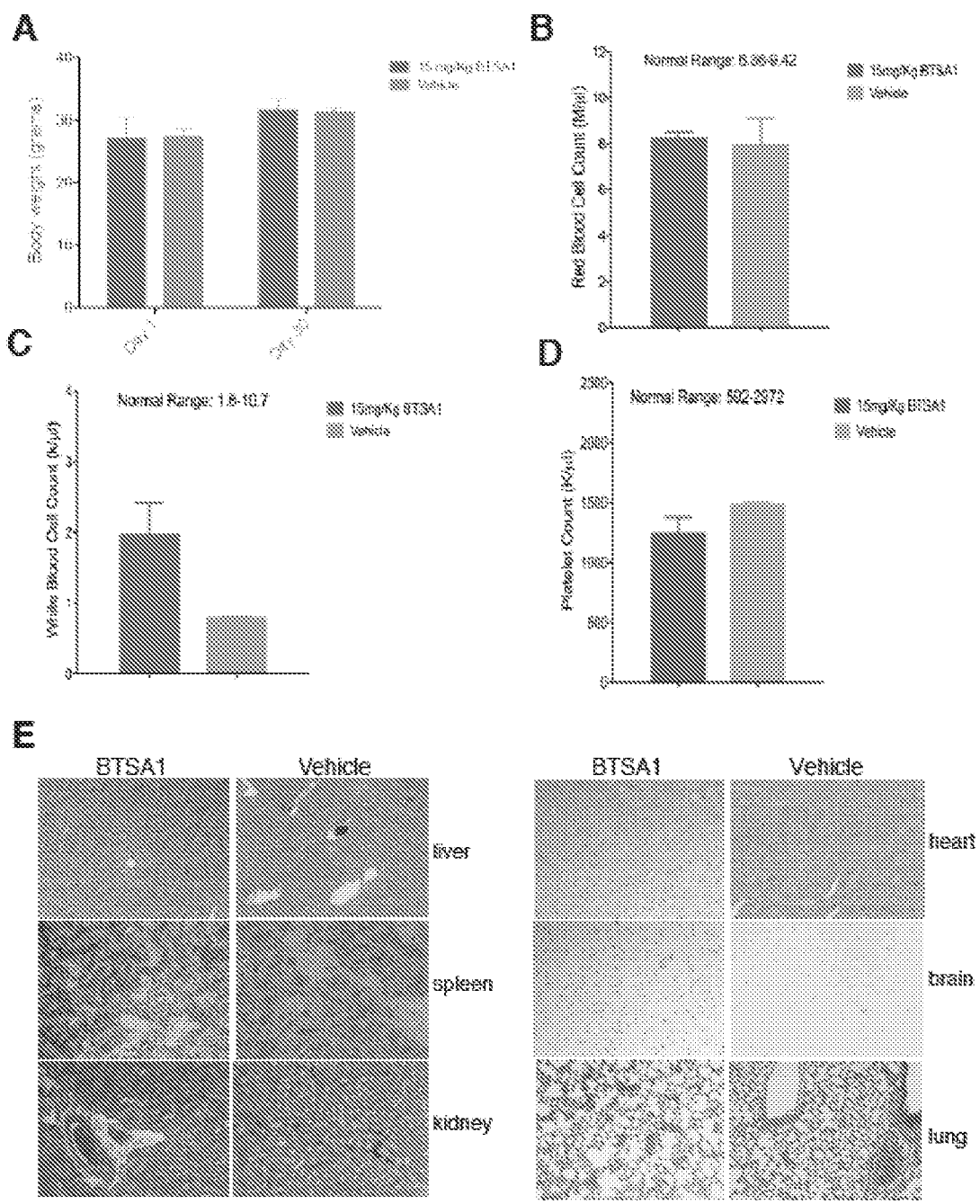
FIG. 7A-7E. BTSA1 is well tolerated without toxicity to normal cells in vivo. Toxicology analysis of NSG mice treated for 30 days with 15 mg/kg BTSA1 per body weight or vehicle. (A) Body weight measurements on day 1 and after 30-days of treatment. (B-D) Counts of peripheral white blood cells, red blood cells and platelets within normal range in vehicle or 15 mg/kg BTSA1 per body weight treated mice after 30-days of treatment. (E) Representative tissue sections using Hematoxylin & Eosin staining of the indicated tissues from mice show no detectable nonspecific toxicity.

The in vivo activity of BTSA1-induced BAX activation was next evaluated for efficacy in human AML xenografts and safety in healthy cells and tissues. Pharmacokinetics studies in mice demonstrated that BTSA1 had an excellent stability in mouse plasma in vivo ($h_{1/2}$=15 h) and oral bioavailability (% F=51) while a 10 mg/kg dose reached sufficient levels (~15 µM) of BTSA1 to induce BAX activation and apoptosis in leukemia cells. Human leukemia THP-1 xenografts were generated in mice. After engraftment at 10 days, mice were randomly divided into two groups and treated with either vehicle or 10 mg/kg BTSA1 every 48 hours (FIG. 6A). Remarkably, mice treated with BTSA1 had significantly increased survival when compared to vehicle-treated mice (median survival 40 days in control vs 55 days in BTSA1-treated) and 43% of BTSA1-treated mice revealed complete resolution of leukemia (FIG. 6B). To confirm anti-leukemic efficacy of BTSA1, the experiment was repeated and after 3 weeks of BTSA1 treatment, AML tumor burden from bone marrow and liver was evaluated by flow cytometry using anti-hCD45 and anti-hCD15 antibodies. BTSA1 treatment induced significant suppression of human THP-1 leukemia growth (FIG. 6C, 6D). Consistently, in vehicle-treated mice, infiltrates of tumor cells were observed in the livers of mice while in BTSA1-treated mice these infiltrates were not detected (FIG. 6E). To evaluate tolerance of BTSA in vivo, a toxicology study was performed by treating mice for 30 days with a higher dose (15 mg/kg) of BTSA1 than that used in the efficacy study. Mice tolerated BTSA1 for the entire duration of treatment exhibiting normal behavior and no detectable toxicity was observed. Specifically, body weights before and after treatment showed no loss of weight (FIG. 7A). Blood counts of white blood cells, red blood cells and platelets were maintained at normal range and comparable to levels of vehicle-treated mice (FIGS. 7B-7D), and histological evaluation of several tissues showed no evidence of toxicity (FIG. 7E). Thus, BTSA1 is orally bioavailable with excellent pharmacokinetics, demonstrates significant anti-tumor activity in leukemia xenografts and at therapeutically effective doses it does not show any detectable toxicity in the hematopoietic system or normal tissues.

Studies with Other BAX Activator Compounds

Figure 8A:
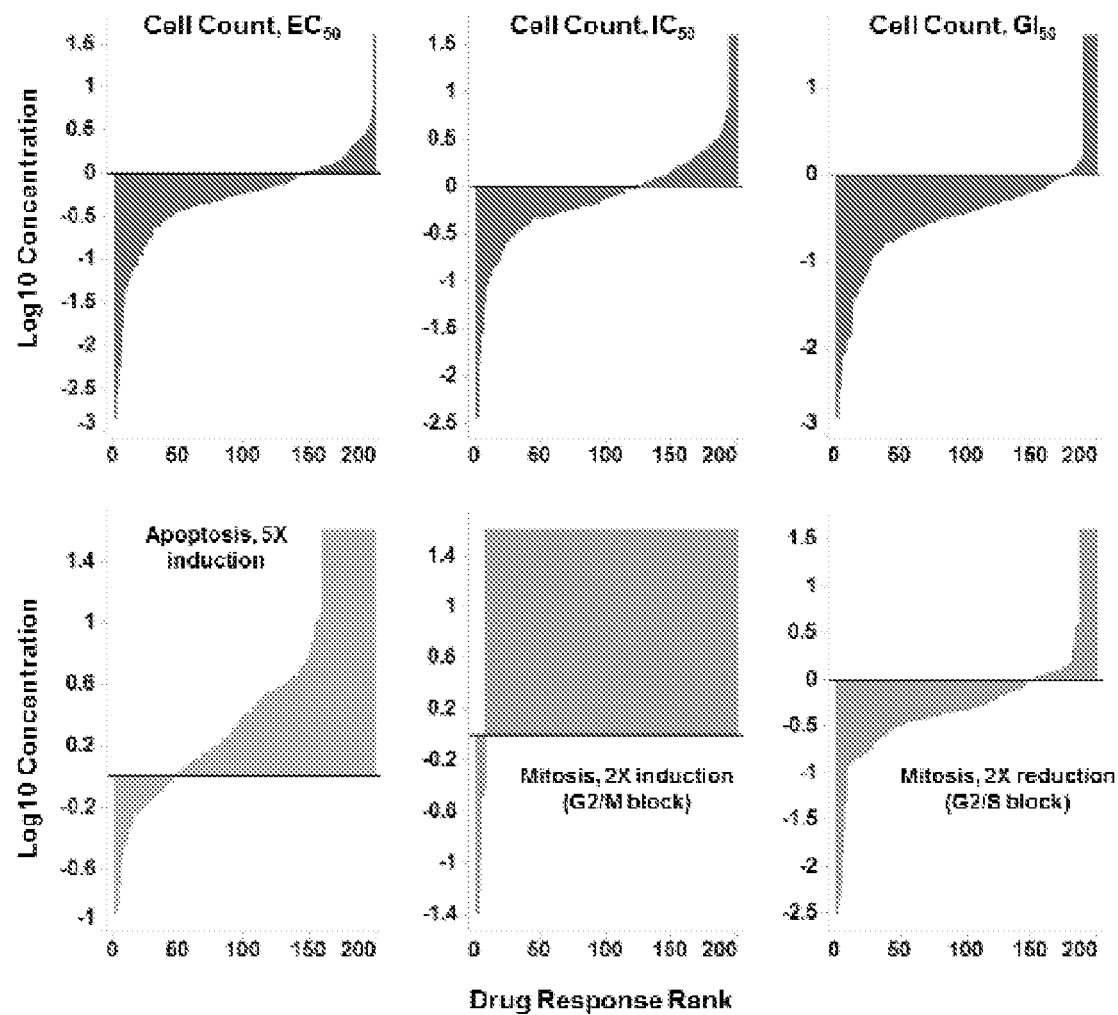
FIG. 8A-8D. Summary of data with compound GAV2-006 using 200 cancer cell lines. (A) Ranked drug response by measured parameter. Cellular response parameters (y-axis) vs. cellular response rank among tested cell lines (x-axis). Each bar represents an individual cell line. Cell count $EC_{50}$, $IC_{50}$, $GI_{50}$, apoptosis, mitosis induction and mitosis reduction are shown. (B) The pie chart on top shows the cancer types (site of primary tumor) represented by the cell lines in the OncoPanel™ profiling analysis. The legend to the right of each pie chart shows the count for each cancer type. The pie charts on the bottom show the breakdown of cancer subtypes within some of the larger types represented. (C) Box and whisker plot showing the distribution of log 10 $IC_{50}$ values from cell lines of represented cancer types. Black lines represent the average values. The top of the box represents the limit of the $1^{st}$ quartile (Q1), and the bottom of the box represents the $3^{rd}$ quartile (Q3) limit. Vertical lines show the limits of the data with the 95% confidence interval, and the circles represent outliers. Only the 18 most sensitive cancer types, by average $IC_{50}$, are shown. (D) Trellised pie charts showing the breakdown of cell lines classified as sensitive, resistant, or intermediate within each cancer type represented in OncoPanel™. Pie sizes are relative to the total number of cell lines for each tissue/tumor type.
Figure 8B:
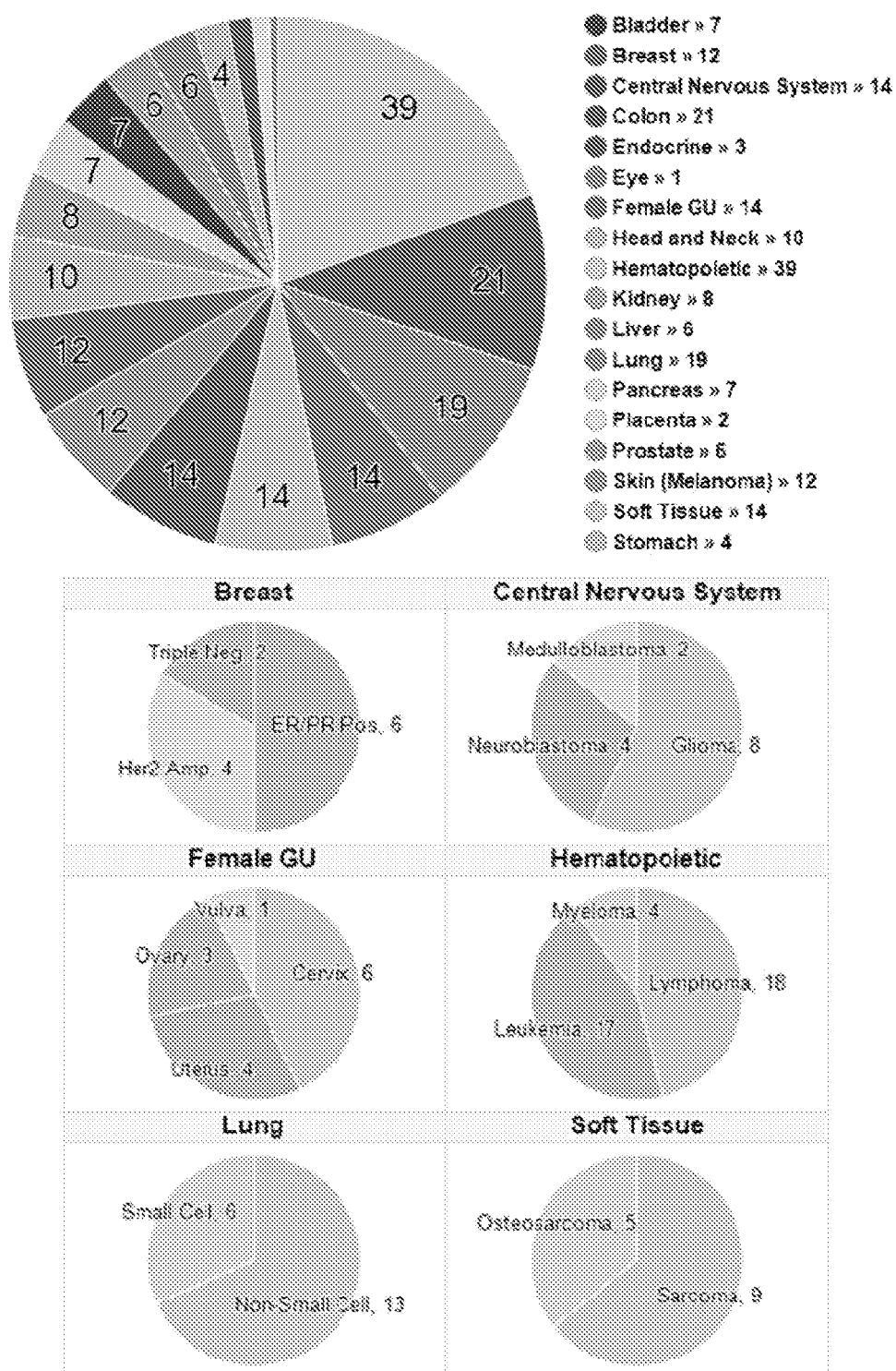
Figure 8C:
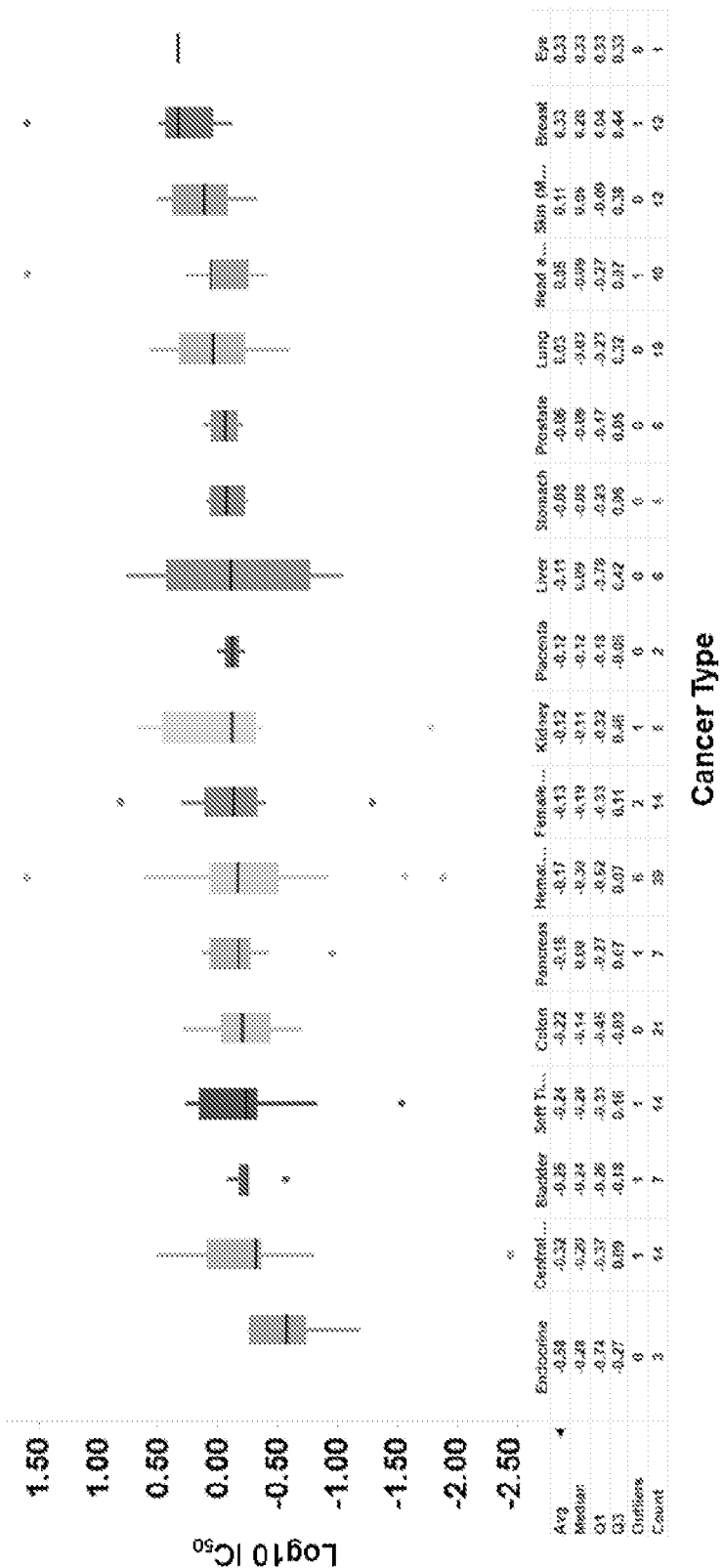
Figure 8D:
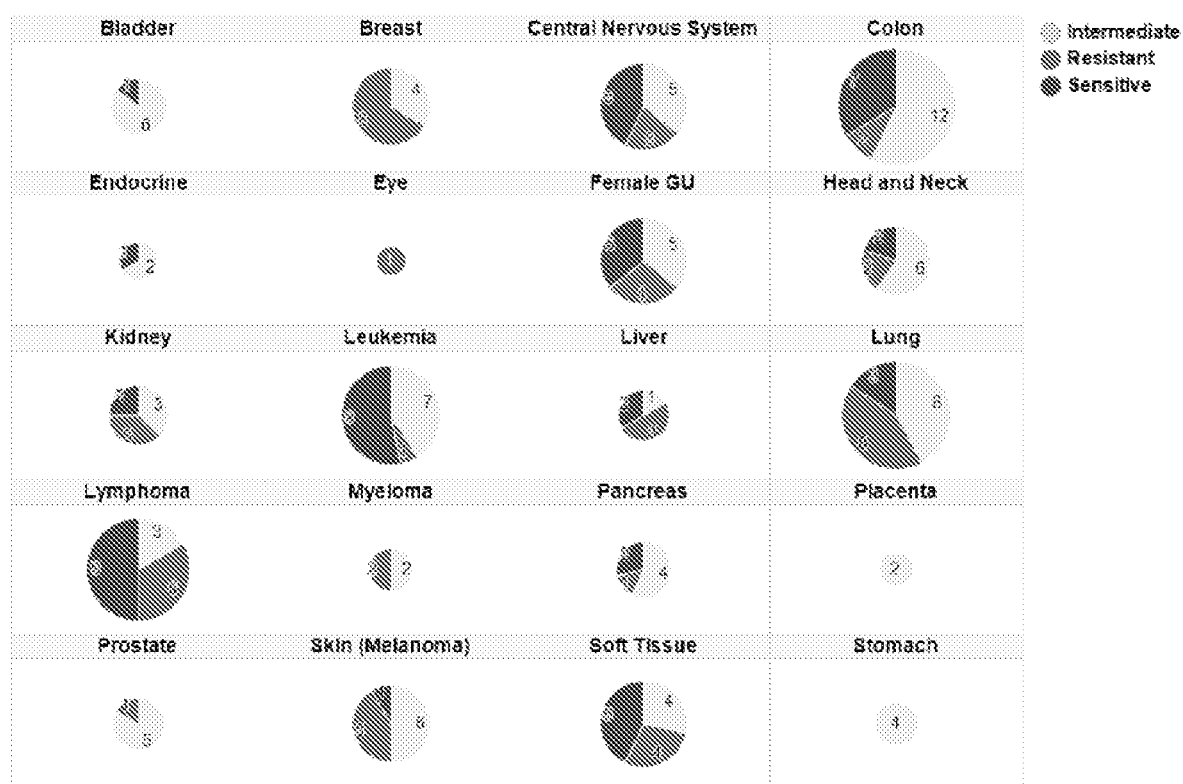
Figure 9:
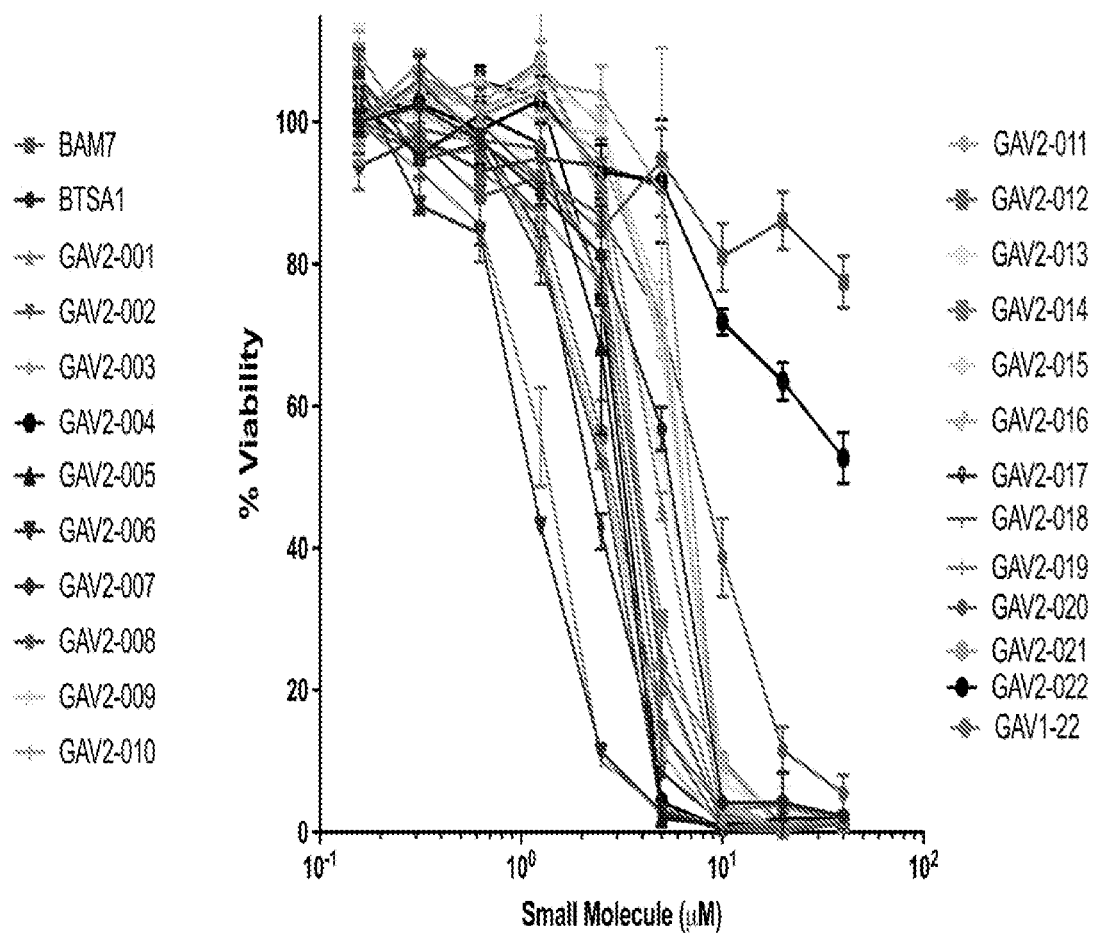
FIG. 9. Viability assay of human AML cell line OCI-AML3 exposed to various compounds for 48 hrs.
Figure 10:
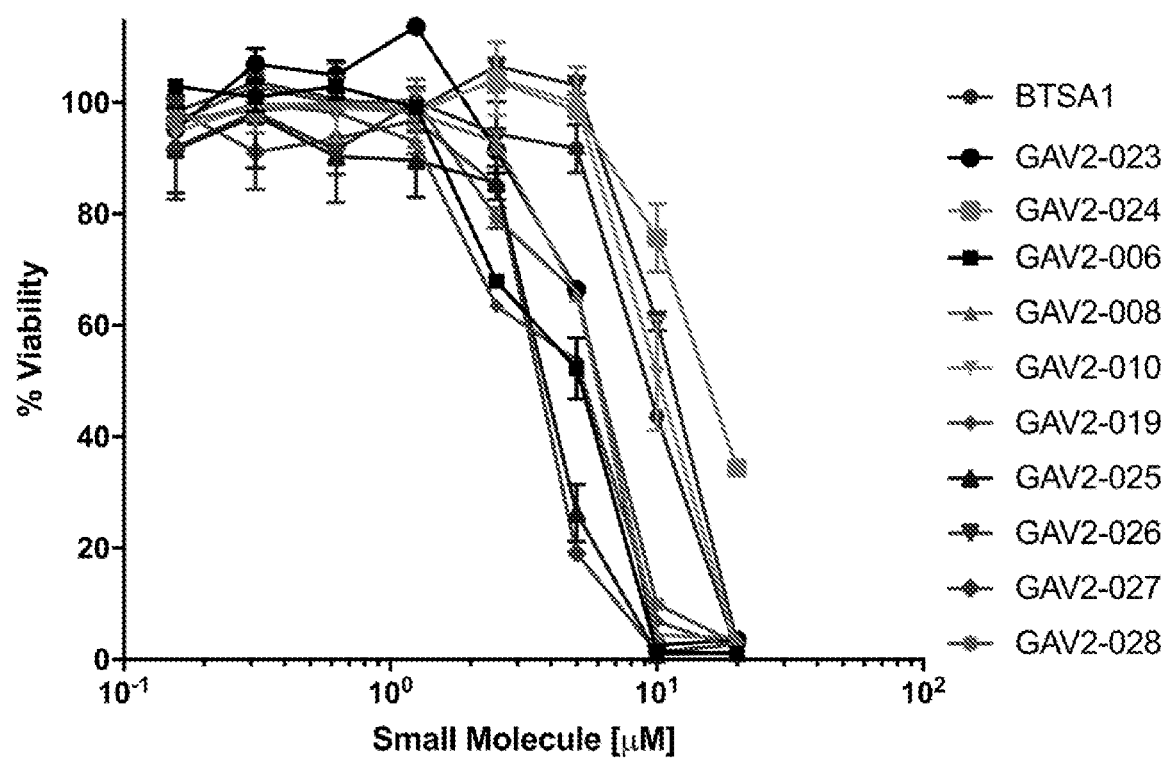
FIG. 10. Viability assay of human AML cell line OCI-AML3 exposed to various compounds for 48 hrs. Compounds GAV2-023-GAV2-028.
Figure 11A:
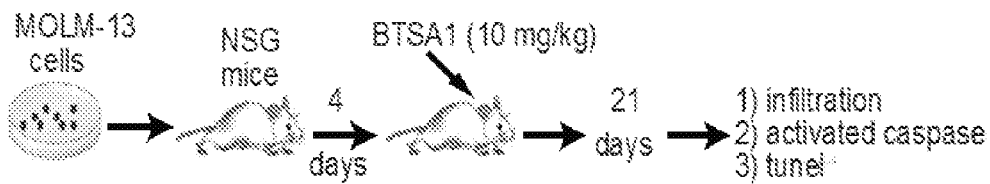
FIG. 11A-11I. Studies with MOLM-13 xenograft mouse model for analysis of human cell infiltrates and apoptosis markers and for mitochondrial TMRE assay experiment. (A) Schematic of MOLM-13 xenograft mouse model for analysis of human cell infiltrates and apoptosis markers. (B) FACS analysis of bone marrow infiltration using human and mouse CD45 and CD15 antibodies from vehicle- and BTSA1-treated cohorts (n=5). (C) FACS analysis of peripheral blood infiltration using mouse and human CD45 and human CD15 from vehicle- and BTSA1-treated cohorts (n=5). (D) Quantification of densitometric analysis for cleaved caspase-3 positive cells stained by IHC from bone marrow slides of vehicle- and BTSA1-treated cohorts (n=5). (E) Quantification of densitometric analysis for TUNEL positive cells stained by IHC in the bone morrow from vehicle- and BTSA1-treated cohorts (n=5). (F) Representative tissue sections from bone marrow using cleaved caspase-3 staining after treatment of vehicle and BTSA1. (G) Representative tissue sections from bone marrow using TUNEL staining after treatment of vehicle and BTSA1. (H) Schematic of MOLM-13 xenograft mouse model for mitochondrial TMRE assay experiment. (I) TMRE staining of mitochondria from human leukemia cells selected by human CD45 and CD15 antibodies from bone marrow of vehicle- and BTSA1-treated cohorts (n=5).
Figure 11B:
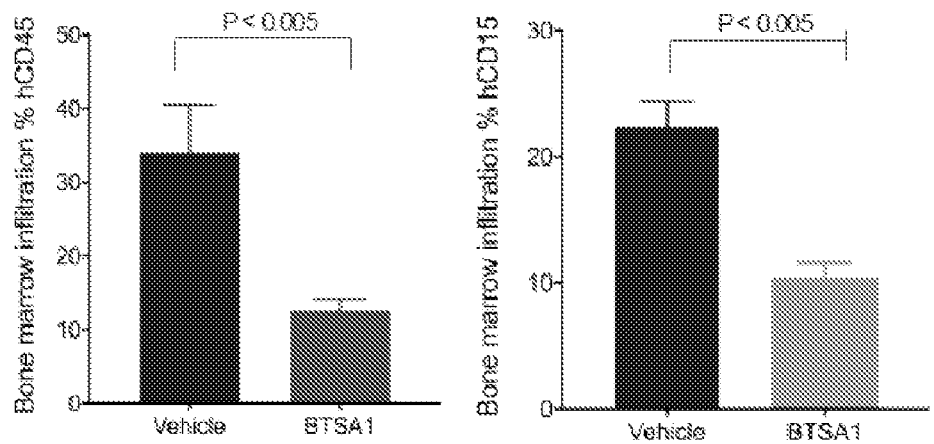
Figure 11C:
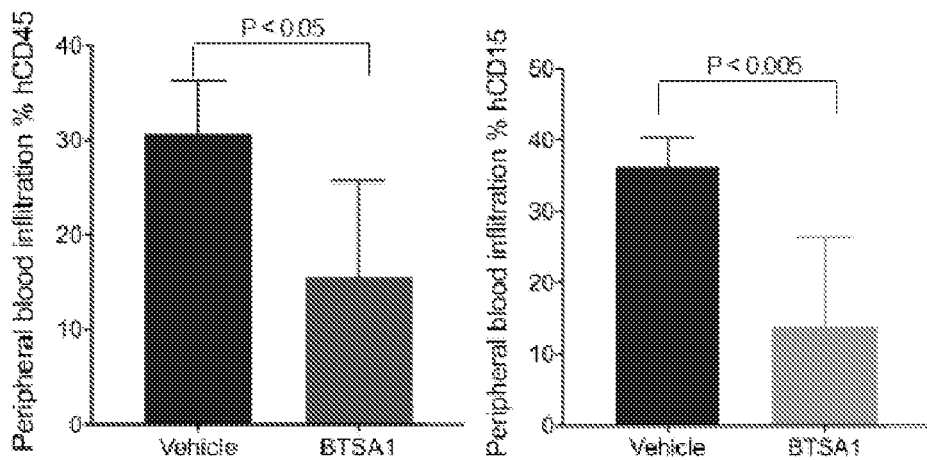
Figure 11D:
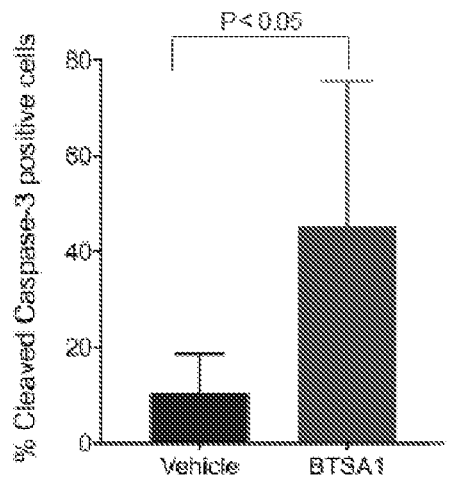
Figure 11E:
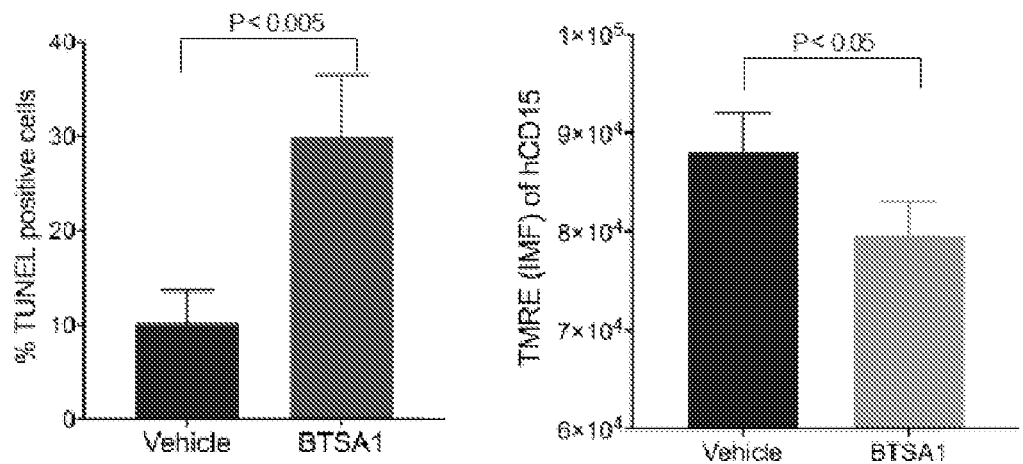
Figure 11F:
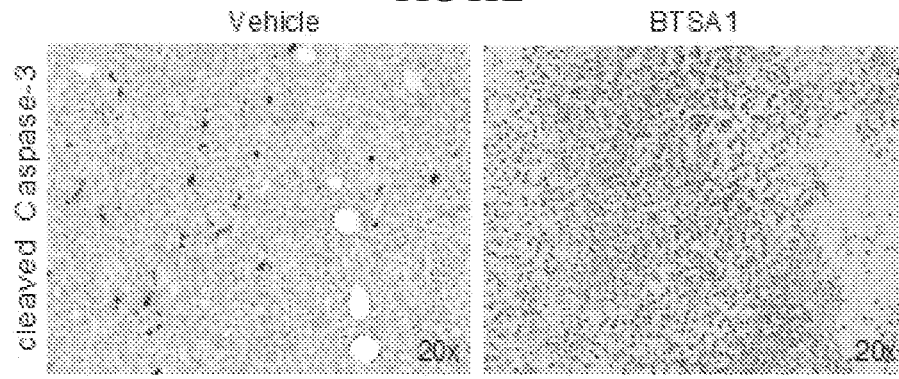
Figure 11G:
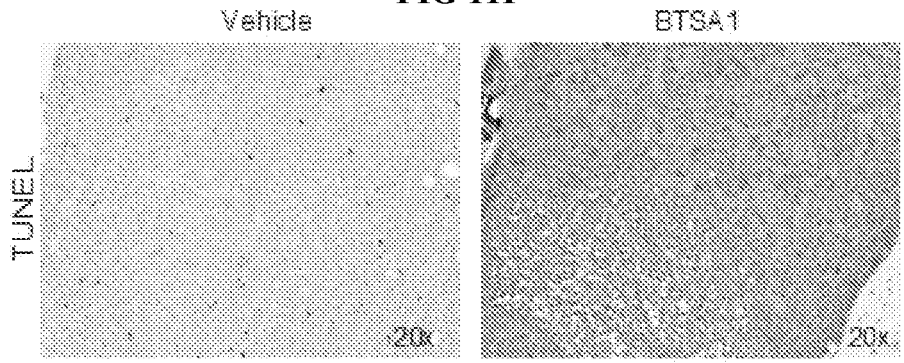
Figure 11H:
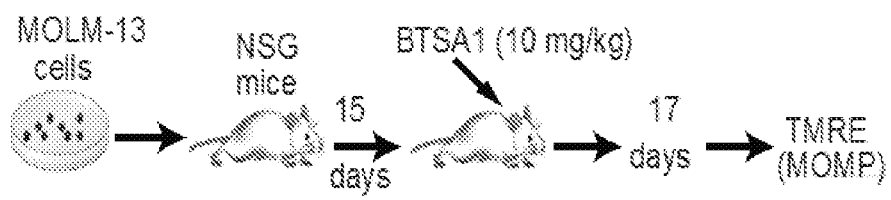
Figure 11I:
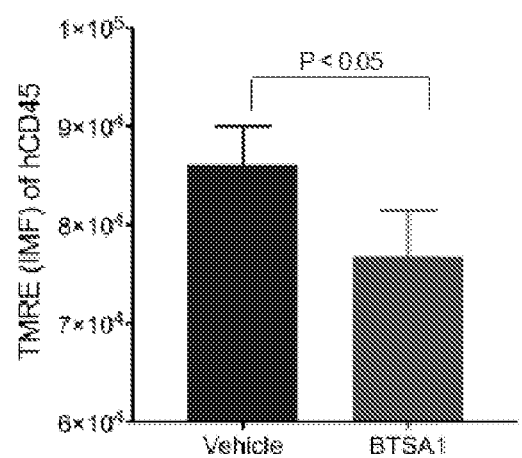
Figure 12A:
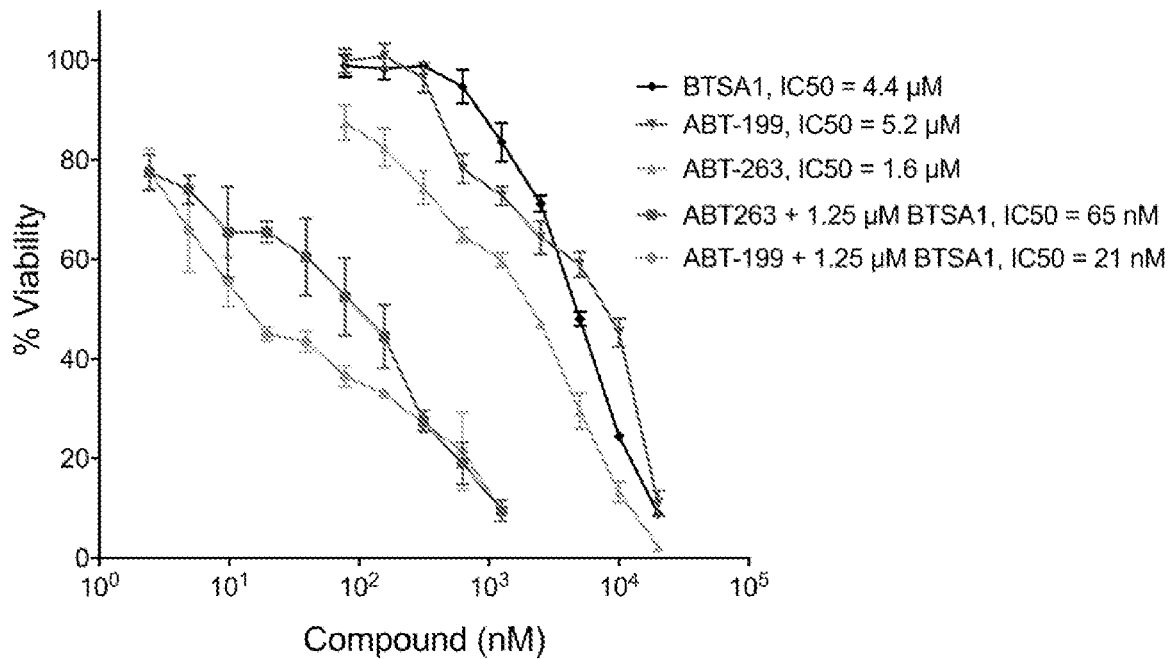
FIG. 12A-12B. BAX activator BTSA1 (BAM38) has significant synergistic cytotoxicity with ABT-199 (venetoclax) and ABT-263 (navitoclax) at non-cytotoxic doses of BTSA1 in OCI-AML3 leukemia cells (A) and THP-1 cells (B) within 24 h treatments. The $IC_{50}$ values are reported in µM or nM concentrations.
Figure 12B:
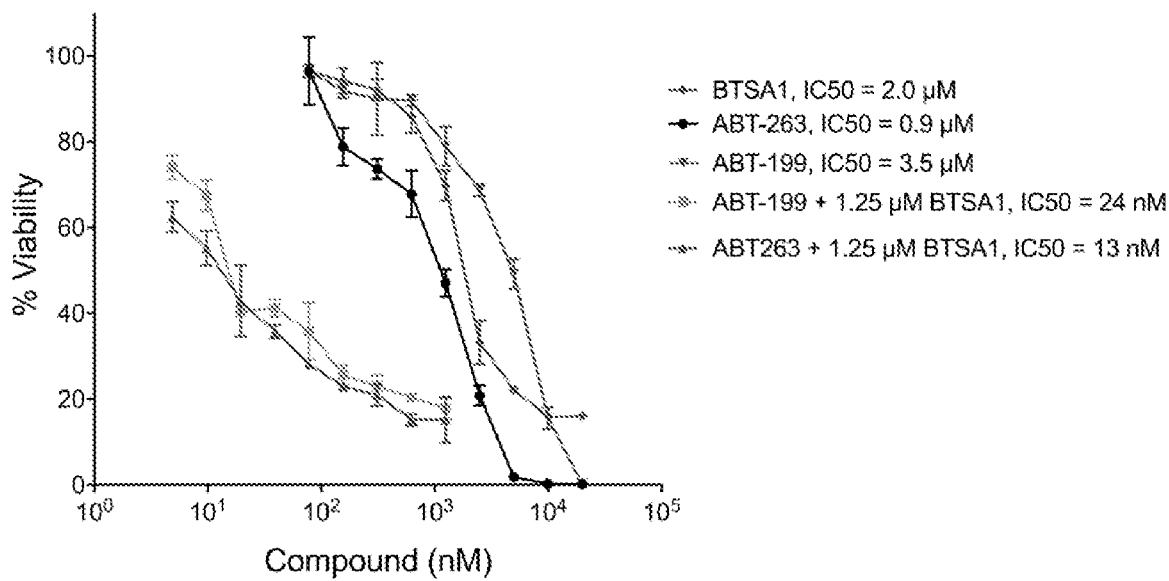
Figure 13A:
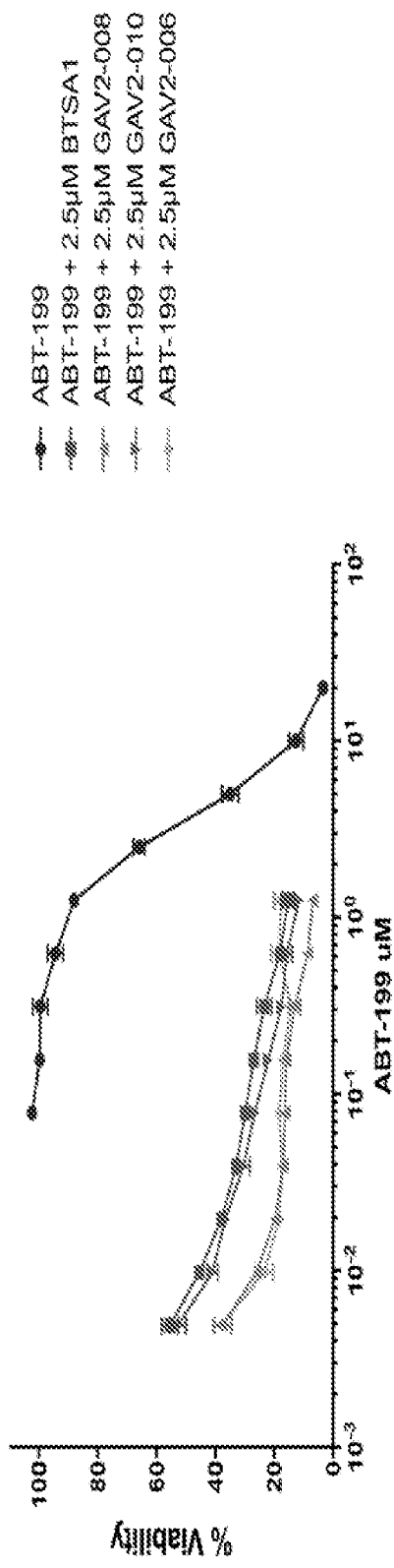
FIG. 13A-13C. BAX activator compounds (GAV2-006, GAV2-008, GAV2-010 and BTSA1) have significant synergistic cytotoxicity with ABT-199 (venetoclax) at non-cytotoxic doses for either compound in OCI-AML3 leukemia cells within 24 h treatments. The $IC_{50}$ values are reported in µM concentrations in Table 1. (A)-(C) show data with three different concentrations of the BAX activator compounds: (A) 2.5 µM, (B) 1.25 µM, (C) 0.625 µM.
Figure 13B:
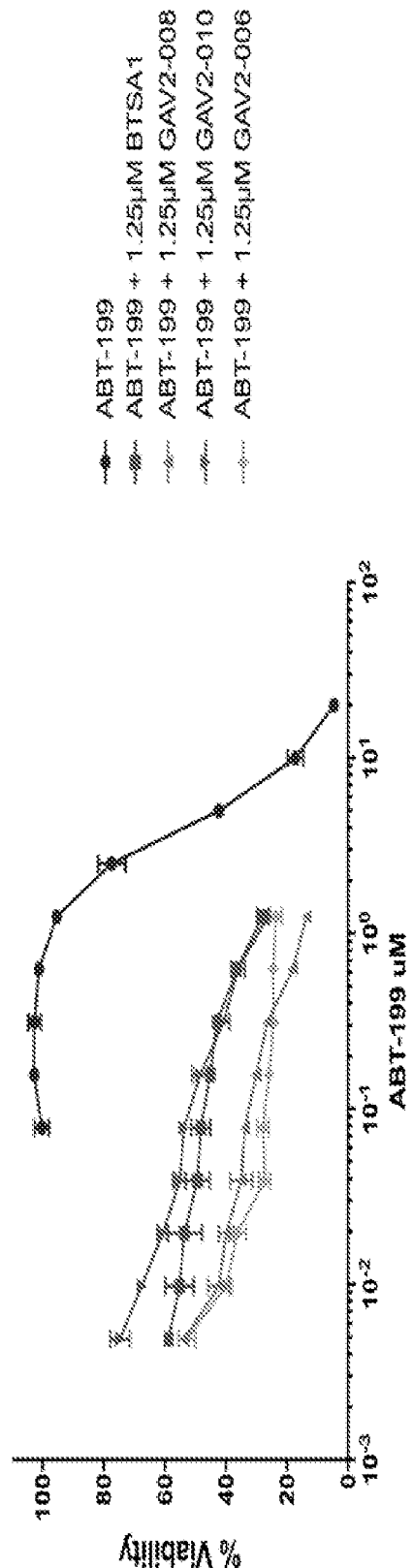
Figure 13C:
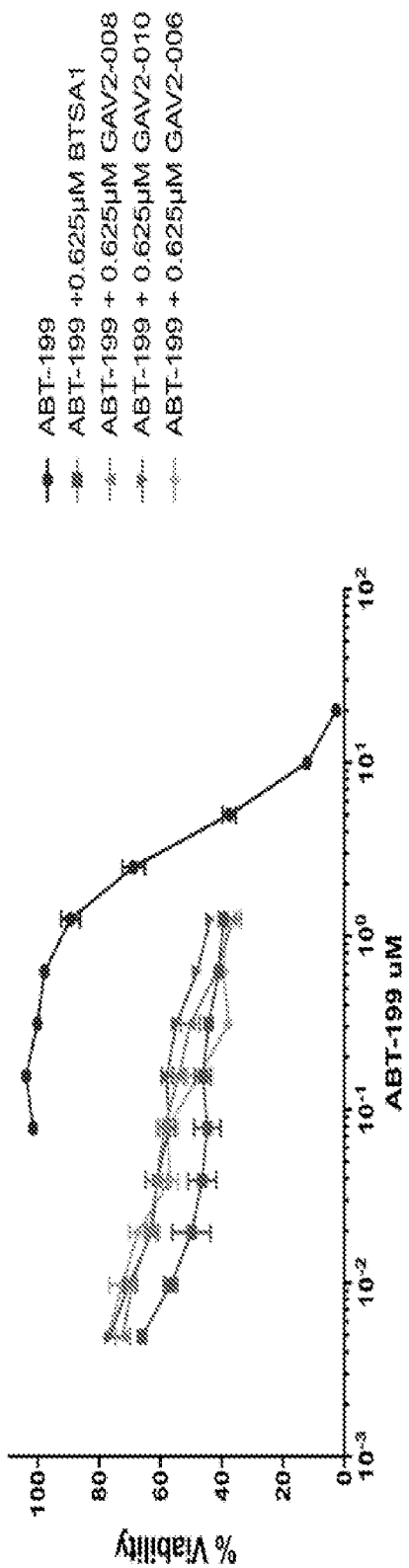
Figure 14:
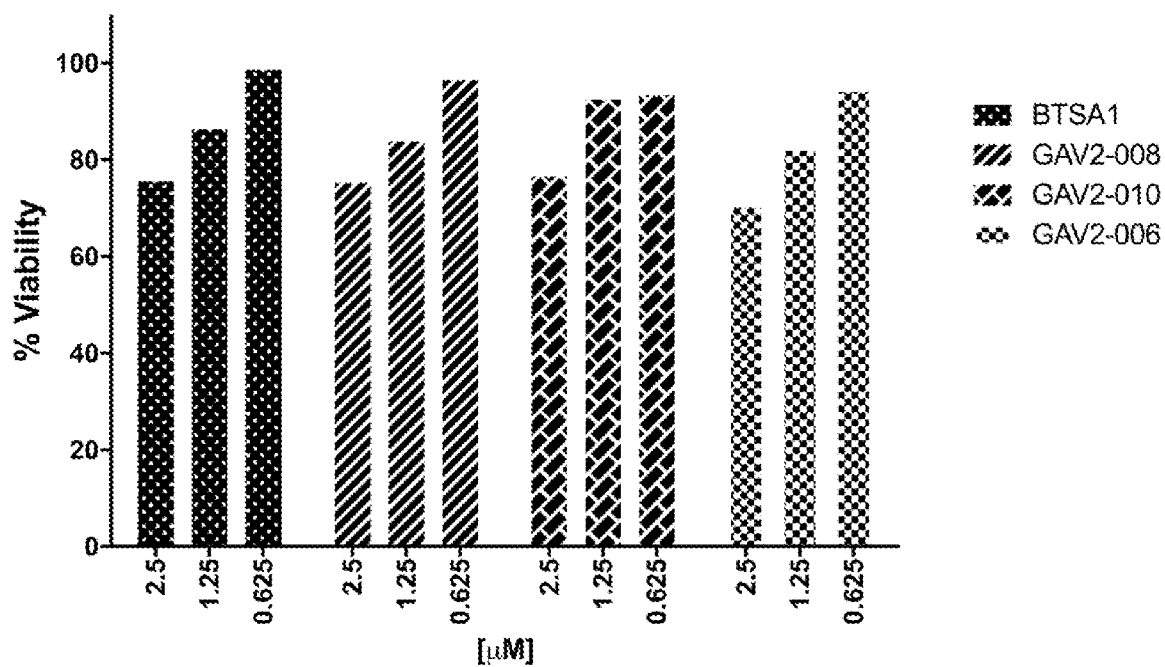
FIG. 14. Cytotoxicity effect of BAX activators (GAV2-006, GAV2-008, GAV2-010 and BTSA1) at 3 indicated doses used in synergy experiments with ABT-199 in OCI-AML3 leukemia cells within 24 h treatments.
Figure 15A:
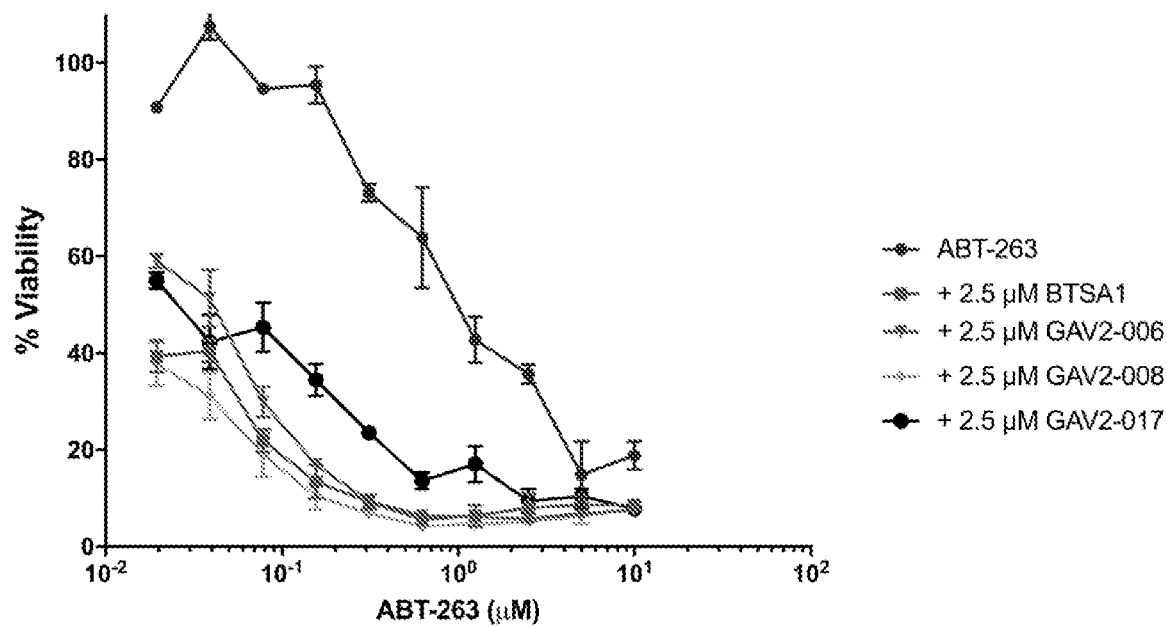
FIG. 15A-15B. BAX activator compounds (GAV2-006, GAV2-008, GAV2-017 and BTSA1) have significant synergistic cytotoxicity with (A) ABT-263 (navitoclax) and (B) ABT-199 (venetoclax) at non-cytotoxic doses for either compound in OCI-AML3 leukemia cells within 24 h treatments. The $IC_{50}$ values are reported in M concentrations.
Figure 15B:
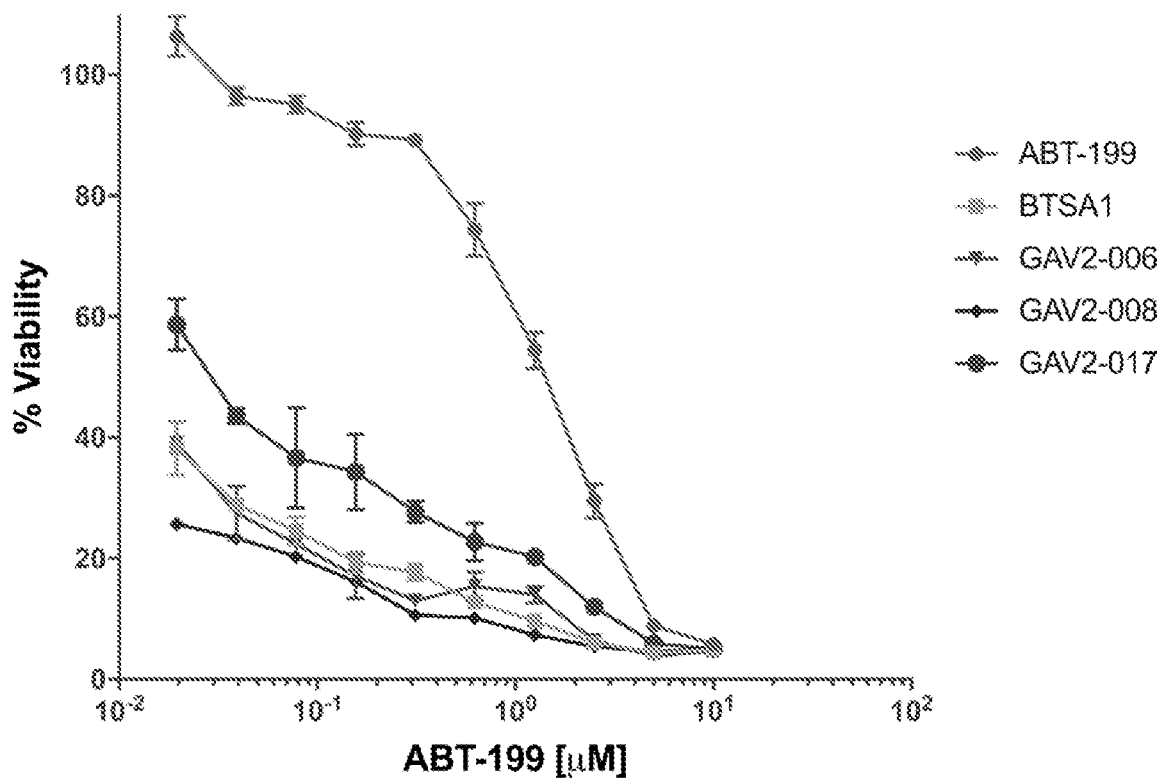
Figure 16A:
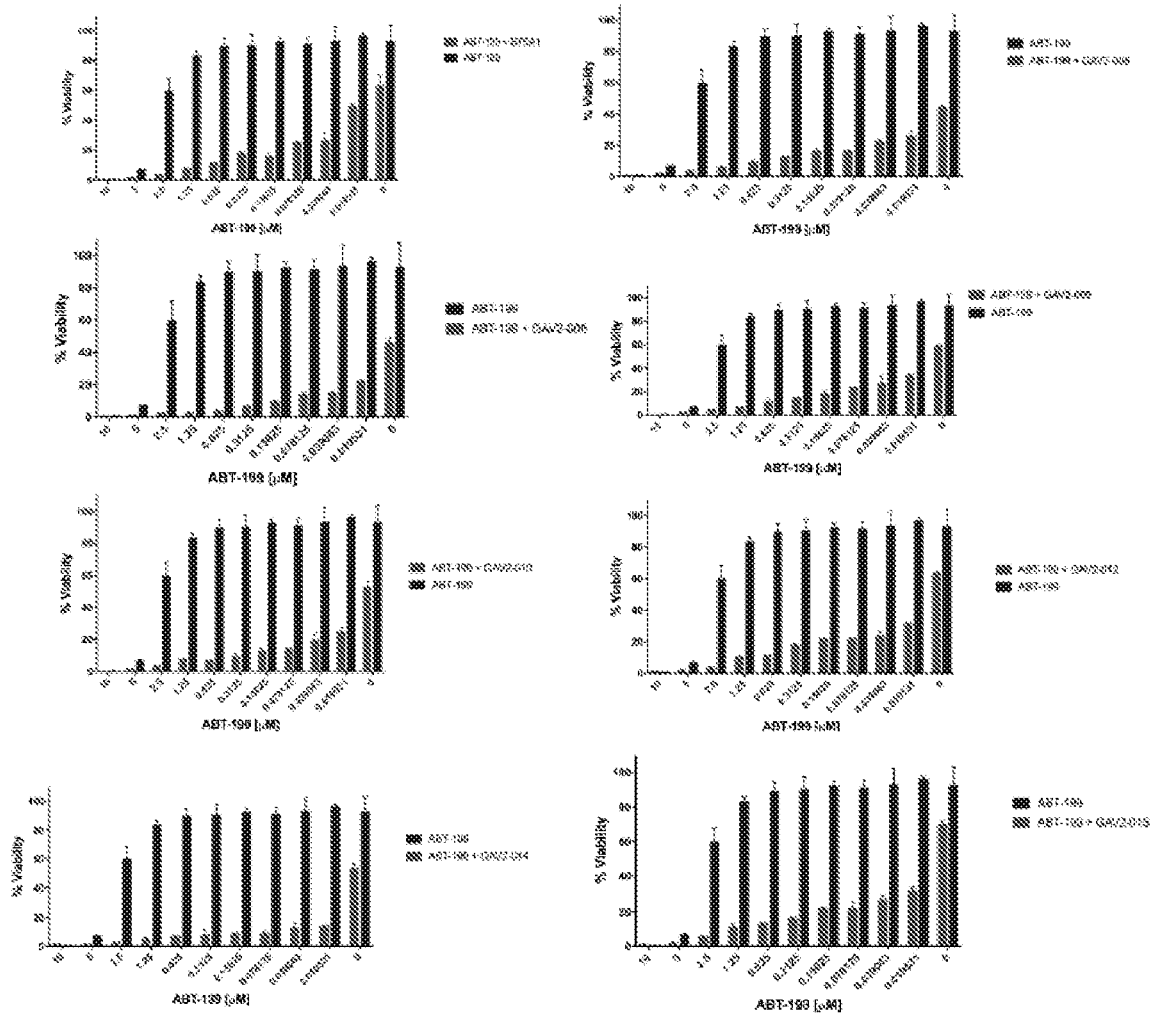
FIG. 16A-16B. BAX activator compounds have significant synergistic cytotoxicity with ABT-199 (venetoclax) at non-cytotoxic doses for either compound in OCI-AML3 leukemia cells within 24 h treatments. Effects of different concentrations of 8 different BAX activator compounds are shown in each of (A) and (B).
Figure 16B:
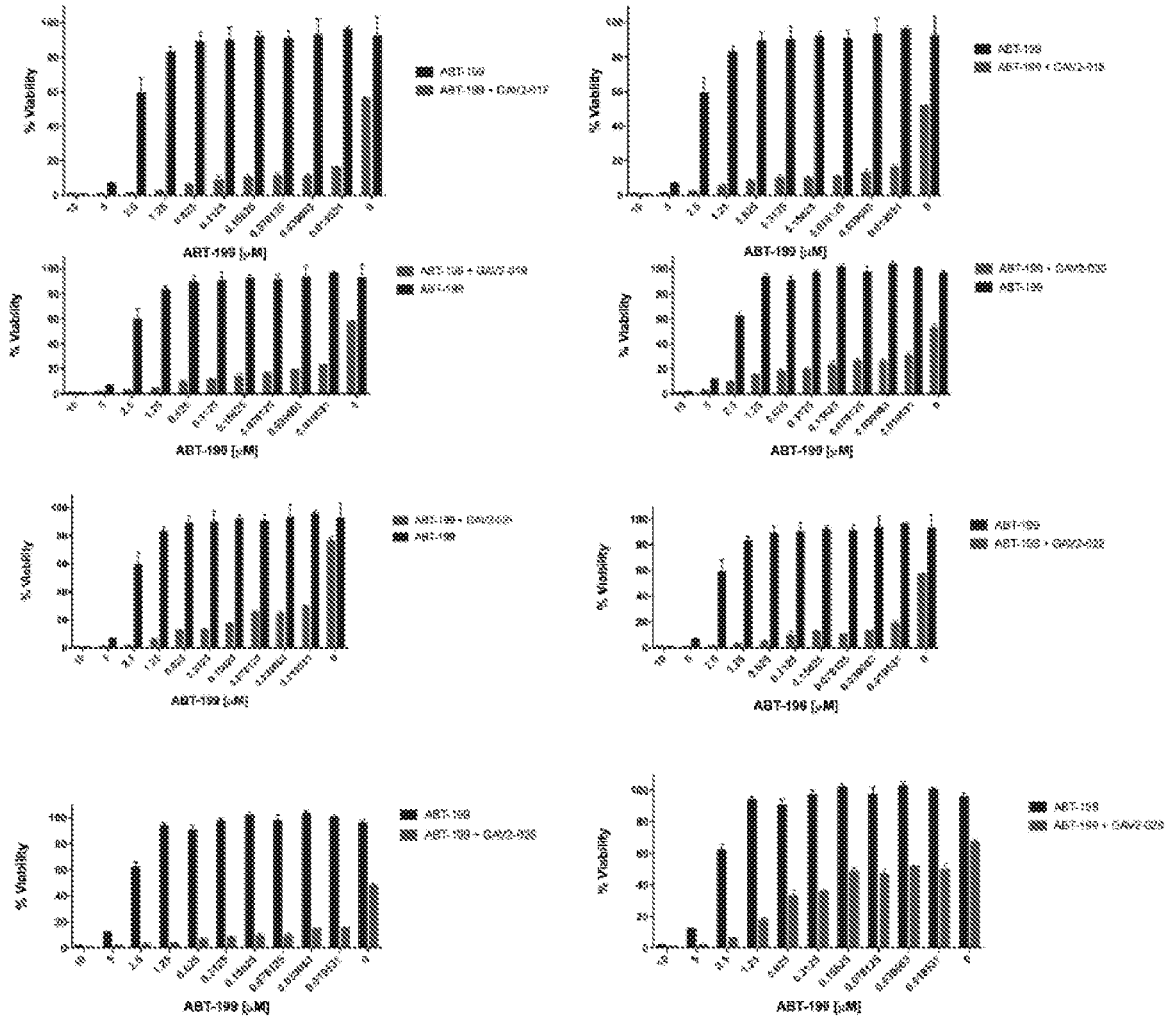

Studies were conducted with many other GAV BAX activator compounds, the structures of which are illustrated herein. FIG. 8 illustrates the effectiveness of compound GAV2-006 using 200 cancer cell lines. Data with the 18 most sensitive cancer types, by average $IC_{50}$, are shown in FIG. 8B-8D. FIGS. 9-10 illustrate viability assays of the human AML cell line OCI-AML3 exposed to different BAX activator compounds. Note the superior effectiveness of the GAV compounds compared to BAM7.

The BAX activator compounds can have significant synergistic cytotoxicity with ABT-199 (venetoclax) or ABT-263 (navitoclax), as illustrated in FIGS. 12-16.

TABLE 1

BAX activator compounds (GAV2-006, GAV2-008, GAV2-010 and BTSA1) have significant synergistic cytotoxicity with ABT-199 (venetoclax) at non-cytotoxic doses in OCI-AML3 leukemia cells with 24 h treatment. $IC_{50}$ values are reported in µM concentrations at three different concentrations (2.5, 1.25 and 0.625 µM) of the BAX activator compounds. Data plotted in FIG. 13A-13C.

| BAX Activator Concentration | ABT-199 | ABT-199 + BTSA1 | ABT-199 + GAV2-008 | ABT-199 + GAV2-010 | ABT-199 + GAV2-006 |
| --- | --- | --- | --- | --- | --- |
| 2.5 µM | 3.652 | 0.01241 | 0.003893 | 0.009945 | 0.003822 |
| 1.25 µM | 4.803 | 0.05282 | 0.0128 | 0.09445 | 0.00988 |
| 0.625 µM | 3.905 | 0.05043 | 0.1744 | 0.2431 | 0.1229 |

Discussion

Since the discovery of pro-apoptotic BAX, which was more than two decades ago (Olitvai et al., 1993) numerous studies have provided evidence that BAX is a critical protein that controls the gateway to mitochondrial outer membrane permeabilization and apoptosis (Luna-Vargas and Chipuk, 2016; Walensky and Gavathiotis, 2011; Wei et al., 2001). Direct BAX activation by select BH3-only proteins such as BIM, BID and PUMA has been established as a physiological mechanism that initiates the mitochondrial apoptotic pathway during development and homeostasis (Ren et al., 2010). Moreover, cancer cells neutralize BAX activation by deregulation or suppression of BH3-only proteins, and/or overexpression of anti-apoptotic BCL-2 proteins (Letai, 2008; Juin et al., 2013; Leverson et al., 2015). Structural, biochemical and cellular data have been provided for the identification and characterization of a BH3-binding site of inactive BAX that regulates activation of cytosolic BAX (Gavathiotis et al., 2008; Gavathiotis et al., 2010). These studies enable a novel therapeutic strategy in cancer cells to provide a powerful drug that would directly activate BAX and lead to mitochondrial permeabilization and apoptosis. Essentially, such a drug would replace the function of the BH3-only proteins that are kept suppressed either by anti-apoptotic BCL-2 proteins or other mechanisms in cancer (Hata et al., 2015; Letai, 2008).

The present studies, using structure-based drug design and medicinal chemistry based on established mechanism of BAX activation by natural and synthetic activators, have characterized a pharmacologically optimized small molecule BAX activator. BTSA1 specifically targets the N-terminal activation site of BAX with high nanomolar affinity. BTSA1 mimics some interactions of the BIM BH3 peptide but also localizes its structure at a distinct position on the structure of BAX, close to the α1-α2 loop. Its binding mode is consistent with the α1-α2 loop conformational change and exposure of the 6A7 epitope; therefore, BTSA1-binding has a strong capacity to initiate conformational changes that facilitate BAX mitochondrial translocation and oligomerization and lead to mitochondrial dysfunction (Gavathiotis et al., 2008; Kim et al., 2009).

BTSA1 is effective at inducing prompt BAX activation and BAX-dependent apoptosis in leukemia cell lines. Moreover, BTSA1 has specific cell death activity through BAX and has no activity in the absence or reduction of BAX expression or inhibition of BAX activation. Importantly, a biotinylated BTSA1 was used to demonstrate the engagement of BTSA1 to BAX in vivo and the lack of binding to other BCL-2 proteins. Sensitivity to BTSA1 and the impact of BAX activation is relative to the expression levels of BAX, which in leukemia cells are sufficient to induce robust apoptosis and overcome the blockade of endogenously upregulated anti-apoptotic BCL-2 proteins. However, further overexpression of anti-apoptotic BCL-2 proteins reduces the impact of BTSA1, consistent with the heterodimeric mechanism of anti-apoptotic blockade of BAX. Further studies indicated that cytosolic BAX in leukemia cell lines is in monomeric conformation and primed for BAX activation, whereas the formation of the autoinhibited BAX dimer may provide significant resistance to BAX activation by BTSA1. Therefore, the remarkable selectivity of BTSA1 for leukemia cells compared to normal cells is not only supported by the priming effect of cancer cells but also from the conformational predisposition of BAX molecules for activation by BTSA1 (Garner et al., 2016). Consistent with this data, a recent report demonstrated the insensitivity of most adult healthy somatic tissues to BAX activation by BIM BH3 (Sarosiek et al., 2017), suggesting an attractive rationale for direct BAX activation in cancer.

AML remains a challenging cancer to treat and current chemotherapy regimens result in poor 5-year survival (<25%), which is even worse in the elderly individuals who represent the majority of AML patients. Unfavorable outcomes have been associated with the existence of leukemic and pre-leukemic stem cells that are resistant to current treatments and are driving AML relapse (Huff et al., 2006; Jan et al., 2012; Slush et al., 2014). The present findings demonstrate that BTSA1-induced BAX activation is effective in primary AML samples and, when applied in vivo, achieved remarkable efficacy in human AML xenografts and increased survival. It is noteworthy that BTSA1 is also effective in leukemic stem cell-enriched fractions (CD34+ CD38-) from high-risk AML patients. Surprisingly, not only do AML blasts display higher expression of BAX but also highly purified stem and progenitor cell populations from AML patients when compared to healthy counterparts. This may be a critical factor for the overall sensitivity of AML blasts and pre-leukemic stem cells to BTSA1 and the observed therapeutic index of direct BAX activation. Overall, the data support BAX activators as effective monotherapy treatment for AML and also provide a strong rationale for activating mitochondrial apoptosis by combining BAX activation and BCL-2 inhibition for more effective leukemic remission.

In summary, this study provides preclinical proof for BAX as a druggable target and the therapeutic potential of direct BAX activation as a novel treatment strategy in AML. These findings demonstrate that direct BAX activation through small molecule targeting of the BAX trigger site can provide a specific and efficacious anti-tumor effect without adversely affecting healthy cells. BTSA1 has high potency, well-characterized mechanism of action, selectivity, excellent pharmacokinetic profile, oral bioavailability and synthetic ease that provides therapeutic potential in cancer.

REFERENCES

Barretina, J., G. Caponigro, N. Stransky, K. Venkatesan, A. A. Margolin, et al. (2012). The Cancer Cell Line Encyclopedia enables predictive modelling of anticancer drug sensitivity. Nature 483: 603-607.

Barreyro, L., Will, B., Bartholdy, B., Zhou, L., Todorova, T. I., Stanley, R. F., Ben-Neriah, S., Montagna, C., Parekh, S., Pellagatti, A., et al. (2012). Overexpression of IL-1 receptor accessory protein in stem and progenitor cells and outcome correlation in AML and MDS. Blood 120, 1290-1298.

Belmar, J., and Fesik, S. W. (2015). Small molecule Mcl-1 inhibitors for the treatment of cancer. Pharmacol. & Ther. 145, 76-84.

Beroukhim, R., Mermel, C. H., Porter, D., Wei, G., Raychaudhuri, S., Donovan, J., Barretina, J., Boehm, J. S., Dobson, J., Urashima, M., et al. (2010). The landscape of somatic copy-number alteration across human cancers. Nature 463, 899-905.

Bleicken, S., Jeschke, G., Stegmueller, C., Salvador-Gallego, R., Garcia-Saez, A. J., and Bordignon, E. (2014). Structural model of active Bax at the membrane. Mol. Cell 56, 496-505.

Bombrun, A., Gerber, P., Casi, G., Terradillos, O., Antonsson, B., and Halazy, S. (2003). 3,6-dibromocarbazole piperazine derivatives of 2-propanol as first inhibitors of cytochrome c release via Bax channel modulation. J. Med. Chem. 46, 4365-4368.

Bredesen, D. E., Rao, R. V., Mehlen, P. (2006) Cell death in the nervous system. *Nature* 443, 796-802.

Chipuk, J. E., et al. (2010) The BCL-2 family reunion. *Mol. Cell.* 37, 299-310.

Czabotar, P. E., Westphal, D., Dewson, G., Ma, S., Hockings, C., Fairlie, W. D., Lee, E. F., Yao, S., Robin, A. Y., Smith, B. J., et al. (2013). Bax crystal structures reveal how BH3 domains activate Bax and nucleate its oligomerization to induce apoptosis. Cell 152, 519-531.

Danial, N. N., Korsmeyer, S. J. (2004) Cell death: critical control points. *Cell* 116, 205-219.

Johnstone, R. W., Ruefli, A. A., Lowe, S. W. (2002) Apoptosis: a link between cancer genetics and chemotherapy *Cell* 108, 153-164.

Fallahi-Sichani, M., S. Honardejad, L. M. Heiser, J. W. Gray, and P. K. Sorger (2013). Metrics other than potency reveal systematic variation in responses to cancer drugs. Nat. Chem. Biol. 9: 708-714.

Gao, J., Aksoy, B. A., Dogrusoz, U., Dresdner, G., Gross, B., Sumer, S. O., Sun, Y., Jacobsen, A., Sinha, R., Larsson, E., et al. (2013). Integrative analysis of complex cancer genomics and clinical profiles using the cBioPortal. Science Signal. 6, p11.

Gavathiotis, E., Suzuki, M., Davis, M. L., Pitter, K., Bird, G. H., Katz, S. G., Tu, H. C., Kim, H., Cheng, E. H., Tjandra, N., et al. (2008). BAX activation is initiated at a novel interaction site. Nature 455, 1076-1081.

Garner T P, Lopez A, Reyna D E, Spitz A Z, Gavathiotis E. Progress in targeting the BCL-2 family of proteins. Curr Opin Chem Biol. 2017 Jul. 20; 39:133-142. doi: 10.1016/j.cbpa.2017.06.014. [Epub ahead of print].

Garner, T. P., Reyna, D. E., Priyadarshi, A., Chen, H. C., Li, S., Wu, Y., Ganesan, Y. T., Malashkevich, V. N., Almo, S. S., Cheng, E. H., et al. (2016). An Autoinhibited Dimeric Form of BAX Regulates the BAX Activation Pathway. Mol. Cell 63, 485-497.

Gasparri, F., P. Cappella, and A. Galvani (2006). Multiparametric cell cycle analysis by automated microscopy. J. Biomol. Screen. 11: 586-598.

Gavathiotis, E., Reyna, D. E., Davis, M. L., Bird, G. H., and Walensky, L. D. (2010). BH3-triggered structural reorganization drives the activation of proapoptotic BAX. Mol. Cell 40, 481-492.

Gavathiotis, E., Reyna, D. E., Bellairs, J. A., Leshchiner, E. S., and Walensky, L. D. (2012). Direct and selective small-molecule activation of proapoptotic BAX. Nat. Chem. Biol. 8, 639-645.

Goff, D. J., Court Recart, A., Sadarangani, A., Chun, H. J., Barrett, C. L., Krajewska, M., Leu, H., Low-Marchelli, J., Ma, W., Shih, A. Y., et al. (2013). A Pan-BCL2 inhibitor renders bone-marrow-resident human leukemia stem cells sensitive to tyrosine kinase inhibition. Cell Stem Cell 12, 316-328.

Hanahan, D., and Weinberg, R. A. (2011). Hallmarks of cancer: the next generation. Cell 144, 646-674.

Hang, H. C.; Yu, C.; Pratt, M. R. Bertozzi, C. R; *J. Am. Chem. Soc.* 2004, 126, 6-7.

Hata, A. N., Engelman, J. A., and Faber, A. C. (2015). The BCL2 Family: Key Mediators of the Apoptotic Response to Targeted Anticancer Therapeutics. Cancer Discov. 5, 475-487.

Huff, C. A., Matsui, W., Smith, B. D., and Jones, R. J. (2006). The paradox of response and survival in cancer therapeutics. Blood 107, 431-434.

Jan, M., Snyder, T. M., Corces-Zimmerman, M. R., Vyas, P., Weissman, I. L., Quake, S. R., and Majeti, R. (2012). Clonal evolution of preleukemic hematopoietic stem cells precedes human acute myeloid leukemia. Sci. Transl. Med. 4, 149ra118.

Juin, P., Geneste, O., Gautier, F., Depil, S., and Campone, M. (2013). Decoding and unlocking the BCL-2 dependency of cancer cells. Nat. Rev. Cancer 13, 455-465.

Kim, H., Tu, H. C., Ren, D., Takeuchi, O., Jeffers, J. R., Zambetti, G. P., Hsieh, J. J., and Cheng, E. H. (2009). Stepwise activation of BAX and BAK by tBID, BIM, and PUMA initiates mitochondrial apoptosis. Mol. Cell 36, 487-499.

Konopleva, M., Contractor, R., Tsao, T., Samudio, I., Ruvalo, P. P., Kitada, S., Deng, X. M., Zhai, D. Y., Shi, Y. X., Sneed, T., et al. (2006). Mechanisms of apoptosis sensitivity and resistance to the BH3 mimetic ABT-737 in acute myeloid leukemia. Cancer Cell 10, 375-388.

Kotschy, A., Szlavik, Z., Murray, J., Davidson, J., Maragno, A. L., Le Toumelin-Braizat, G., Chanrion, M., Kelly, G. L., Gong, J. N., Moujalled, D. M., et al. (2016). The MCL1 inhibitor S63845 is tolerable and effective in diverse cancer models. Nature 538, 477-482.

Lagadinou, E. D., Sach, A., Callahan, K., Rossi, R. M., Neering, S. J., Minhajuddin, M., Ashton, J. M., Pei, S., Grose, V., O'Dwyer, K. M., et al. (2013). BCL-2 inhibition targets oxidative phosphorylation and selectively eradicates quiescent human leukemia stem cells. Cell Stem Cell 12, 329-341.

Letai, A. G. (2008). Diagnosing and exploiting cancer's addiction to blocks in apoptosis. Nat. Rev. Cancer 8, 121-132.

Leverson, J. D., Phillips, D. C., Mitten, M. J., Boghaert, E. R., Diaz, D., Tahir, S. K., Belmont, L. D., Nimmer, P., Xiao, Y., Ma, X. M., et al. (2015). Exploiting selective BCL-2 family inhibitors to dissect cell survival dependencies and define improved strategies for cancer therapy. Sci. Transl. Med. 7, 279ra240.

Llambi, F., and Green, D. R. (2011). Apoptosis and oncogenesis: give and take in the BCL-2 family. Curr. Opin. Gen. & Dev. 21, 12-20.

Llambi, F., Moldoveanu, T., Tait, S. W., Bouchier-Hayes, L., Temirov, J., McCormick, L. L., Dillon, C. P., and Green, D. R. (2011). A unified model of mammalian BCL-2 protein family interactions at the mitochondria. Mol. Cell 44, 517-531.

Lovell, J. F., Billen, L. P., Bindner, S., Shamas-Din, A., Fradin, C., Leber, B., and Andrews, D. W. (2008). Membrane binding by tBid initiates an ordered series of events culminating in membrane permeabilization by Bax. Cell 135, 1074-1084.

Luna-Vargas, M. P., and Chipuk, J. E. (2016). Physiological and Pharmacological Control of BAK, BAX, and Beyond. Trends Cell. Biol. 26, 906-917.

Oltersdorf, T., Elmore, S. W., Shoemaker, A. R., Armstrong, R. C., Augeri, D. J., Belli, B. A., Bruncko, M., Deckwerth, T. L., Dinges, J., Hajduk, P. J., et al. (2005). An inhibitor of Bcl-2 family proteins induces regression of solid tumours. Nature 435, 677-681.

Oltvai, Z. N., Milliman, C. L., and Korsmeyer, S. J. (1993). Bcl-2 heterodimerizes in vivo with a conserved homolog, Bax, that accelerates programmed cell death. Cell 74, 609-619.

Pan, R., Hogdal, L. J., Benito, J. M., Bucci, D., Han, L., Borthakur, G., Cortes, J., DeAngelo, D. J., Debose, L., Mu, H., et al. (2014). Selective BCL-2 inhibition by ABT-199 causes on-target cell death in acute myeloid leukemia. Cancer Discov. 4, 362-375.

Perciavalle, R. M., and Opferman, J. T. (2013). Delving deeper: MCL-1's contributions to normal and cancer biology. Trends Cell Biol. 23, 22-29.

Ren, D., Tu, H. C., Kim, H., Wang, G. X., Bean, G. R., Takeuchi, O., Jeffers, J. R., Zambetti, G. P., Hsieh, J. J., and Cheng, E. H. (2010). BID, BIM, and PUMA are essential for activation of the BAX- and BAK-dependent cell death program. Science 330, 1390-1393.

Roberts, A. W., Davids, M. S., Pagel, J. M., Kahl, B. S., Puvvada, S. D., Gerecitano, J. F., Kipps, T. J., Anderson, M. A., Brown, J. R., Gressick, L., et al. (2016). Targeting BCL2 with Venetoclax in Relapsed Chronic Lymphocytic Leukemia. New Eng. J. Med. 374, 311-322.

Reed, J. C. (2008). Bcl-2-family proteins and hematologic malignancies: history and future prospects. Blood 111, 3322-3330.

Rudin, C. M., Hann, C. L., Garon, E. B., Ribeiro de Oliveira, M., Bonomi, P. D., Camidge, D. R., Chu, Q., Giaccone, G., Khaira, D., Ramalingam, S. S., et al. (2012). Phase II study of single-agent navitoclax (ABT-263) and biomarker correlates in patients with relapsed small cell lung cancer. Clin. Cancer Res. 18, 3163-3169.

Sarosiek, K. A., Fraser, C., Muthalagu, N., Bhola, P. D., Chang, W., McBrayer, S. K., Cantlon, A., Fisch, S., Golomb-Mello, G., Ryan, J. A., et al. (2017). Developmental Regulation of Mitochondrial Apoptosis by c-Myc Governs Age- and Tissue-Specific Sensitivity to Cancer Therapeutics. Cancer Cell 31, 142-156.

Schinke, C., Giricz, O., Li, W., Shastri, A., Gordon, S., Barreyro, L., Bhagat, T., Bhattacharyya, S., Ramachandra, N., Bartenstein, M., et al. (2015). IL8-CXCR2 pathway inhibition as a therapeutic strategy against MDS and AML stem cells. Blood 125, 3144-3152.

Shlush, L. I., Zandi, S., Mitchell, A., Chen, W. C., Brandwein, J. M., Gupta, V., Kennedy, J. A., Schimmer, A. D., Schuh, A. C., Yee, K. W., et al. (2014). Identification of pre-leukaemic haematopoietic stem cells in acute leukaemia. Nature 506, 328-333.

Souers, A. J., Leverson, J. D., Boghaert, E. R., Ackler, S. L., Catron, N. D., Chen, J., Dayton, B. D., Ding, H., Enschede, S. H., Fairbrother, W. J., et al. (2013). ABT-199, a potent and selective BCL-2 inhibitor, achieves antitumor activity while sparing platelets. Nat. Med. 19, 202-208.

Thornberry, N. A. and Y. Lazebnik (1998). Caspases: Enemies Within. Science 281: 1312-1316.

Uchime, O., Dai, Z., Biris, N., Lee, D., Sidhu, S. S., Li, S., Lai, J. R., and Gavathiotis, E. (2016). Synthetic Antibodies Inhibit Bcl-2-associated X Protein (BAX) through Blockade of the N-terminal Activation Site. J. Biol. Chem. 291, 89-102.

van Delft, M. F., Wei, A. H., Mason, K. D., Vandenberg, C. J., Chen, L., Czabotar, P. E., Willis, S. N., Scott, C. L., Day, C. L., Cory, S., et al. (2006). The BH3 mimetic ABT-737 targets selective Bcl-2 proteins and efficiently induces apoptosis via Bak/Bax if Mcl-1 is neutralized. Cancer Cell 10, 389-399.

Walensky, L. D., and Gavathiotis, E. (2011). BAX unleashed: the biochemical transformation of an inactive cytosolic monomer into a toxic mitochondrial pore. Trends Biochem. Sci. 36, 642-652.

Walensky et al., U.S. Pat. No. 9,303,024 B2, issued Apr. 5, 2016, Pyrazol-3-ones that activate pro-apoptotic BAX.

Wei, M. C., Zong, W. X., Cheng, E. H., Lindsten, T., Panoutsakopoulou, V., Ross, A. J., Roth, K. A., MacGregor, G. R., Thompson, C. B., and Korsmeyer, S. J. (2001). Proapoptotic BAX and BAK: a requisite gateway to mitochondrial dysfunction and death. Science 292, 727-730.

Youle, R. J., and Strasser, A. (2008). The BCL-2 protein family: opposing activities that mediate cell death. Nat. Rev. Mol. Cell. Biol. 9, 47-59.

Zhang, L., Yu, J., Park, B. H., Kinzler, K. W., and Vogelstein, B. (2000). Role of BAX in the apoptotic response to anticancer agents. Science 290, 989-992.

Zhang, Z., Subramaniam, S., Kale, J., Liao, C., Huang, B., Brahmbhatt, H., Condon, S. G., Lapolla, S. M., Hays, F. A., Ding, J., et al. (2016). BH3-in-groove dimerization initiates and helix 9 dimerization expands Bax pore assembly in membranes. EMBO J. 35, 208-236.

What is claimed is:

1. A pharmaceutical composition comprising a pharmaceutically acceptable carrier and a compound having the structure:

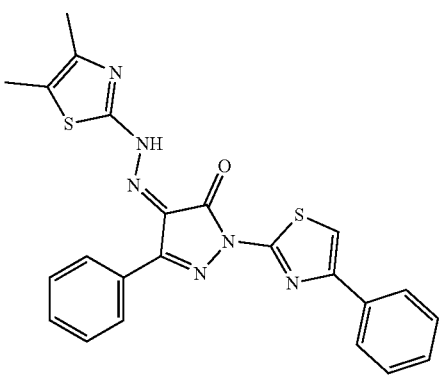

Gav2-006 or a pharmaceutically acceptable salt, ester, or prodrug thereof.

2. The pharmaceutical composition of claim 1, wherein the compound is present in an amount effective to activate BCL-2-associated X-protein (BAX).

3. The pharmaceutical composition of claim 2, wherein the compound activates cytosolic BAX.

4. The pharmaceutical composition of claim 2, wherein the compound specifically targets the N-terminal activation site of BAX with nanomolar affinity.

5. A method of treating a cancer in a subject comprising administering to the subject the pharmaceutical composition of claim 1, wherein the compound is in an amount effective to activate BCL-2-associated X-protein (BAX) in a subject.

6. The method of claim 5 comprising administering the pharmaceutical composition in combination with an inhibitor of BCL-2 or with an inhibitor of BCL-xL and BCL-2.

7. The method of claim 6, wherein the inhibitor of BCL-2 is ABT-199 or ABT-263.

8. The method of claim 6, wherein the inhibitor of BCL-2 and BCL-xL is ABT-263.

9. The method of claim 5, wherein the cancer is a leukemia or a solid tumor.

10. The method of claim 5, wherein the cancer is acute lymphoblastic leukemia (ALL), acute myeloid leukemia (AML), chronic lymphocytic leukemia (CLL) or chronic myeloid leukemia (CIVIL).

11. The method of claim 5, wherein the cancer is breast cancer, prostate cancer, lymphoma, skin cancer, pancreatic cancer, colon cancer, melanoma, malignant melanoma, ovarian cancer, brain or spinal cord cancer, primary brain carcinoma, medulloblastoma, neuroblastoma, glioma, head-neck cancer, glioma, glioblastoma, liver cancer, bladder cancer, stomach cancer, kidney cancer, placental cancer, cancer of the gastrointestinal tract, non-small cell lung cancer (NSCLC), head or neck carcinoma, breast carcinoma, endocrine cancer, eye cancer, genitourinary cancer, cancer of the vulva, ovary, uterus or cervix, hematopoietic cancer, myeloma, leukemia, lymphoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, chronic granulocytic leukemia, acute granulocytic leukemia, acute myelogenous leukemia, chronic myelogenous leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft tissue cancer, soft-tissue sarcoma, osteogenic sarcoma, sarcoma, primary macroglobulinemia, central nervous system cancer and retinoblastoma.

12. A method of inducing apoptosis in cancer cells and/or in leukemia stem cells in a subject comprising administering to the subject the compound in the pharmaceutical composition of claim 1 in an amount effective to induce apoptosis in cancer cells and/or in leukemia stem cells in a subject.

13. The method of claim 12, wherein the cancer cells are leukemia cells or solid tumor cells.

* * * * *

SEQUENCE LISTING

<160> NUMBER OF SEQ ID NOS: 7

<210> SEQ ID NO 1
<211> LENGTH: 192
<212> TYPE: PRT
<213> ORGANISM: Homo sapiens

<400> SEQUENCE: 1

Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
            20                  25                  30

```
Asp Arg Ala Gly Arg Met Gly Glu Ala Pro Glu Leu Ala Leu Asp
         35                  40                  45

Pro Val Pro Gln Asp Ala Ser Thr Lys Lys Leu Ser Glu Cys Leu Lys
 50                  55                  60

Arg Ile Gly Asp Glu Leu Asp Ser Asn Met Glu Leu Gln Arg Met Ile
 65                  70                  75                  80

Ala Ala Val Asp Thr Asp Ser Pro Arg Glu Val Phe Phe Arg Val Ala
                 85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 2
<211> LENGTH: 239
<212> TYPE: PRT
<213> ORGANISM: Homo sapiens

<400> SEQUENCE: 2

Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
             20                  25                  30

Gly Asp Val Gly Ala Ala Pro Pro Gly Ala Ala Pro Ala Pro Gly Ile
         35                  40                  45

Phe Ser Ser Gln Pro Gly His Thr Pro His Pro Ala Ala Ser Arg Asp
 50                  55                  60

Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Pro Val Val His Leu Thr
                 85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
210                 215                 220
```

Leu Val Gly Ala Cys Ile Thr Leu Gly Ala Tyr Leu Gly His Lys
225                 230                 235

<210> SEQ ID NO 3
<211> LENGTH: 205
<212> TYPE: PRT
<213> ORGANISM: Homo sapiens

<400> SEQUENCE: 3

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Val Gly Ala Leu Gly Asp Val Ser Leu Gly
        195                 200                 205

<210> SEQ ID NO 4
<211> LENGTH: 233
<212> TYPE: PRT
<213> ORGANISM: Homo sapiens

<400> SEQUENCE: 4

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
            115                 120                 125

Glu Leu Phe Arg Asp Gly Val Asn Trp Gly Arg Ile Val Ala Phe Phe
130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
210                 215                 220

Leu Leu Gly Ser Leu Phe Ser Arg Lys
225                 230

<210> SEQ ID NO 5
<211> LENGTH: 227
<212> TYPE: PRT
<213> ORGANISM: Homo sapiens

<400> SEQUENCE: 5

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Val Arg Thr Lys
            180                 185                 190

Pro Leu Val Cys Pro Phe Ser Leu Ala Ser Gly Gln Arg Ser Pro Thr
        195                 200                 205

Ala Leu Leu Leu Tyr Leu Phe Leu Leu Cys Trp Val Ile Val Gly Asp
    210                 215                 220

Val Asp Ser
225

```
<210> SEQ ID NO 6
<211> LENGTH: 20
<212> TYPE: PRT
<213> ORGANISM: Artificial Sequence
<220> FEATURE:
<223> OTHER INFORMATION: corresponding to the BH3 domain of BIM
<220> FEATURE:
<221> NAME/KEY: MISC_FEATURE
<222> LOCATION: (10)..(10)
<223> OTHER INFORMATION: x= a non-natural amino acid inserted for olefin
      metathesis
<220> FEATURE:
<221> NAME/KEY: MISC_FEATURE
<222> LOCATION: (14)..(14)
<223> OTHER INFORMATION: x= a non-natural amino acid inserted for olefin
      metathesis

<400> SEQUENCE: 6

Glu Ile Trp Ile Ala Gln Glu Leu Arg Xaa Ile Gly Asp Xaa Phe Asn
1               5                   10                  15

Ala Tyr Tyr Ala
            20

<210> SEQ ID NO 7
<211> LENGTH: 20
<212> TYPE: PRT
<213> ORGANISM: Artificial Sequence
<220> FEATURE:
<223> OTHER INFORMATION: corresponding to the BH3 domain of BIM
<220> FEATURE:
<221> NAME/KEY: MISC_FEATURE
<222> LOCATION: (10)..(10)
<223> OTHER INFORMATION: x= a non-natural amino acid inserted for olefin
      metathese
<220> FEATURE:
<221> NAME/KEY: MISC_FEATURE
<222> LOCATION: (14)..(14)
<223> OTHER INFORMATION: x= a non-natural amino acid inserted for olefin
      metathese

<400> SEQUENCE: 7

Glu Ile Trp Ile Ala Gln Glu Leu Arg Xaa Ile Gly Asp Xaa Phe Asn
1               5                   10                  15

Ala Tyr Tyr Ala
            20
```